US012595258B2

(12) United States Patent
Fabritius et al.

(10) Patent No.: US 12,595,258 B2
(45) Date of Patent: Apr. 7, 2026

(54) HETEROCYCLIC DERIVATIVES, PHARMACEUTICAL COMPOSITIONS AND THEIR USE IN THE TREATMENT OR AMELIORATION OF CANCER

(71) Applicant: TOLREMO THERAPEUTICS AG, Muttenz (CH)

(72) Inventors: Charles-Henry Fabritius, Muttenz (CH); Koen Hekking, Muttenz (CH); Dorothea Gruber, Muttenz (CH); Rutger Folmer, Muttenz (CH); Stefanie Flückiger-Mangual, Muttenz (CH); Thomas Bohnacker, Muttenz (CH); Martin Schwill, Muttenz (CH); Debora Schmitz-Rohmer, Muttenz (CH)

(73) Assignee: Tolremo Therapeutics AG, Muttenz (CH)

( * ) Notice: Subject to any disclaimer, the term of this patent is extended or adjusted under 35 U.S.C. 154(b) by 0 days.

(21) Appl. No.: 19/179,235

(22) Filed: Apr. 15, 2025

(65) Prior Publication Data

US 2025/0243191 A1 Jul. 31, 2025

Related U.S. Application Data

(63) Continuation of application No. 18/285,800, filed as application No. PCT/EP2022/059295 on Apr. 7, 2022.

(51) Int. Cl.

| | |
|---|---|
| ***C07D 413/14*** | (2006.01) |
| ***A61K 31/506*** | (2006.01) |
| ***A61P 35/00*** | (2006.01) |
| ***C07D 401/14*** | (2006.01) |
| ***C07D 405/14*** | (2006.01) |

(52) U.S. Cl.

CPC .......... *C07D 413/14* (2013.01); *A61K 31/506* (2013.01); *A61P 35/00* (2018.01); *C07D 401/14* (2013.01); *C07D 405/14* (2013.01)

(58) Field of Classification Search

None

See application file for complete search history.

(56) References Cited

U.S. PATENT DOCUMENTS

| | | | | |
|---|---|---|---|---|
| 3,773,919 | A | 11/1973 | Boswell | |
| 4,485,045 | A | 11/1984 | Regen | |
| 4,544,545 | A | 10/1985 | Ryan | |
| 6,570,036 | B1 | 5/2003 | Reuter | |
| 10,648,983 | B2 * | 5/2020 | Filvaroff | A61P 35/00 |
| 2016/0046608 | A1 | 2/2016 | Cohen | |
| 2016/0317632 | A1 | 11/2016 | Albrecht | |
| 2017/0291902 | A1 | 10/2017 | Perl | |
| 2018/0334454 | A1 | 11/2018 | Lanman | |
| 2019/0144444 | A1 | 5/2019 | Blake | |
| 2023/0226057 | A1 | 7/2023 | Fluckiger-Mangual | |
| 2023/0233558 | A1 | 7/2023 | Fluckiger-Mangual | |
| 2023/0255966 | A1 | 8/2023 | Fluckiger-Mangual | |

FOREIGN PATENT DOCUMENTS

| | | | |
|---|---|---|---|
| CN | 107406454 | A | 11/2017 |
| CN | 110621316 | A | 12/2019 |
| CN | 110996960 | A | 4/2020 |
| CN | 110996962 | A | 4/2020 |
| CN | 111328283 | A | 6/2020 |
| DE | 3218121 | A1 | 11/1983 |
| EP | 0036676 | A1 | 9/1981 |
| EP | 0052322 | A2 | 5/1982 |
| EP | 0088046 | A2 | 9/1983 |
| EP | 0102324 | A2 | 3/1984 |
| EP | 0133988 | A2 | 3/1985 |
| EP | 0142641 | A2 | 5/1985 |
| EP | 0143949 | A1 | 6/1985 |
| JP | 2001089452 | A | 4/2001 |
| JP | 2015524798 | A | 8/2015 |
| WO | 9741833 | A1 | 11/1997 |

(Continued)

OTHER PUBLICATIONS

Atzrodt et al, "Synthesis of stable isotope labelled internal standards for drug-drug interaction (DDI) studies," Bioogranic Medicinal Chemistry, vol. 20, Issue 18: 5658-5667 (Sep. 15, 2012).

Bai et al., "Application progress in pyrimidine compound," Shanxi Chemical Industry, Issue 1: 16-19 (Feb. 2009)—Abstract.

Boumahdi et al, "The great escape: tumour cell plasticity in resistance to targeted therapy," Nat Rev Drug Discov. (Jan. 19, 2019).

Cai et al, "Intratumoral De Novo Steroid Synthesis Activates Androgen Receptor in Castration-Resistant Prostate Cancer and Is Upregulated by Treatment with CYP17A1 Inhibitors," Therapeutics, Targets, and Chemical Biology, American Association for Cancer Research, 71 (20) (Oct. 15, 2011).

Canon et al., "The clinical KRAS (G12C) inhibitor AMG 510 drives anti-tumor immunity," Nature, vol. 575 (Oct. 2019).

(Continued)

*Primary Examiner* — Kamal A Saeed
*Assistant Examiner* — Quincy Mckoy
(74) *Attorney, Agent, or Firm* — KDW Firm PLLC

(57) ABSTRACT

The present invention relates to compounds of formula (I) or salts, solvates, cocrystals, tautomers, or mixtures thereof. Furthermore, the present invention relates to pharmaceutical compositions comprising said compounds. Moreover, the present invention relates to the compounds of formula (I) or the salts, solvates, cocrystals, tautomers, or mixtures thereof or the pharmaceutical compositions for use as a medicament and to the compounds of formula (I) or the salts, solvates, cocrystals, tautomers, or mixtures thereof or the pharmaceutical compositions for use in the treatment or amelioration of cancer. Optionally, the compounds of formula (I) or the salts, solvates, cocrystals, tautomers, or mixtures thereof or the pharmaceutical compositions are administered in combination with a second therapeutic agent, in particular an anti-cancer agent.

4 Claims, No Drawings

(56) References Cited

FOREIGN PATENT DOCUMENTS

| | | | |
|---|---|---|---|
| WO | 9916419 | A1 | 4/1999 |
| WO | 01085136 | A2 | 11/2001 |
| WO | 0222607 | A1 | 3/2002 |
| WO | 0222608 | A1 | 3/2002 |
| WO | 03053411 | A1 | 7/2003 |
| WO | 2005100341 | A1 | 10/2005 |
| WO | 2008006583 | A1 | 1/2008 |
| WO | 2009050183 | A2 | 4/2009 |
| WO | 2013148114 | A1 | 10/2013 |
| WO | 2014177524 | A1 | 11/2014 |
| WO | 2015103355 | A1 | 7/2015 |
| WO | 2016123054 | A1 | 8/2016 |
| WO | 2016197009 | A1 | 12/2016 |
| WO | 2018203256 | A1 | 11/2018 |
| WO | 2019045824 | A1 | 3/2019 |
| WO | 2019097078 | A1 | 5/2019 |
| WO | 2020023768 | A1 | 1/2020 |
| WO | 2020035065 | A1 | 2/2020 |
| WO | 2020045941 | A1 | 3/2020 |
| WO | 2020055755 | A1 | 3/2020 |
| WO | 2020055756 | A1 | 3/2020 |
| WO | 2020055758 | A1 | 3/2020 |
| WO | 2020055761 | A1 | 3/2020 |
| WO | 2020118066 | A1 | 6/2020 |
| WO | 2020127200 | A1 | 6/2020 |
| WO | 2021064142 | A1 | 4/2021 |
| WO | 2021194326 | A1 | 9/2021 |

OTHER PUBLICATIONS

Elbadawy et al., "Emerging Roles of C-Myc in Cancer Stem Cell-Related Signaling and Resistance to Cancer Chemotherapy: A Potential Therapeutic Target Against Colorectal Cancer," International Journal of Molecular Sciences, vol. 20, No. 2340: 16 pages, (2019).

Eppstein et al., "Biological activity of liposome-encapsulated murine interferon gamma is mediated by a cell membrane receptor," Proc. Natl. Acad. Sci. (USA), vol. 82: 3688-3692 (1985).

Fell et al., "Identification of the Clinical Development Candidate MRTX849, a covalent KRASG12C Inhibitor for the Treatment of Cancer," Journal of Medicinal Chemistory, vol. 63 (Apr. 2020).

Gabizon et al., "Hitting KRAS When It's Down," Journal of Medicinal Chemistry, vol. 63 (Jul. 2020).

Garcia-Carpizo et al., "CREBBP/EP300 bromodomains are critical to sustain the GATA1/MYC regulatory axis in proliferation," Epigenetics & Chromatin, vol. 11, No. 30: 15 pages (2018).

Hay et al, "Discovery and Optimization for Small-Molecule Ligands for CBP/p300 Bromodomains," Journal of the American Chemical Society, vol. 136: 9308-9319 (Jun. 19, 2014).

Hwang et al., "Hepatic uptake and degradation of uniamellar sphingomyelin/cholesterol liposomes: a kinetic study," Proc. Natl. Acad. Sci. (USA), vol. 77: 4030-4034 (1980).

Leonnetti et al, "Resistance mechanisms to osimertinib in EGFR-mutated non-small cell lung cancer, " British Journal of Cancer (Mar. 5, 2019).

Li et al., "A potent CBP/p300-Snail interaction inhibitor suppresses tumor growth and metastasis in wild-type p53-expressing cancer," Science Advances, Research Article, vol. 6: 17 pages. (2020).

Liu et al., "Idiopathic Pulmonary Fibrosis: Current Status, Recent Progress, and Emerging Targets," Journal of Medicinal Chemistry, vol. 60, Issue 2: 527-553 (2017)—Abstract.

Lockley et al, "Metal-catalysed hydrogen isotope exhange labeling: a brief overview," Journal of Labelled Componds and Radiopharmceuticals, vol. 53, Issue 11-12: 635-644 (Dec. 17, 2010).

Masters et al, "Spray Drying Handbook," K. Masters Longman Group Ltd, Harlow, Essex, 710 pp. (Apr. 25, 2007).

Modvig et al., "Two-chamber hydrogen generation and application: access to pressurized deuterium gas," J. Org. Chem., vol. 79: 5861-5868 (2014).

Ogiwara et al,"Targeting p300 Addiction in CBP-Deficient Cancers Causes Synthetic Lethality by Apoptotic Cell Death due to Abrogation of MYC Expression," American Association for Cancer Research (2015).

Picaud et al, "Generation of a Selective Small Molecule Inhibitor of the CBP/p300 Bromodomain for Leukemia Therapy," Therapeutics, Targets, And Chemical Biology, Cancer Research, 75 (23): 5106-5119 (2015).

Romero et al, "Supporting Information GNE-781, A Highly Advanced Potent and Selective Bromodomain Inhibitor of Cyclic Adenosine Monophosphate Response Element Binding Protein, Binding Protein (CBP)," Genentech, Inc (2017).

Schleger et al., "c-MYC Activation in Primary and Metastatic Ductal Adenocarcinoma of the Pancreas: Incidence, Mechanisms, and Clinical Significance," Modern Pathology, vol. 15, No. 4: 462-469 (2002).

Springuel et al, "The importance of solvent selection for stoichimetrically diverse cocrystal systems: Caffeine/Maleic Acid 1:1 and 2:1 cocrystals," Universite Catholique de Louvain, IMCN (2012).

Uprety et al., "KRAS: From undruggable to druggable Cancer Target," Cancer Treatment Reviews, vol. 89 (Jul. 2020).

Van Maldegem et al., "Mutant KRAS at the Heart of Tumor Immune Evasion," Immunity, vol. 52 (Jan. 2020).

Wang et al, "Clopidogrel with Aspirin in Acute Minor Stroke or Transient Ischemic Attack," The New England Journal of Medicine (Jul. 4, 2013).

Wang et al., "Expression of p300/CBP and Smad4 and its significance in non-small-cell lung cancer," Journal of Wannan Medical College, vol. 30, No. 6: 452-456 (2011).

Welti et al, "Targeting the p300/CBP Axis in Lethal Prostate Cancer," Cancer Discovery, vol. 11, Issue 5 (May 2021).

Zhang et al., "A Novel Histone Acetyltransferase Inhibitor A485 Improves Sensitivity of Non-Small-Cell Lung Carcinoma Cells to TRAIL," Biochemical Pharmacology, vol. 175: 10 pages (2020).

Zhang-Xu et al., "Current Development of CBP/300 inhibitors in the last decade," European Journal of Medicinal Chemistry, vol. 209: 2-11 (2020).

Zhong et al, "p300 Acetyltransferase Regulates Androgen Receptor Degradation and PTEN-Deficient Prostate Tumorigeneis," Tumor and Stem Cell Biology, Cancer Research, 74(6) (Mar. 5, 2014).

Zhuang et al., "Physiological Activity of Maillard Reaction Products (MRPs) and Technical Measures for Increasing their Production," Liquor-Making, vol. 36, No. 3: 80-83 (May 2009)—Abstract.

Australian Office Action for Application No. 2020360709 dated Oct. 9, 2023.

Canadian Office Action corresponding to CA Application No. 3122354 dated Aug. 17, 2022.

Chinese Office Action in CN Application 202180045103.8, dated Aug. 28, 2024, 7 pages.

International Search Report and Written Opinion corresponding to International Patent Application No. PCT/EP2019/085557 dated Apr. 14, 2020.

International Search Report and Written Opinion corresponding to International Patent Application No. PCT/EP2020/077595 dated Dec. 4, 2020.

International Search Report and Written Opinion of the International Searching Authority issued in International Application No. PCT/EP2021/067346, mailed Aug. 27, 2021, 12 pages.

International Search Report for Application No. PCT/EP2022/059295 dated May 30, 2022.

Japanese Office Action for Application No. 2022520681 dated Oct. 31, 2023.

Mullard, "Cracking KRAS," Nature Reviews Drug Discovery, vol. 18, No. 12: 887-891 (Nov. 2019).

Wu et al., "A chemical toolbox for the study of bromodomains and epigenetic signaling," Nature Communications, vol. 10, No. 1 (Apr. 2019).

European Office Action in EP Application 21733159.4 dated May 31, 2024, 12 pages.

* cited by examiner

HETEROCYCLIC DERIVATIVES, PHARMACEUTICAL COMPOSITIONS AND THEIR USE IN THE TREATMENT OR AMELIORATION OF CANCER

FIELD OF INVENTION

The present invention relates to compounds of formula (I) or salts, solvates, cocrystals, tautomers, or mixtures thereof. Furthermore, the present invention relates to pharmaceutical compositions comprising said compounds. Moreover, the present invention relates to the compounds of formula (I) or the salts, solvates, cocrystals, tautomers, or mixtures thereof or the pharmaceutical compositions for use as a medicament and to the compounds of formula (I) or the salts, solvates, cocrystals, tautomers, or mixtures thereof or the pharmaceutical compositions for use in the treatment or amelioration of cancer. Optionally, the compounds of formula (I) or the salts, solvates, cocrystals, tautomers, or mixtures thereof or the pharmaceutical compositions are administered in combination with a second therapeutic agent, in particular an anti-cancer agent.

BACKGROUND

Cancer is one of the most significant health conditions facing individuals in both developed and developing countries. It has been reported that in the United States alone, one in three people will be afflicted with cancer during their lifetime. Moreover, typically more than half of the patients diagnosed with cancer eventually die as a result of the disease. Although significant progress has been made in the early detection and treatment of certain cancers, other cancers have been more difficult to detect and/or treat.

Oncogenic activation of the MAPK pathway is a signature feature of many human cancers, including melanoma and non-small cell lung cancer (NSCLC). Activated oncogenes can be pharmacologically inhibited using small molecules or antibodies. However, the clinical anti-tumor effect of receptor tyrosine kinase (RTK) inhibitors and other oncogene-targeting inhibitors is not durable. Resistance to these inhibitors usually develops. More specifically, the clinical anti-tumor effect of EGFR inhibitors (EGFRi) is not durable. Resistance to EGFR inhibitors usually develops within 9 to 19 months depending on the therapeutic agent and clinical setting (see Leonetti et al., BJC, 2019, 121, pp. 725-737). Therefore, it is desirable to develop a mode of cancer treatment that would prevent drug resistance in cancer patients.

Furthermore, genetic alterations of cancer cells often affect genes that are important for cell cycle control, proliferation, differentiation and/or signal transduction. Overall, phenotypic, signaling, transcriptional, and metabolic plasticity as well as the acquisition of novel genetic alterations have been found to be a driving factor in the development of resistance to cancer treatment including molecularly targeted inhibitors and immunotherapies (see Boumahdi et al., Nature Reviews Drug Discovery, 2019, 19, pp. 39-56.

The same is, e.g., observed in connection with 'castration resistant' prostate cancer (CRPC). Long term disease control of prostate cancer entails a series of hormonal therapies that suppress androgen receptor (AR) signaling, since prostate cancers are exquisitely dependent upon AR function for survival and progression. However, although AR targeted therapies inhibit tumor growth, disease is rarely eliminated and resistance to therapy is acquired through restored AR function. Acquisition of the CRPC phenotype is mediated via re-activation of the AR pathway. The acetyltransferase p300 directly regulates AR levels and AR signaling activity in prostate cancer cells (Zhong et al., 'p300 acetyltransferase regulates androgen-receptor degradation and PTEN-deficient prostate turn oogenesis,' Cancer Res., Vol. 74, pp. 1870-1880, 2014). Therapeutic modulation of p300 function would therefore target all known adaptive mechanisms which lead to the development of CRPC. Approved therapies and those in clinical studies primarily target only one or other of theses cellular mechanisms. The modulation of p300 function directly provides an opportunity to more broadly modulate AR activity in CRPC than current and other experimental therapeutic strategies. In addition, resistance mechanisms to recently approved agents have been shown to be AR-dependent (Cai, C. et al., (2011) 'Intratumoral de novo steroid synthesis activates androgen receptor in castration-resistant prostate cancer and is up-regulated by treatment with Cypl7AI inhibitors,' Cancer Res., Vol. 71, pp. 6503-6513). Targeting p300/CBP as a therapeutic strategy for lethal PC was validated by J. Welti et al. (Cancer discovery, Mar. 28, 2021, DOI: 10.1158/2159-8290). In particular, it was shown that a small-molecule inhibitor inhibited cell proliferation in PC cell lines and decreased AR and C-MYC regulated gene expression. Modulation of p300 should therefore inhibit resistance to current therapies and potentially provide improved and sustained efficacy and greater clinical utility.

Similarly, it was reported that histone acetyltransferases CBP/p300 are involved in recurrent leukemia-associated chromosomal translocations and are key regulators of cell growth. Therefore, efforts to generate inhibitors of CBP/p300 are of clinical value (S. Picaud et al., "Generation of a Selective Small Molecule Inhibitor of the CBP/p300 Bromodomain for Leukemia Therapy", Cancer Res., 2015, Vol. 75, pp. 5106-5119). It was further reported that a potent and selective CBP inhibitor modulates MYC expression that corresponds with antitumor activity in an AML tumor model and that the same compound impaired FOXP3 expression and Treg function, further suggesting CBP bromodomain inhibition as a novel small molecule approach for cancer immunotherapy (F. A. Romero et al., J. Med. Chem., 2017, 60, pp. 9162-9183).

In common with p300, the CREB (cyclic-AMP response element binding protein) binding protein (CBP) is an acetyltransferase that acts as a transcriptional co-activator in human cells. Both CBP and p300 possess a single bromodomain (BRD) and a lysine acetyltransferase (KAT) domain, which are involved in the post-translational modification and recruitment of histones and non-histone proteins. There is high sequence similarity between CBP and p300 in the conserved functional domains (see Duncan A. Hay et al, JACS 2014, 135, 9308-9319). Modulation of CBP function therefore provides a promising route to the treatment of certain cancers. Accordingly, compounds that can modulate, e.g. inhibit, the function of p300 and/or CBP are of interest in cancer therapy. Tumors which harbor loss of function mutations in CBP become addicted to p300 and are uniquely sensitive to p300 inhibition (see Ogiwara et al. 2016 Cancer Discovery. 6; 430-445). Conversely tumors with mutations in p300 are uniquely sensitive to CBP inhibition. Genetic analysis reveals that up to 15% of both non-small cell and small cell lung tumors have these loss of function mutations. Similar mutations are also found in up to 25% of bladder cancers. Accordingly, compounds that can modulate, e.g. inhibit, the function of p300 and/or CBP are of interest in cancer therapy for tumors with these molecular changes. Furthermore, CBP/p300 regulates the expression of key tumor immune checkpoint proteins such as CTLA4/PD-L1 (see Casey et al., Science. 352; p227-231, 2016) and plays an important role in the differentiation and function of T-regulatory cells which are involved in immune evasion by tumors. Accordingly, compounds that can modulate, e.g. inhibit, the function of p300 and/or CBP are of interest for cancer therapy in combination with agents that target the onco-immune system.

In view of the above, there is a need for compounds targeting p300 and/or CBP. Such compounds are expected to be able to treat cancer and/or to prevent the development of drug resistance.

SUMMARY

It is an object of the present invention to provide compounds, which have activity in modulating, e.g. inhibiting, p300 and CBP function, and accordingly, provide a therapeutic effect in the treatment of cancer and/or the prevention of resistance.

It is another object of the present invention to provide compounds, which are suitable for use as a medicament. It is another object of the present invention to provide compounds, which are suitable for use in the treatment of cancer, preferably selected from melanoma, non-small cell lung cancer, prostate cancer, bile duct cancer, bladder cancer, pancreatic cancer, thyroid cancer, ovarian cancer, colorectal tumor, hairy cell leukemia, acute myeloid leukemia, multiple myeloma, liver cancer, breast cancer, esophageal cancer, head and neck cancer and glioma, in particular selected from multiple myeloma, acute myeloid leukemia, prostate cancer, and non-small cell lung cancer. It is another object of the present invention to provide compounds, which are suitable for use in the prevention of drug resistance in cancer patients, in particular in the prevention of resistance to EGFR inhibitors or in the prevention of resistance to KRAS inhibitors. It is yet another object of the present invention to provide compounds, which can be used in combination with drugs, such as EGFR inhibitors or KRAS inhibitors, and preferably prevent the development of resistance to these drugs. It is yet another object of the present invention to provide compounds, which are suitable for use in the treatment or amelioration of a fibrotic diseases.

At least some of the above objects can be achieved by the compounds of formula (I) or salts, solvates, cocrystals, tautomers, or mixtures thereof as defined herein, or the pharmaceutical compositions comprising the same, and by the medical uses thereof. The inventors of the present invention have surprisingly found that the compounds of formula (I) or the salts, solvates, cocrystals, tautomers, or mixtures thereof have activity in modulating, in particular inhibiting, p300 and CBP function. In preferred embodiments of the invention, the compounds exhibit a selectivity over other bromodomain-containing proteins. In certain particularly preferred embodiments of the invention, the compounds are selective over the BET protein family. Accordingly, the compounds of formula (I) or salts, solvates, cocrystals, tautomers, or mixtures thereof as defined herein, or the pharmaceutical compositions comprising the same, are suitable for use as a medicament, in particular for the treatment of cancer, either alone or in combination with another drug, preferably preventing resistance against said drug.

Thus, in a first aspect, the present invention relates to a compound of formula (I)

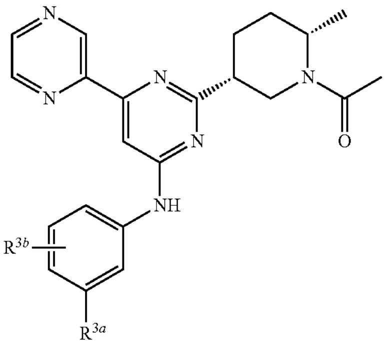

or a pharmaceutically acceptable salt, solvate, cocrystal, tautomer, or a mixture thereof, wherein $R^{3a}$ is a 5-membered heterocyclic ring, wherein the heterocyclic ring comprises one or more, same or different heteroatoms selected from O and N, and wherein each substitutable carbon or heteroatom is independently unsubstituted or substituted with one or more, same or different substituents selected from $C_1$-$C_3$-alkyl and a 4-membered heterocyclic ring, wherein the heterocyclic ring comprises one or more, same or different heteroatoms selected from O, N, or S; $R^{3b}$ is selected from H, F, Cl, and $CH_3$;

and wherein the compound is not any one of:

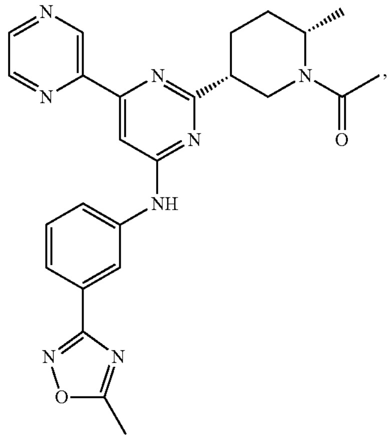

,

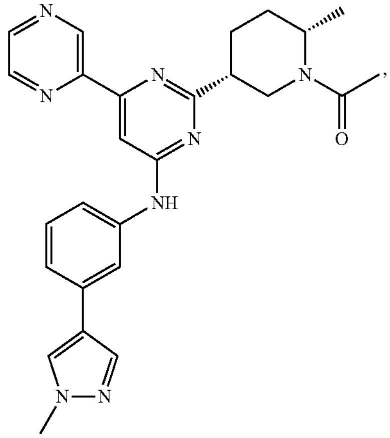

,

-continued

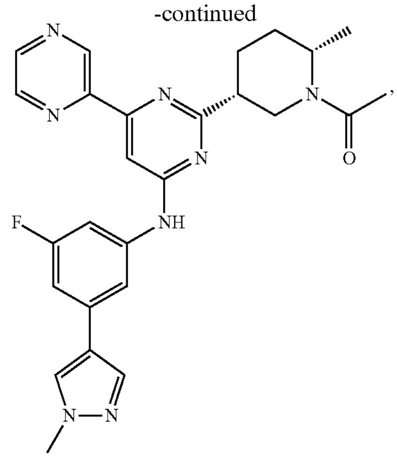

,

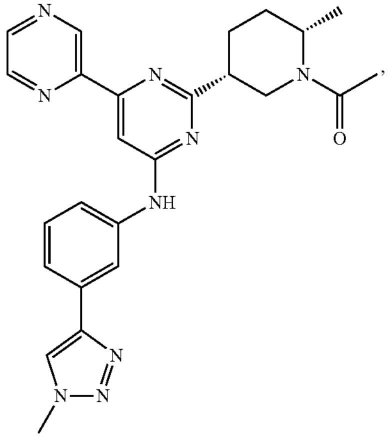

, or

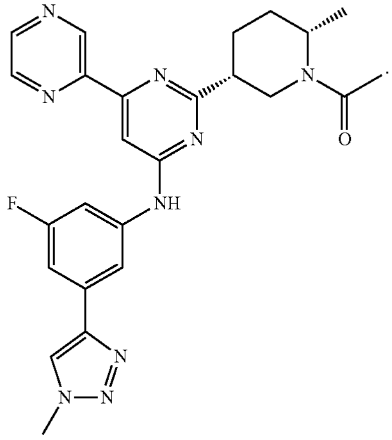 [SMILES: CC(=O)N1C[C@H](c2nc(Nc3cc(F)cc(-c4cn(C)nn4)c3)cc(-c3cnccn3)n2)CC[C@@H]1C]

.

Further embodiments regarding the compound of formula (I) are provided below. In a further aspect, the present invention relates to pharmaceutical composition comprising a pharmaceutically effective amount of the compound of formula (I) or a pharmaceutically acceptable salt, solvate, cocrystal, tautomer, or a mixture thereof as defined above, and optionally a pharmaceutically acceptable carrier, diluent or excipient. Still further optionally, the pharmaceutical composition of the present aspect comprises a KRAS inhibitor. In a related aspect, the present invention relates to a kit comprising (i) a pharmaceutical composition according to the present aspect and (ii) a pharmaceutical composition comprising a KRAS inhibitor.

In yet a further aspect, the present invention relates to a compound of formula (I) or a pharmaceutically acceptable salt, solvate, cocrystal, tautomer, or a mixture thereof as defined above or a pharmaceutical composition as defined above for use in medicine.

In a further aspect, the present invention relates to a compound of formula (I) or a pharmaceutically acceptable salt, solvate, cocrystal, tautomer, or a mixture thereof as defined above or a pharmaceutical composition as defined above for use in the treatment or amelioration of cancer, wherein preferably the cancer is selected from melanoma, non-small cell lung cancer, prostate cancer, bile duct cancer, bladder cancer, pancreatic cancer, thyroid cancer, ovarian cancer, colorectal tumor, hairy cell leukemia, acute myeloid leukemia, multiple myeloma, liver cancer, breast cancer, esophageal cancer, head and neck cancer and glioma, in particular multiple myeloma, acute myeloid leukemia, prostate cancer and non-small cell lung cancer. In one embodiment in this connection, the compound of formula (I) or a pharmaceutically acceptable salt, solvate, cocrystal, tautomer, or a mixture thereof as defined above or the pharmaceutical composition as defined above is used in combination with a second therapeutic agent, wherein preferably said therapeutic agent is an anti-cancer agent.

In a further aspect, the present invention relates to a compound of formula (I) or a pharmaceutically acceptable salt, solvate, cocrystal, tautomer, or a mixture thereof as defined above or a pharmaceutical composition as defined above in combination with an EGFR inhibitor for use in the treatment of a patient suffering from non-small cell lung cancer (NSCLC), wherein the NSCLC exhibits an oncogenic alteration in the EGFR.

In still a further aspect, the present invention relates to a compound of formula (I) or a pharmaceutically acceptable salt, solvate, cocrystal, tautomer, or a mixture thereof as defined above or a pharmaceutical composition as defined above in combination with a KRAS inhibitor for use in the treatment of a patient suffering from cancer, wherein the cancer exhibits an oncogenic alteration in the KRAS. In yet a further aspect, the present invention relates to a compound of formula (I) or a pharmaceutically acceptable salt, solvate, cocrystal, tautomer, or a mixture thereof as defined above or a pharmaceutical composition as defined above for use in the treatment or amelioration of a fibrotic disease, wherein preferably the fibrotic disease is idiopathic pulmonary fibrosis (IPF) or non-alcoholic steatohepatitis (NASH).

DETAILED DESCRIPTION

Unless defined otherwise, all technical and scientific terms used herein have the same meanings as commonly understood by one of ordinary skill in the art to which this invention belongs. The herein described and disclosed embodiments, preferred embodiments and very preferred embodiments should apply to all aspects and other embodiments, preferred embodiments and very preferred embodiments irrespective of whether it is specifically again referred to or its repetition is avoided for the sake of conciseness.

The articles "a" and "an", as used herein, refer to one or to more than one (i.e., to at least one) of the grammatical object of the article. The term "or", as used herein, should be understood to mean "and/or", unless the context clearly indicates otherwise.

The term "preferably" is used to describe features or embodiments which are not required in the present invention but may lead to improved technical effects.

As used herein, the term "about" preferably refers to ±10% of the indicated numerical value, more preferably to ±5% of the indicated numerical value, and in particular to the exact numerical value indicated.

The term "compound(s) of the present invention" is to be understood as equivalent to the term "compound(s) according to the invention", and covers the compound(s) of formula (I) or a salt, solvate, cocrystal, or tautomer or a mixture thereof.

The term "substituted", as used herein, means that a hydrogen atom bonded to a designated atom is replaced with a specified substituent, provided that the substitution results in a stable or chemically feasible compound. Unless otherwise indicated, a substituted atom may have one or more substituents and each substituent is independently selected.

The term "substitutable", when used in reference to a designated atom, means that attached to the atom is a hydrogen, which can be replaced with a suitable substituent.

In connection with the above term "substitutable", in particular with regard to the expression "wherein each substitutable carbon or heteroatom is independently unsubstituted or substituted with one or more, same or different substituents" it is to be understood that this term covers all possible options wherein e.g. carbon and heteroatoms are independently unsubstituted or substituted or wherein e.g. only carbon or only heteroatoms are independently unsubstituted or substituted with one or more, same or different substituents.

When it is referred to certain atoms or moieties being substituted with "one or more" substituents, the term "one or more" is intended to cover at least one substituent, e.g. 1 to 10 substituents, preferably 1, 2, 3, 4, or 5 substituents, more preferably 1, 2, or 3 substituents, most preferably 1, or 2 substituents. When neither the term "unsubstituted" nor "substituted" is explicitly mentioned concerning a moiety, said moiety is to be considered as unsubstituted.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_1$-$C_3$-alkyl" denotes an alkyl group having 1 to 3 carbon atoms. Examples of such an alkyl group are methyl, ethyl, n-propyl, and iso-propyl.

As used herein, the term "heterocyclyl" or "heterocyclic ring" refers to a ring group, including monocyclic rings as well as bridged rings, spiro rings and/or fused ring systems (which may be composed of, e.g., two or three rings), wherein said ring group comprises one or more (such as, e.g., one, two, three, or four) ring heteroatoms independently selected from O, S, and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic.

Unless defined otherwise, "heterocyclyl" preferably refers to heteroaryl, heterocycloalkyl or heterocycloalkenyl. Preferably, the heterocyclic ring is a monocyclic ring. The number of carbon and heteroatoms in the heterocyclic ring may be defined by indicating the number of ring members, i.e. the number of atoms forming the ring (also referred to as "ring atoms"). For example, a 5-membered heterocyclic ring comprises 5 ring atoms, and a 4-membered heterocyclic ring comprises 4 ring atoms.

As used herein, the term "heteroaryl" or "heteroaromatic ring" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). Preferably, the heteroaromatic ring is a monocyclic ring. The number of carbon and heteroatoms in the heteroaromatic ring may be defined by indicating the number of ring members, i.e. the number of atoms forming the ring (also referred to as "ring atoms"). For example, a 5-membered heteroaromatic ring comprises 5 ring atoms. Exemplary 5-membered heteroaromatic rings include pyrrolyl, furanyl, thiophenyl, imidazolyl, pyrazolyl, oxathiolyl, isoxathiolyl, thiazolyl, isothiazolyl, triazolyl, furazanyl, oxadiazolyl, thiadiazolyl, dioxazolyl, dithiazolyl, and tetrazolyl.

A skilled person will appreciate that the substituent groups of the compounds of formula (I) may be attached to the remainder of the respective compound via a number of different positions of the corresponding specific substituent group. Unless defined otherwise, the preferred attachment positions for the various specific substituent groups are as illustrated in the examples.

The scope of the invention embraces salts, in particular pharmaceutically acceptable salts of the compounds of formula (I) which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. It is particularly preferred that the compound of formula (I) is in the form of a sodium salt. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. Preferred pharmaceutically acceptable salts of the compounds of formula (I) include a hydrochloride salt, a hydrobromide salt, a mesylate salt, a sulfate salt, a tartrate salt, a fumarate salt, an acetate salt, a citrate salt, and a phosphate salt. A particularly preferred pharmaceutically acceptable salt of the compound of formula (I) is a hydrochloride salt. Accordingly, it is preferred that the compound of formula (I), including any one of the specific compounds of formula (I) described herein, is in the form of a hydrochloride salt, a hydrobromide salt, a mesylate salt, a sulfate salt, a tartrate salt, a fumarate salt, an acetate salt, a citrate salt, or a phosphate salt, and it is particularly preferred that the compound of formula (I) is in the form of a hydrochloride salt.

In connection with base addition salts of the compounds of formula (I), it is noted that the nitrogen atom (i.e. the hydrogen atom attached to said nitrogen atom) bridging the phenyl ring of the core structure with the remainder of the core structure is acidic. Accordingly, deprotonation is possible, so that a base addition salt, e.g. a sodium salt can be formed. In preferred embodiments of the invention, preferred salts of the compounds of formula (I) therefore include base addition salts, in particular sodium salts.

In connection with acid addition salts of the compounds of formula (I), it is noted that the nitrogen atoms of the core structure are typically not basic enough for the formation of acid addition salts. However, if, e.g., the substituent $R^{3a}$ carries a basic nitrogen atom, such as in case of $R^{3a}$ being an imidazole ring, protonation is possible, so that an acid addition salt, e.g., a hydrochloride salt, can be formed. In certain embodiments of the invention, preferred salts of the compounds of formula (I) therefore include acid addition salts, in particular hydrochloride salts.

A “solvate” refers to an association or complex of one or more solvent molecules and the compound of formula (I). Examples of solvents that form solvates include, but are not limited to, water, isopropanol, ethanol, methanol, dimethyl sulfoxide (DMSO), ethyl acetate, acetic acid, acetonitril, and ethanolamine. The term “hydrate” refers to the complex where the solvent molecule is water. It is to be understood that such solvates of the compounds of the formula (I) also include solvates of pharmaceutically acceptable salts of the compounds of the formula (I).

A “cocrystal” refers to a crystalline structure that contains at least two different compounds that are solid in their pure form under ambient conditions. Cocrystals are made from neutral molecular species, and all species remain neutral after crystallization; further, typically and preferably, they are crystalline homogeneous phase materials where two or more building compounds are present in a defined stoichiometric ratio. See hereto Wang Y and Chen A, 2013; and Springuel G R, et al., 2012; and U.S. Pat. No. 6,570,036.

The compounds of formula (I) have a defined stereochemistry. The present invention encompasses tautomers of the compounds of formula (I), e.g. imine-enamine tautomers.

The compounds of formula (I) may be amorphous or may exist in one or more different crystalline states (polymorphs), which may have different macroscopic properties such as stability or show different biological properties such as activities. The present invention relates to amorphous and crystalline forms of compounds of formula (I), mixtures of different crystalline states of the compounds of formula (I), as well as amorphous or crystalline salts thereof. The scope of the invention also embraces compounds of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^{2}H$; also referred to as “D”). Accordingly, the invention also embraces compounds of formula (I) which are enriched in deuterium. Naturally occurring hydrogen is an isotopic mixture comprising about 99.98 mol-% hydrogen-1 ($^{1}H$) and about 0.0156 mol-% deuterium ($^{2}H$ or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water ($D_2O$).

Further suitable deuteration techniques are described in: Atzrodt J et al., Bioorg Med Chem, 20(18), 5658-5667, 2012; William J S et al., Journal of Labelled Compounds and Radiopharmaceuticals, 53(11-12), 635-644, 2010; Modvig A et al., J Org Chem, 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or 1H hydrogen atoms in the compounds of formula (I) is preferred.

The present invention also embraces compounds of formula (I), in which one or more atoms are replaced by a positron-emitting isotope of the corresponding atom, such as, e.g., $^{18}F$, $^{11}C$, $^{13}N$, $^{15}O$, $^{76}Br$, $^{77}Br$, $^{120}I$ and/or $^{124}I$. Such compounds can be used as tracers or imaging probes in positron emission tomography (PET). The invention thus includes (i) compounds of formula (I), in which one or more fluorine atoms (or, e.g., all fluorine atoms) are replaced by $^{18}F$ atoms, (ii) compounds of formula (I), in which one or more carbon atoms (or, e.g., all carbon atoms) are replaced by $^{11}C$ atoms, (iii) compounds of formula (I), in which one or more nitrogen atoms (or, e.g., all nitrogen atoms) are replaced by $^{13}N$ atoms, (iv) compounds of formula (I), in which one or more oxygen atoms (or, e.g., all oxygen atoms) are replaced by $^{15}O$ atoms, (v) compounds of formula (I), in which one or more bromine atoms (or, e.g., all bromine atoms) are replaced by $^{76}Br$ atoms, (vi) compounds of formula (I), in which one or more bromine atoms (or, e.g., all bromine atoms) are replaced by $^{77}Br$ atoms, (vii) compounds of formula (I), in which one or more iodine atoms (or, e.g., all iodine atoms) are replaced by $^{120}I$ atoms, and (viii) compounds of formula (I), in which one or more iodine atoms (or, e.g., all iodine atoms) are replaced by $^{124}I$ atoms. In general, it is preferred that none of the atoms in the compounds of formula (I) are replaced by specific isotopes.

The term “pharmaceutically acceptable excipient” as used herein refers to compounds commonly comprised in pharmaceutical compositions, which are known to the skilled person. Examples of suitable excipients are exemplary listed below. Typically, a pharmaceutically acceptable excipient can be defined as being pharmaceutically inactive.

Preferred embodiments of the invention are defined hereinafter.

As indicated above, the present invention relates in one aspect to a compound of formula (I)

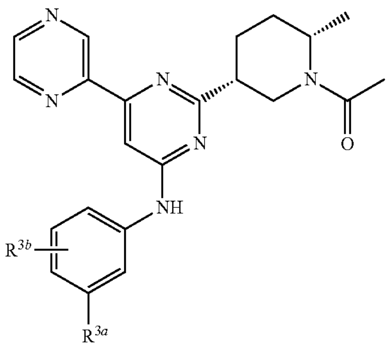

(I)

or a pharmaceutically acceptable salt, solvate, cocrystal, tautomer, or a mixture thereof, wherein $R^{3a}$ is a 5-membered heterocyclic ring, wherein the heterocyclic ring comprises one or more, same or different heteroatoms selected from O and N, and wherein each substitutable carbon or heteroatom is independently unsubstituted or substituted with one or more, same or different substituents selected from $C_1$-$C_3$-alkyl and a 4-membered heterocyclic ring, wherein the heterocyclic ring comprises one or more, same or different heteroatoms selected from O, N, or S;

$R^{3b}$ is selected from H, F, Cl, and $CH_3$;

and wherein the compound is not any one of:

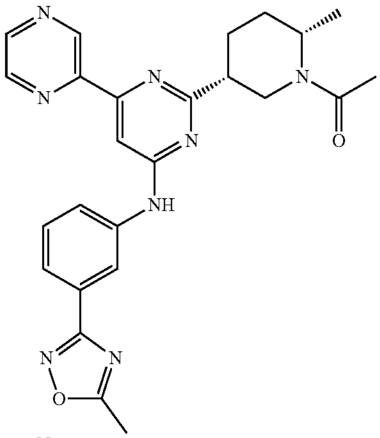

,

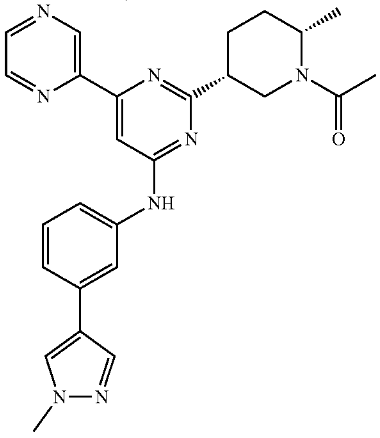

,

-continued

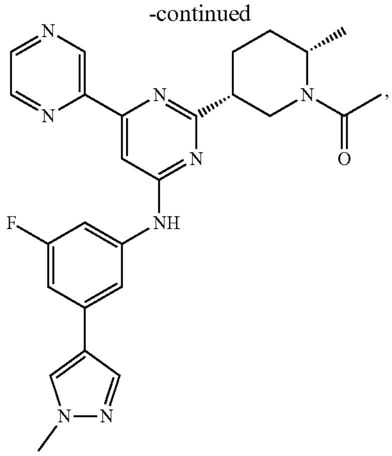

,

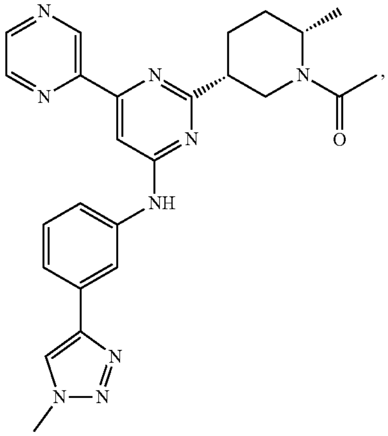

, or

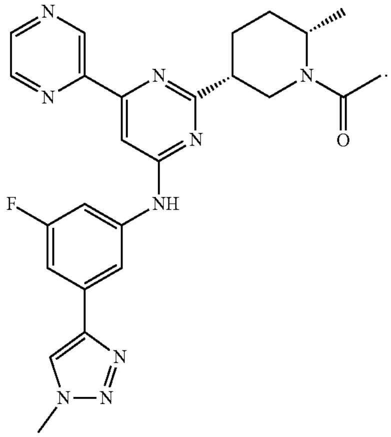 [SMILES: CC(=O)N1C[C@H](c2nc(Nc3cc(F)cc(-c4cn(C)nn4)c3)cc(-c3cnccn3)n2)CC[C@@H]1C]

.

In one embodiment, the present invention relates to a compound of formula (I) or a pharmaceutically acceptable salt, solvate, cocrystal, tautomer, or a mixture thereof, wherein the compound is not any one of:

-continued
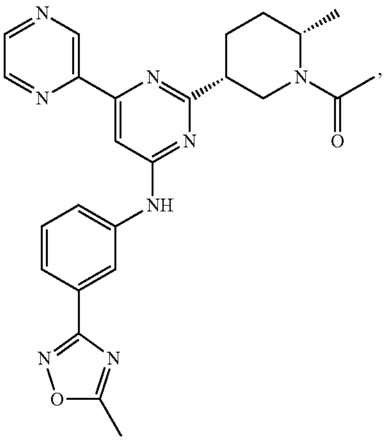
,
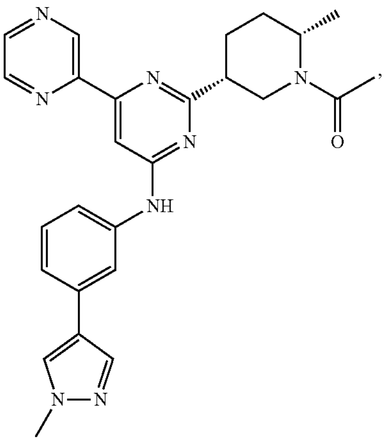
,
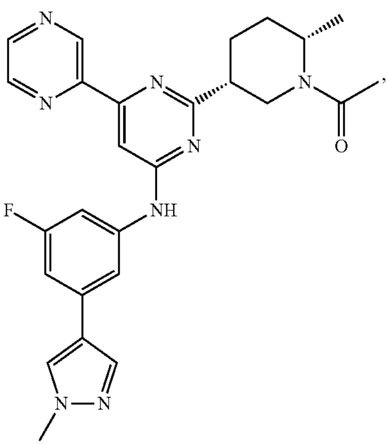 [SMILES: CC(=O)N1C[C@H](c2nc(Nc3cc(F)cc(-c4cn(C)nn4)c3)cc(-c3cnccn3)n2)CC[C@@H]1C]
,
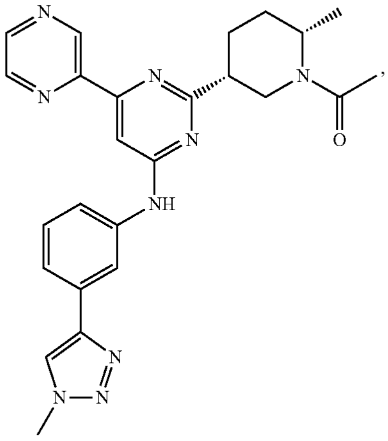
, or
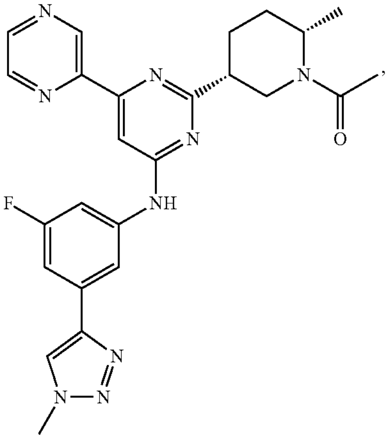
,
or a salt thereof.
In one embodiment, the present invention relates to a compound of formula (I) or a pharmaceutically acceptable salt, solvate, cocrystal, tautomer, or a mixture thereof, wherein the compound
is not any one of:
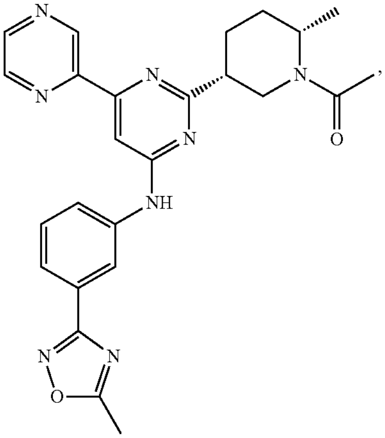
, -continued

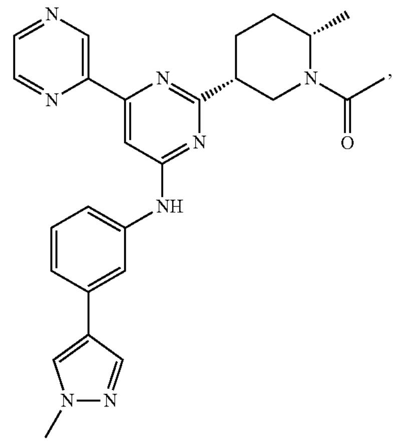

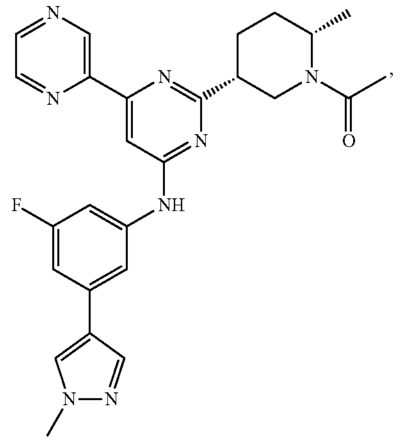

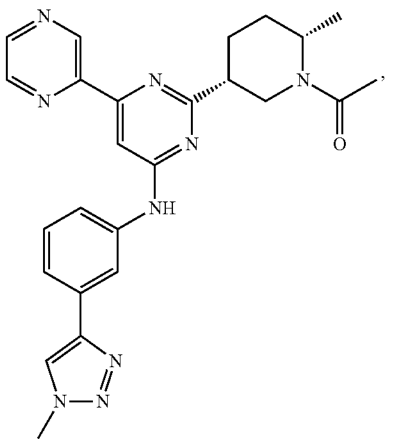

or

-continued

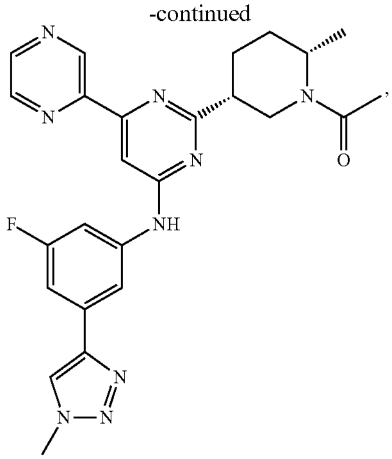

or a salt, solvate, cocrystal, tautomer, or mixture thereof.

In one embodiment, the present invention relates to a compound of formula (I) or a pharmaceutically acceptable salt, solvate, cocrystal, tautomer, or a mixture thereof, wherein $R^{3a}$ is a 5-membered heteroaryl ring, wherein the heteroaryl ring comprises one or more, same or different heteroatoms selected from O and N, and wherein each substitutable carbon or heteroatom is independently unsubstituted or substituted with one or more, same or different substituents selected from $CH_3$ and oxetanyl.

In a preferred embodiment, $R^{3a}$ is selected from the group consisting of imidazolyl, triazolyl, and oxadiazolyl, wherein each substitutable carbon or heteroatom is independently unsubstituted or substituted with one or more, same or different substituents selected from $CH_3$ and oxetanyl.

In another embodiment, the present invention relates to a compound of formula (I) or a pharmaceutically acceptable salt, solvate, cocrystal, tautomer, or a mixture thereof, wherein $R^{3b}$ is selected from H, F, and $CH_3$.

In a preferred embodiment, the present invention relates to a compound of formula (I) or a pharmaceutically acceptable salt, solvate, cocrystal, tautomer, or a mixture thereof, wherein the compound of formula (I) is selected from the group consisting of

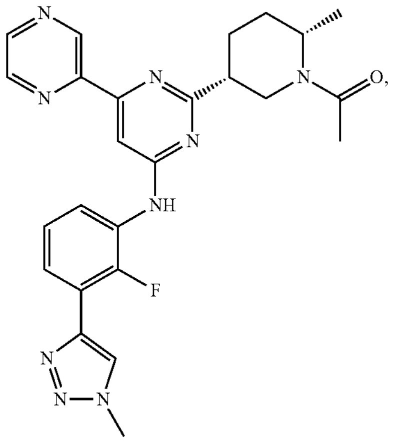

-continued

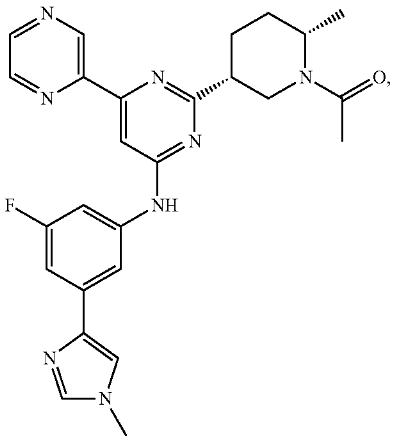

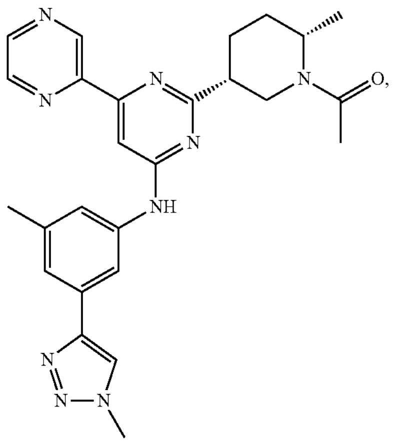

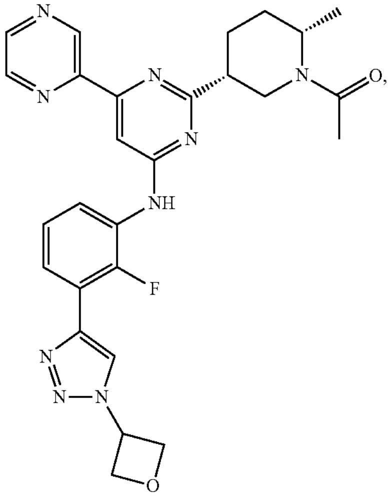

and

-continued

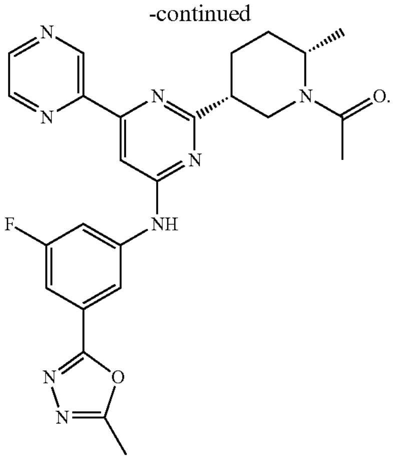

In one particularly preferred embodiment, the present invention relates to a compound of formula (I) or a pharmaceutically acceptable salt, solvate, cocrystal, tautomer, or a mixture thereof, wherein the compound of formula (I) is

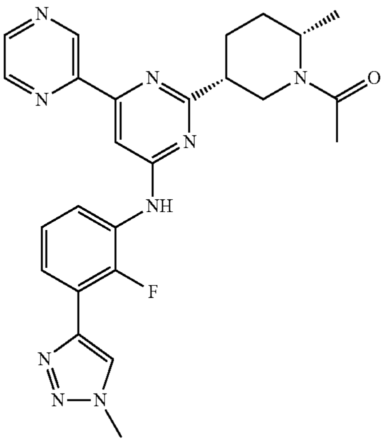 [SMILES: CC(=O)N1C[C@H](c2nc(Nc3cccc(-c4cn(C)nn4)c3F)cc(-c3cnccn3)n2)CC[C@@H]1C]

In another particularly preferred embodiment, the present invention relates to a compound of formula (I) or a pharmaceutically acceptable salt, solvate, cocrystal, tautomer, or a mixture thereof, wherein the compound of formula (I) is

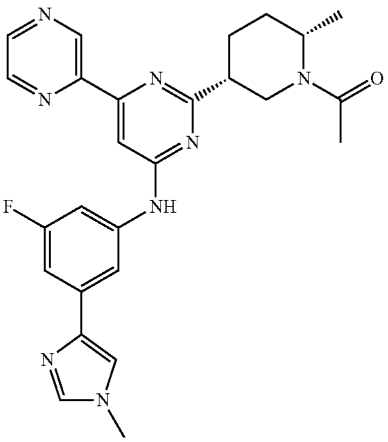 [SMILES: CC(=O)N1C[C@H](c2nc(Nc3cc(F)cc(-c4cn(C)cn4)c3)cc(-c3cnccn3)n2)CC[C@@H]1C]

In another particularly preferred embodiment, the present invention relates to a compound of formula (I) or a pharmaceutically acceptable salt, solvate, cocrystal, tautomer, or a mixture thereof, wherein the compound of formula (I) is

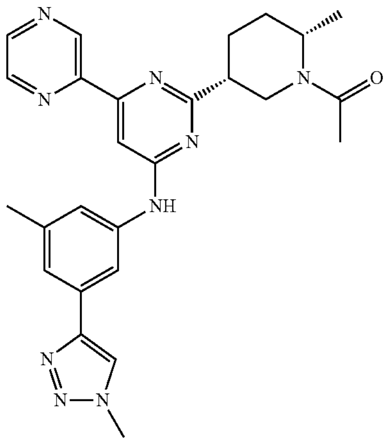 [SMILES: CC(=O)N1C[C@H](c2nc(Nc3cc(C)cc(-c4cn(C)nn4)c3)cc(-c3cnccn3)n2)CC[C@@H]1C]

In another particularly preferred embodiment, the present invention relates to a compound of formula (I) or a pharmaceutically acceptable salt, solvate, cocrystal, tautomer, or a mixture thereof, wherein the compound of formula (I) is

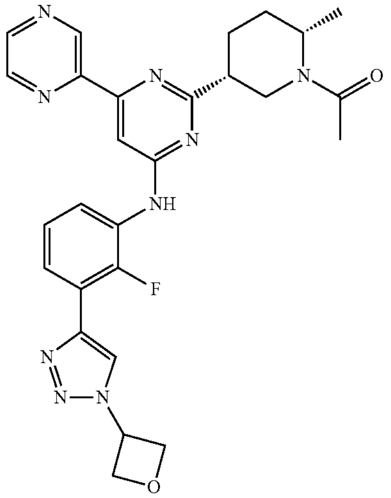 [SMILES: CC(=O)N1C[C@H](c2nc(Nc3cccc(-c4cn(C5COC5)nn4)c3F)cc(-c3cnccn3)n2)CC[C@@H]1C]

In another particularly preferred embodiment, the present invention relates to a compound of formula (I) or a pharmaceutically acceptable salt, solvate, cocrystal, tautomer, or a mixture thereof, wherein the compound of formula (I) is

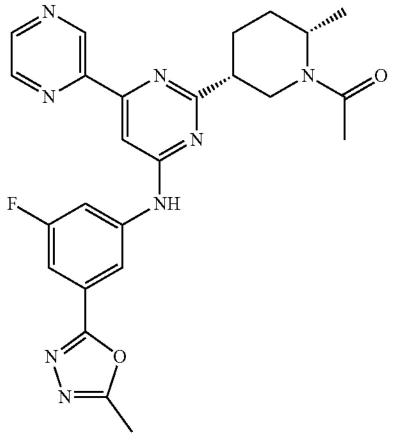 [SMILES: CC(=O)N1C[C@H](c2nc(Nc3cc(F)cc(-c4nnc(C)o4)c3)cc(-c3cnccn3)n2)CC[C@@H]1C]

In yet another particularly preferred embodiment, the present invention relates to a compound of formula (I) in the form of a sodium salt, wherein the sodium salt of the compound of formula (I) has the following structure:

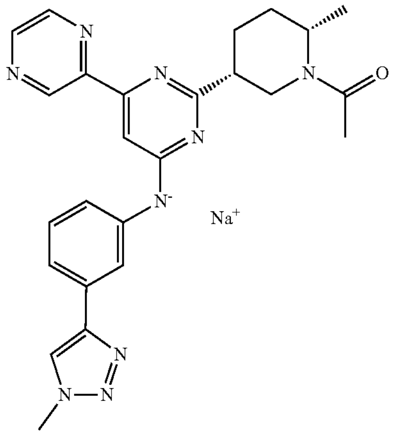 [SMILES: CC(=O)N1C[C@H](c2nc([N-]c3cccc(-c4cn(C)nn4)c3)cc(-c3cnccn3)n2)CC[C@@H]1C ; [Na+]]

The compounds of the present invention preferably inhibit multiple myeloma cell proliferation and/or survival measured indirectly by metabolic activity of OPM2 cells with an EC50 of 1000 nM or less, preferably 500 nM or less, more preferably 100 nM or less, even more preferably 50 nM or less, especially preferably 10 nM or less. This interference with OPM2 proliferation is an established phenomenon triggered by CBP/p300 bromodomain inhibition and correlates well with compound's CBP/p300 bromodomain inhibition. (Raisner; Cell Reports, 2018, 24, pp. 1722-1729, https://doi.org/10.1016/j.celrep.2018.07.041; own data).

The compounds of the present invention preferably bind to the bromodomains of p300 and CBP. In one embodiment, the compounds of the present invention bind to the bromodomain of p300 and the bromodomain of CBP and are active with an EC50 of 1000 nM or less, preferably 500 nM or less, more preferably 100 nM or less, even more preferably 50 nM or less, especially preferably 10 nM or less. The present invention further relates to a pharmaceutical composition comprising the compound of the present invention and optionally one or more pharmaceutically acceptable excipient(s) and/or carriers.

The type of cancer that can be treated with the compounds and compositions of the present invention is typically selected from non-melanoma skin cancer, esophagogastric adenocarcinoma, glioblastoma, bladder cancer, bladder urothelial carcinoma, esophagogastric cancer, melanoma, non-small cell lung cancer, endometrial cancer, cervical adenocarcinoma, esophageal squamous cell carcinoma, breast cancer, head and neck squamous cell carcinoma, germ cell tumor, small cell lung cancer, ovarian cancer, soft tissue sarcoma, hepatocellular carcinoma, colorectal adenocarcinoma, cervical squamous cell carcinoma, cholangiocarcinoma, prostate cancer, upper tract urothelial carcinoma, diffuse glioma, colorectal cancer, ampullary carcinoma, adrenocortical carcinoma, head and neck cancer, renal clear cell carcinoma, hepatobiliary cancer, glioma, non-Hodgkin lymphoma, mesothelioma, salivary gland cancer, renal non-clear cell carcinoma, miscellaneous neuroepithelial tumor, pheochromocytoma, thymic tumor, multiple myeloma, renal cell carcinoma, bone cancer, pancreatic cancer, leukemia, peripheral nervous system tumors, thyroid cancer, B-lymphoblast leukemia, monoclonal B-cell lymphocytosis, lymphoma, hairy cell leukemia, acute myeloid leukemia, Wilms tumor in particular melanoma and non-small cell lung cancer, in particular melanoma and non-small cell lung cancer. The above diseases typically exhibit a mutation incidence of more than 3% of RTKs (EGFR, ERBB2, ERBB3, ERBB4, PDGFA, PDGFB, PDGFRA, PDGFRB, KIT, FGF1, FGFR1, IGF1, IGFR, VEGFA, VEGFB, KDR) and/or MAPK pathway members (KRAS, HRAS, BRAF, RAF1, MAP3K1/2/3/4/5, MAP2K1/2/3/4/5, MAPK1/3/4/6/7/8/9/12/14, DAB, RASSF1, RAB25).

In a further embodiment, the tumor may be adrenocortical carcinoma, astrocytoma, basal cell carcinoma, carcinoid, cardiac, cholangiocarcinoma, chordoma, chronic myeloproliferative neoplasms, craniopharyngioma, ductal carcinoma in situ, ependymoma, intraocular melanoma, gastrointestinal carcinoid tumor, gastrointestinal stromal tumor (GIST), gestational trophoblastic disease, glioma, histiocytosis, leukemia {e.g., acute lymphoblastic leukemia (ALL), acute myeloid leukemia (AML), chronic lymphocytic leukemia (CLL), chronic myelogenous leukemia (CML), hairy cell leukemia, myelogenous leukemia, myeloid leukemia), lymphoma (e.g., Burkitt lymphoma [non-Hodgkin lymphoma], cutaneous T-cell lymphoma, Hodgkin lymphoma, mycosis fungoides, Sezary syndrome, AIDS-related lymphoma, follicular lymphoma, diffuse large B-cell lymphoma), melanoma, merkel cell carcinoma, mesothelioma, myeloma (e.g., multiple myeloma), myelodysplastic syndrome, papillomatosis, paraganglioma, pheochromacytoma, pleuropulmonary blastoma, retinoblastoma, sarcoma (e.g., Ewing sarcoma, Kaposi sarcoma, osteosarcoma, rhabdomyosarcoma, uterine sarcoma, vascular sarcoma), Wilms' tumor, and/or cancer of the adrenal cortex, anus, appendix, bile duct, bladder, bone, brain, breast, bronchus, central nervous system, cervix, colon, endometrium, esophagus, eye, fallopian tube, gall bladder, gastrointestinal tract, germ cell, head and neck, heart, intestine, kidney (e.g., Wilms' tumor), larynx, liver, lung (e.g., non-small cell lung cancer, small cell lung cancer), mouth, nasal cavity, oral cavity, ovary, pancreas, rectum, skin, stomach, testes, throat, thyroid, penis, pharynx, peritoneum, pituitary, prostate, rectum, salivary gland, ureter, urethra, uterus, vagina, vulva, or acoustic neuroma, acute leukemia, acute lymphocytic leukemia, acute myelocytic leukemia, acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer (NSCLC), oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, s)movioma, sweat gland carcinoma, thyroid cancer, Waldenstrom's macroglobulinemia, testicular tumors, uterine cancer, or Wilms' tumor.

The tumor may also be a tumor which is dependent on androgen receptor (AR) signaling or which overexpresses c-Myc, or in cancers in which there is activation of CBP and/or p300 function. The cancers that can be treated include those which express AR or are otherwise associated with AR, those that harbour loss of function mutations in CBP or p300 and those which have activated CBP and/or p300. Cancers that may be treated include, but are not restricted to, prostate cancer, breast cancer, bladder cancer, lung cancer, lymphoma and leukaemia. The prostate cancer may be, for instance, castration-resistant prostate cancer (CRPC). The lung cancer may be, for instance, non-small cell lung cancer or small cell lung cancer.

In particular, the present invention relates to a compound of the present invention or a pharmaceutical composition of the invention for use in the treatment or amelioration of cancer, wherein preferably the cancer is selected from melanoma, non-small cell lung cancer, prostate cancer, bile duct cancer, bladder cancer, pancreatic cancer, thyroid cancer, ovarian cancer, colorectal tumor, hairy cell leukemia, acute myeloid leukemia, multiple myeloma, liver cancer, breast cancer, esophageal cancer, head and neck cancer and glioma, in particular multiple myeloma, acute myeloid leukemia, prostate cancer and non-small cell lung cancer.

The present invention further relates to a compound of the present invention or a pharmaceutical composition of the invention for use as indicated above, wherein the compound of the present invention or the pharmaceutical composition of the invention is used in combination with a second therapeutic agent, and wherein preferably said therapeutic agent is an anti-cancer agent.

The present invention further relates to a method of treating or ameliorating cancer, wherein preferably the cancer is selected from melanoma, non-small cell lung cancer, prostate cancer, bile duct cancer, bladder cancer, pancreatic cancer, thyroid cancer, ovarian cancer, colorectal tumor, hairy cell leukemia, acute myeloid leukemia, multiple myeloma, liver cancer, breast cancer, esophageal cancer, head and neck cancer and glioma, in particular multiple myeloma, acute myeloid leukemia, prostate cancer and non-small cell lung cancer, the method comprising administering to a patient in need thereof a therapeutically effective amount of the compound of the present invention or the pharmaceutical composition of the invention.

The present invention also relates to a method of treating or ameliorating cancer by preventing or delaying drug resistance, the method comprising administering to a patient in need thereof a therapeutically effective amount of the compound of the present invention or the pharmaceutical composition of the invention. Furthermore, the present invention relates to the use of the compound of the present invention or the pharmaceutical composition of the invention for the manufacture of a medicament for the treatment or amelioration of cancer. Furthermore, the present invention relates to the use of the compound of the present invention or the pharmaceutical composition of the invention for the manufacture of a medicament for the treatment or amelioration of cancer by preventing or delaying drug resistance.

Embodiments relating to non-small cell lung cancer (NSCLC) The present invention in an aspect also relates to a compound of the present invention or a pharmaceutical composition of the invention in combination with an EGFR inhibitor for use in the treatment of a patient suffering from NSCLC, wherein the NSCLC exhibits an oncogenic alteration in the EGFR. This aspect may also be referred to as a compound of the present invention or a pharmaceutical composition of the invention in combination with an EGFR inhibitor for use in the treatment of a patient suffering from NSCLC, wherein the NSCLC is characterized by the EGFR-mutational profile given in the one or more indications of the label of the EGFR inhibitor used in the combination or wherein the NSCLC is characterized by the EGFR-mutational profile targeted in the clinical trial setting by the EGFR inhibitor used in the combination.

In a preferred embodiment of this aspect, the oncogenic alteration in the EGFR results in overactivation of the EGFR. The oncogenic alteration in the EGFR may even result in constitutively active EGFR (in the meaning that the enzymatic activity of the EGFR, namely the protein-kinase activity, is constitutively active). In a further preferred embodiment of this aspect, the oncogenic alteration in the EGFR is caused by a deletion and/or insertion in exon 18 or in exon 19 or in exon 20 of the EGFR gene; a kinase domain duplication in the EGFR gene; an amplification of the EGFR gene; at least one base mutation in the EGFR gene resulting in an amino acid substitution in the EGFR selected from the group consisting of L858R, G719S, G719A, G719C, V765A, T783A, S7681, S768V, L861Q, E709X, L819Q, A750P and combinations thereof; and combinations of any of the foregoing. It can be preferred that the oncogenic alteration is caused by a deletion in exon 19 of the EGFR gene; an insertion in exon 20 of the EGFR gene; at least one base mutation in the EGFR gene resulting in an amino acid substitution in the EGFR selected from the group consisting of L858R, G719S, G719A, G719C, V765A, T783A, S7681, S768V, L861Q, E709X, L819Q, A750P and combinations thereof; and combinations of any of the foregoing. It can also be preferred that the oncogenic alteration is caused by a deletion in exon 19 of the EGFR gene; at least one base mutation in the EGFR gene resulting in the amino acid substitution L858R in the EGFR; and combinations thereof. A deletion and insertion in exon 18 of the EGFR gene is in particular a deletion resulting in the deletion of E709-T710 in the EGFR and an insertion of D at this position in the EGFR. A deletion in exon 19 of the EGFR gene is in particular a deletion resulting in the deletion of E746-A750 or L747-E749 in the EGFR. A deletion and insertion in exon 19 of the EGFR is in particular a deletion resulting in the deletion of L747-A750 in the EGFR and an insertion of P at this position in the EGFR or a deletion resulting in the deletion of L747-T751 in the EGFR and an insertion of S at this position in the EGFR. An insertion in exon 20 of the EGFR gene is in particular an insertion resulting in the insertion of an amino acid (in the meaning of any amino acid or X) at a position in the EGFR between two amino acids selected from the group consisting of D761-E762, A763-Y764, Y764-V765, A767-S768, S768-V769, V769-D770, D770-N771, N771-P772, P772-H773, H773-V774, V774-C775, V765-M766, and combinations thereof. It can be most preferred that the oncogenic alteration is caused by a deletion in exon 19 of the EGFR gene (in particular a deletion resulting in the deletion of E746-A750 or L747-E749 in the EGFR); at least one base mutation in the EGFR gene resulting in the amino acid substitution L858R or A750P in the EGFR; and combinations thereof. It can also be very preferred that the oncogenic alteration is caused by a deletion in exon 19 of the EGFR gene or at least one base mutation in the EGFR gene resulting in the amino acid substitution L858R in the EGFR. When reference is made herein to "X" as an amino acid, "X" indicates any amino acid (but of course an amino acid differing from the wild-type amino acid at the respective position, if applicable, e.g. for E709X).

In an embodiment of this aspect, the NSCLC does not additionally exhibit a resistance alteration in the EGFR. Accordingly, a compound of the present invention or a pharmaceutical composition of the invention in combination with an EGFR inhibitor for the present use would be used as first-line treatment, and the EGFR inhibitor in the combination may be any EGFR inhibitor that is administered (or indicated) for treating NSCLC exhibiting an oncogenic alteration in the EGFR.

In another embodiment of this aspect, the NSCLC additionally exhibits a resistance alteration in the EGFR. The resistance alteration in the EGFR may in particular be caused by at least one base mutation in the EGFR gene resulting in an amino acid substitution in the EGFR selected from the group consisting of T790M, C797X (mainly C797S), L792X, G796X, L718Q, L718V, G724S, D761Y, V834L, T854A, and combinations thereof. It can be preferred that the resistance alteration in the EGFR is caused by at least one base mutation in the EGFR gene resulting in an amino acid substitution in the EGFR selected from the group consisting of T790M, C797X (mainly C797S), L718Q, L718V, T854A, and combinations thereof. Most preferred is that the resistance alteration in the EGFR is caused by at least one base mutation in the EGFR gene resulting in the amino acid substitution T790M in the EGFR. When reference is made herein to "X" as an amino acid, "X" indicates any amino acid (but of course an amino acid differing from the wild-type amino acid at the respective position, if applicable, e.g. for C797X).

When the NSCLC additionally exhibits a resistance alteration in the EGFR, the patient was previously treated with a (first) EGFR inhibitor that was effective initially and then became ineffective due to the development of resistance, in particular due to development of an EGFR resistance alteration. It is important to understand that in the combination for use of the present invention, the EGFR inhibitor in such a scenario is not the (first) EGFR inhibitor administered previously, but a (second or third) EGFR inhibitor that is initially therapeutically effective despite the at least one resistance alteration when administered alone. We refer to an "initial therapeutic effectiveness" here as it is a common observation that yet a further resistance towards this (second or third) EGFR inhibitor develops, rendering this (second or third) EGFR inhibitor ultimately also ineffective. In such a scenario, the combination for use of the present invention would be used as second-line or third-line treatment. To give an example, gefitinib may have been administered (alone as first-line treatment) previously to a patient suffering from NSCLC exhibiting an oncogenic alteration, with the gefitinib treatment becoming ineffective over time (typically after a period of about to about 12 months) and with the finding (e.g. via a biopsy and a corresponding test in order to detect EGFR mutations) that the EGFR T790M resistance alteration developed in the tumor during the gefitinib-treatment. In such a situation, gefitinib would not be used in the combination for use of the present invention, but in particular osimertinib that has been shown (and is indicated) to be effective in the treatment of patients with EGFR T790M mutation-positive NSCLC, whose disease has progressed on or after EGFR tyrosine kinase inhibitor (TKI) therapy.

Taking the above into account, the present invention in an embodiment relates to a compound of the present invention or a pharmaceutical composition of the invention in combination with an EGFR inhibitor for use in the treatment of a patient suffering from NSCLC, wherein the NSCLC exhibits an oncogenic alteration in the EGFR, with the proviso that, if the NSCLC additionally exhibits a resistance alteration in the EGFR due to previous administration of an EGFR inhibitor, the EGFR inhibitor of the combination is not the EGFR inhibitor previously administered but in particular an EGFR inhibitor, which is therapeutically effective despite the resistance alteration in the EGFR (namely the resistance alteration that rendered the previously administered EGFR inhibitor therapeutically ineffective). One may also refer to a compound of the present invention or a pharmaceutical composition of the invention in combination with an EGFR inhibitor for use according to this aspect of the present invention with the proviso that, if the NSCLC additionally exhibits a resistance alteration in the EGFR due to previous administration of an EGFR inhibitor, the EGFR inhibitor of the combination is not the EGFR inhibitor previously administered but an EGFR inhibitor which is therapeutically effective during the first treatment cycles if administered alone despite the resistance alteration or with the proviso that, if the NSCLC additionally exhibits a resistance alteration in the EGFR due to previous administration of an EGFR inhibitor, the EGFR inhibitor of the combination is not the EGFR inhibitor previously administered but an EGFR inhibitor that is indicated for treatment of NSCLC additionally exhibiting the resistance alteration in the EGFR.

To give examples when considering two specific EGFR inhibitors (namely "X" and "the EGFR inhibitor of the combination"), the above paragraph is understood to refer in an embodiment to a compound of the present invention or a pharmaceutical composition of the invention in combination with an EGFR inhibitor for use in the treatment of a patient suffering from NSCLC, wherein the NSCLC exhibits an oncogenic alteration in the EGFR, with the proviso that, if the NSCLC additionally exhibits a resistance alteration in the EGFR due to previous administration of EGFR inhibitor X, the EGFR inhibitor of the combination is not EGFR inhibitor X. It is noted that the EGFR inhibitor of the combination is therapeutically effective despite the resistance alteration in the EGFR (namely the resistance alteration that rendered the previously administered EGFR inhibitor X therapeutically ineffective).

In another embodiment of this aspect, the EGFR inhibitor is a small molecule inhibitor or an antibody. Thus, in such an embodiment, the EGFR inhibitor is not a nucleic acid-based inhibitor, such as e.g. a shRNA or RNAi directed to EGFR. In yet another embodiment of the first aspect, the EGFR inhibitor is a small molecule inhibitor. In a further embodiment of the first aspect, the EGFR inhibitor inhibits the tyrosine kinase activity of the EGFR.

The EGFR inhibitor may be selected from the group consisting of ABBV-321, abivertinib, afatinib, AFM24, alflutinib (AST2818), almonertinib (HS-10296), apatinib, ASK120067, avitinib (ACO0010), AZD3759, BBT-176, BTDX-1535, BLU-451, BLU-701, BLU-945, brigatinib, CK-101 (RX-518), CLN-081 (TAS6417), CM93, D 0316, D 0317, D 0318, dacomitinib, DZD9008, EMB-01, erlotinib, FCN-411, gefitinib, icotinib, keynatinib, lapatinib, lazertinib, MCLA-129, MRG003, mobocertinib, nazartinib, neratinib, olafertinib, osimertinib, poziotinib, pyrotinib, rezivertinib, SH-1028 (oritinib), sutetinib, TAS2940, TAS6417, vandetanib, varlitinib, XZP-5809, amivantamab, CDP1, cetuximab, GC1118, HLX07, JMT101, M1231, necitumumab, nimotuzumab, matuzumab, panitumumab, SCT200, SI-B001, SYN004, Z650, zalutumumab, ZN-e4, ZZ06, and combinations thereof. The EGFR inhibitor may alternatively be selected from the group consisting of ABBV-321, abivertinib, afatinib, alflutinib, almonertinib, apatinib, AZD3759, brigatinib, D 0316, D 0317, D 0318, dacomitinib, DZD9008, erlotinib, FCN-411, gefitinib, icotinib, lapatinib, lazertinib, mobocertinib, nazartinib, neratinib, olafertinib, osimertinib, poziotinib, pyrotinib, rezivertinib, TAS6417, vandetanib, varlitinib, XZP-5809, amivantamab, CDP1, cetuximab, GC1118, HLX07, JMT101, M1231, necitumumab, nimotuzumab, matuzumab, panitumumab, SCT200, SI-B001, SYN004, zalutumumab, and combinations thereof. In a preferred embodiment, the EGFR inhibitor is selected from the group consisting of abivertinib, afatinib, alflutinib, almonertinib, apatinib, AZD3759, brigatinib, D 0316, D 0317, D 0318, dacomitinib, DZD9008, erlotinib, FCN-411, gefitinib, icotinib, lapatinib, lazertinib, mobocertinib, nazartinib, neratinib, olafertinib, osimertinib, poziotinib, pyrotinib, rezivertinib, TAS6417, vandetanib, varlitinib, XZP-5809, and combinations thereof. In a more preferred embodiment, the EGFR inhibitor is gefitinib or osimertinib. It can be most preferred that the EGFR inhibitor is osimertinib.

In a preferred embodiment of this aspect, a compound of the present invention or a pharmaceutical composition of the invention is administered in combination with an EGFR inhibitor to the patient during each treatment cycle.

In still another embodiment of this aspect, the EGFR inhibitor is administered as sole active agent during the first treatment cycle, followed by the additional administration of a compound of the present invention or a pharmaceutical composition of the invention during the later treatment cycle, wherein a resistance alteration in the EGFR has not yet developed in response to the administration of the EGFR inhibitor alone during the first treatment cycle (i.e. prior to the administration of the combination of the present invention). As noted above, the development of a resistance alteration can be assessed e.g. via a biopsy and a corresponding test in order to detect EGFR mutations.

In another embodiment of this aspect, (i) a compound of the present invention or a pharmaceutical composition of the invention and (ii) the EGFR inhibitor are administered as separate dosage forms or comprised in a single dosage form.

If (i) and (ii) are administered as separate dosage forms, the administration during each treatment cycle may be concomitantly or sequentially. This includes the option that a compound of the present invention or a pharmaceutical composition of the invention is administered first, followed by the administration of the EGFR inhibitor.

In yet another embodiment of this aspect, the treatment results in an extended duration of the therapeutic effect of the EGFR inhibitor compared to the duration of the therapeutic effect of the EGFR inhibitor when administered as the sole active agent. In still another embodiment, the treatment results in an increased therapeutic efficacy of the EGFR inhibitor compared to the therapeutic efficacy of the EGFR inhibitor when administered as the sole active agent. In another embodiment, the treatment results in the prevention of resistance to the EGFR inhibitor.

In another embodiment of this aspect, a compound of the present invention is administered at a daily amount of between about 1 mg and about 3000 mg, preferably of between about 10 mg and about 2000 mg, more preferably of between about 15 mg and about 1000 mg. It can be preferred to administer a compound of the present invention at a daily amount of about 10 mg, about 15 mg, about 20 mg, about 50 mg, about 100 mg, about 250 mg, about 500 mg, about 1000 mg, about 1500 mg, about 2000 mg, about 2500 mg, or about 3000 mg. The administration may take place intermittently, i.e. not every day, but on a day the administration takes place, the afore-mentioned daily amount may be administered.

In another embodiment of this aspect, the EGFR inhibitor is administered at a daily amount that is in the range of a typical daily amount (in particular the daily amount mentioned for the EGFR inhibitor in the label, if available) if the EGFR inhibitor is administered as the sole active agent. The typical daily amount (or the indicated daily amount, if available) depends on the specific EGFR inhibitor that will be used. Thus, gefitinib may e.g. be administered in the combination for use of the present invention at a daily amount of between about 50 and about 300 mg, preferably of between about 100 mg and about 250 mg, and most preferably of between about 150 mg and about 250 mg. Osimertinib may e.g. be administered in the combination for use of the present invention at a daily amount of between about 5 and about 1500 mg, preferably of between about 10 mg and about 100 mg, and most preferably of between about 50 mg and about 80 mg. Erlotinib may e.g. be administered in the combination for use of the present invention at a daily amount of between about 10 mg and about 300 mg, preferably of between about 25 mg and about 200 mg, and most preferably of between about 100 mg and about 150 mg. Afatinib may e.g. be administered in the combination for use of the present invention at a daily amount of between about 5 mg and about 100 mg, preferably of between about 10 mg and about 80 mg, and most preferably of between about 20 mg and about 40 mg. Dacomitinib may e.g. be administered in the combination for use of the present invention at a daily amount of between about 5 mg and about 100 mg, preferably of between about 10 mg and about 80 mg, and most preferably of between about 15 mg and about 50 mg.

In another embodiment of the first aspect, the EGFR inhibitor is administered at a daily amount that is lower than the above-mentioned typical daily amount if the EGFR inhibitor is administered as the sole active agent. In other words, if an EGFR inhibitor is not administered as the sole active agent but in combination with a compound of the present invention or a pharmaceutical composition of the invention, the EGFR inhibitor may be administered at a lower amount than the amount used when the EGFR inhibitor is administered as the sole active agent.

This e.g. means for the examples given above that the daily amount would be at the lower ends of the ranges given or even below these ranges.

In yet a further embodiment of this aspect, the present invention is directed to (i) a compound of the present invention in combination with (ii) an EGFR inhibitor for use in the treatment of a patient suffering from non-small cell lung cancer (NSCLC), wherein the NSCLC exhibits an oncogenic alteration in the EGFR, wherein the compound of the present invention is selected from the group consisting of

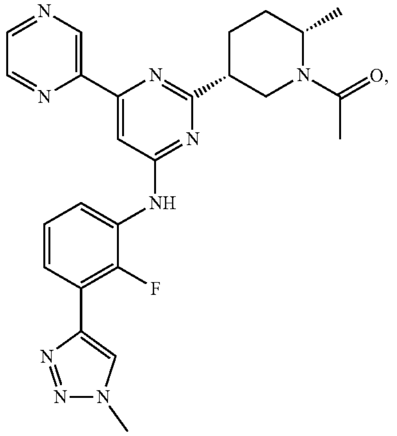

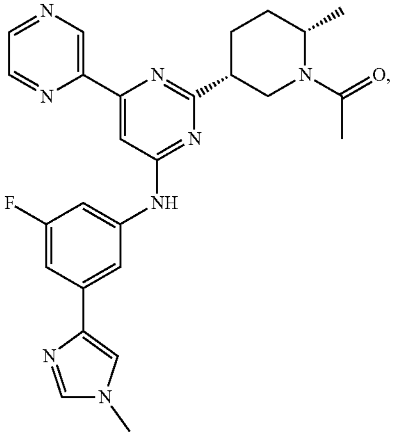

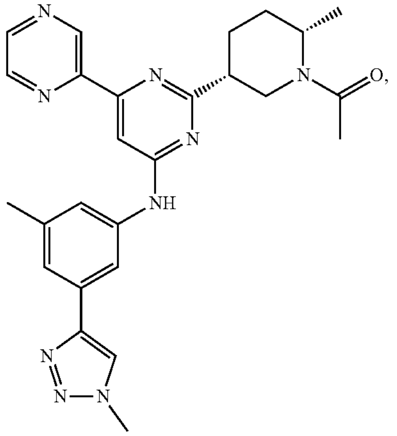

-continued

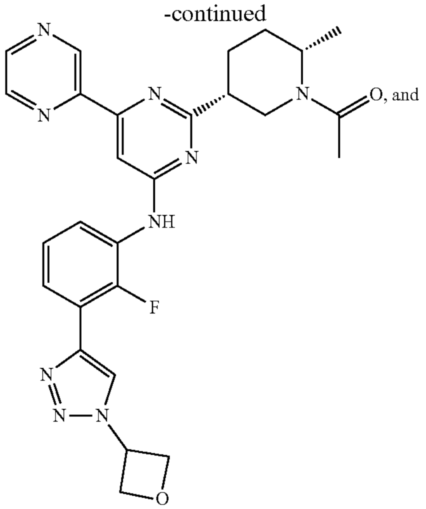

and

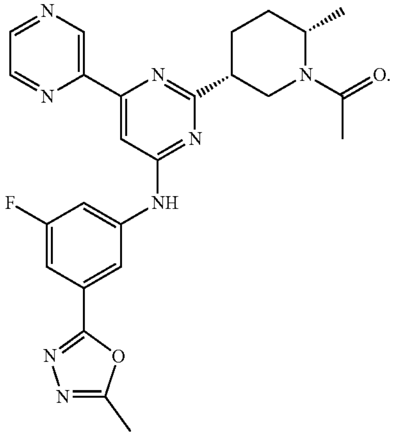 [SMILES: CC(=O)N1C[C@H](c2nc(Nc3cc(F)cc(-c4nnc(C)o4)c3)cc(-c3cnccn3)n2)CC[C@@H]1C]

.

It can be preferred in this embodiment that the EGFR inhibitor is osimertinib and that the oncogenic alteration is caused by a deletion in exon 19 of the EGFR gene (in particular a deletion resulting in the deletion of E746-A750 or L747-E749 in the EGFR); at least one base mutation in the EGFR gene resulting in the amino acid substitution L858R or A750P in the EGFR; and combinations thereof. The at least one base mutation in the EGFR gene resulting in the amino acid substitution T790M in the EGFR corresponding to a resistance alteration in the EGFR may or may not be present in the embodiment where the EGFR inhibitor is osimertinib.

In a related aspect, the present invention is directed to a method of treating NSCLC in a patient in need thereof, said method comprising administering to the patient an effective amount of (i) a compound of the present invention and an effective amount of (ii) an EGFR inhibitor, wherein the NSCLC exhibits an oncogenic alteration in the EGFR.

In another related aspect, the present invention is directed to a method of extending the duration of the therapeutic effect of an EGFR inhibitor in a patient in need thereof, said method comprising administering to the patient an effective amount of (i) a compound of the present invention and an effective amount of (ii) the EGFR inhibitor, wherein the NSCLC exhibits an oncogenic alteration in the EGFR. In other words, the duration of the therapeutic effect of the EGFR inhibitor (when administered in the combination) is extended compared to the duration of the therapeutic effect of the EGFR inhibitor when administered as the sole active agent in NSCLC treatment.

In another related aspect, the present invention is directed to a method of increasing the therapeutic efficacy of an EGFR inhibitor in a patient in need thereof, said method comprising administering to the patient an effective amount of (i) a compound of the present invention and an effective amount of (ii) the EGFR inhibitor, wherein the NSCLC exhibits an oncogenic alteration in the EGFR. In other words, the therapeutic efficacy of the EGFR inhibitor (when administered in the combination) is increased compared to the therapeutic efficacy of the EGFR inhibitor when administered as the sole active agent in NSCLC treatment.

In another related aspect, the present invention is directed to a method of blocking proliferation of a NSCLC cell, said method comprising administering to the cell an effective amount of (i) a compound of the present invention and an effective amount of (ii) an EGFR inhibitor, wherein the NSCLC cell exhibits an oncogenic alteration in the EGFR.

In another related aspect, the present invention is directed to a method of retarding the proliferation of a NSCLC cell, said method comprising administering to the cell an effective amount of (i) a compound of the present invention and an effective amount of (ii) an EGFR inhibitor, wherein the NSCLC cell exhibits an oncogenic alteration in the EGFR.

In the above related aspects, the embodiments outlined above for the initial aspect equally apply.

The term "EGFR" as used herein refers to the "epidermal growth factor receptor". EGFR is a transmembrane protein that is activated by binding of its specific ligands, including epidermal growth factor. Upon activation by its growth factor ligands, EGFR undergoes a transition from an inactive monomeric form to an active homodimer. In addition to forming homodimers after ligand binding, EGFR may pair with another member of the ErbB receptor family, such as ErbB2/Her2/neu, to create an activated heterodimer. EGFR dimerization stimulates its intrinsic intracellular protein-tyrosine kinase activity. As a result, autophosphorylation of several tyrosine residues in the C-terminal domain of EGFR occurs, which elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation. Mutations that lead to EGFR overactivation have been associated with a number of cancers, including lung cancer, and may inter alia result in its constant activation, which results in uncontrolled cell division.

The term "EGFR inhibitor" as used herein refers to molecules capable of acting on EGFR such that intracellular downstream signaling, which ultimately results in cell proliferation, is inhibited. The term "inhibited" in this context means that preferably no downstream signaling takes place any more. However, when a given downstream signaling (set to 100%) is greatly reduced, e.g. to a level of about 70%, about 60%, about 50%, about 40%, about 30%, preferably about 20%, more preferably about 10% or most preferably about 5% or less, such a reduced downstream signaling is still encompassed by the term "inhibiting intracellular downstream signaling". In terms of the medical use of a compound inhibiting downstream signaling, a complete inhibition of the signaling may not be required to achieve a sufficient therapeutic effect. Thus, it needs to be understood that the term "inhibiting" as used herein in this context also refers to a reduction of a downstream signaling, which is sufficient to achieve a desired effect. An EGFR inhibitor may bind to and thus block the extracellular ligand binding domain of the EGFR. Such an EGFR inhibitor is typically an antibody, in particular a monoclonal antibody selected from the group consisting of amivantamab, CDP1, cetuximab, GC1118, HLX07, JMT101, M1231, necitumumab, nimotuzumab, matuzumab, panitumumab, SCT200, SI-B001, SYN004, zalutuzumab, and combinations thereof. An EGFR inhibitor may also bind to the cytoplasmic side of the receptor and thereby inhibit the EGFR tyrosine kinase activity. Such an EGFR inhibitor is typically a small molecule, in particular a small molecule selected from the group consisting of abivertinib, afatinib, alflutinib, almonertinib, apatinib, AZD3759, brigatinib, D 0316, D 0317, D 0318, dacomitinib, DZD9008, erlotinib, FCN-411, gefitinib, icotinib, lapatinib, lazertinib, mobocertinib, nazartinib, neratinib, olafertinib, osimertinib, poziotinib, pyrotinib, rezivertinib, TAS6417, vandetanib, varlitinib, XZP-5809, and combinations thereof.

The term “wherein the NSCLC exhibits an oncogenic alteration in the EGFR” as used herein means that the NSCLC tumors have a mutated version of the EGFR, wherein this mutated version of the EGFR is implicated in the development of the NSCLC. In other words, the mutated version of the EGFR can be regarded as being linked to or causative of the development of the NSCLC, optionally amongst other factors. The mutated version of the EGFR is present in the NSCLC tumors because of an alteration in the EGFR gene, wherein such an alteration is in particular a deletion in the EGFR gene, an insertion in the EGFR gene, a deletion and insertion in the EGFR gene, a duplication in the EGFR gene, an amplification of the EGFR gene, and/or at least one base mutation in the EGFR gene resulting in an amino acid substitution in the EGFR. Corresponding specific alterations are outlined above. Frequently, combinations of such alterations in the EGFR gene are found. The “oncogenic alteration in the EGFR” is not a “resistance alteration in the EGFR” as defined below.

The term “resistance alteration in the EGFR” as used herein means that, upon treatment with an EGFR inhibitor, the NSCLC tumors have acquired (in addition to the oncogenic alteration) a further alteration in the EGFR, wherein this further alteration in the EGFR renders the NSCLC resistant to a treatment by said EGFR inhibitor (i.e. the EGFR inhibitor that was used for the treatment and to which the NSCLC was initially sensitive). The resistance is mediated by an alteration in the EGFR gene, which can in particular be at least one base mutation in the EGFR gene resulting in an amino acid substitution in the EGFR. Thus, in contrast to the “oncogenic alteration in the EGFR” as defined above, the “resistance alteration” is not regarded as being linked to or causative of the initial development of the NSCLC. Rather, it provides a further growth advantage to the NSCLC, namely in that it confers resistance to the NSCLC to the treatment by a specific EGFR inhibitor that was previously administered (and that was effective in treating the NSCLC before the resistance alteration developed as response of the tumor to this treatment). A prominent “resistance alteration in the EGFR” is the amino acid substitution T790M in the EGFR, which is also referred to as gate-keeper mutation. The “resistance alteration in the EGFR” is not an “oncogenic alteration in the EGFR” as defined above. However, both types of alterations can of course be present in the EGFR of a NSCLC tumor and are frequently detected in patients and corresponding cell lines exist as model systems (see e.g. the cell line NCI-H1975).

The term “overactivation” of the EGFR as used herein means that the EGFR is more active compared to the wild-type situation, in particular more active with respect to downstream activation and signaling, thus resulting in cancerous cell growth.

The term “treatment cycle” as used herein means that a medicament is administered for a period of time after an initial assessment of the patient’s condition, wherein the patient’s condition is then typically reassessed before starting another treatment cycle.

Numbered embodiments relating to the above aspect are given in the following. Numbered embodiment 1: A compound according to the present invention or a pharmaceutical composition according to the present invention in combination with an EGFR inhibitor for use in the treatment of a patient suffering from non-small cell lung cancer (NSCLC), wherein the NSCLC exhibits an oncogenic alteration in the EGFR.

Numbered embodiment 2: A compound according to the present invention or a pharmaceutical composition according to the present invention in combination with an EGFR inhibitor for use according to numbered embodiment 1, wherein the oncogenic alteration in the EGFR results in overactivation of the EGFR.

Numbered embodiment 3: A compound according to the present invention or a pharmaceutical composition according to the present invention in combination with an EGFR inhibitor for use according to numbered embodiment 1 or 2, wherein the oncogenic alteration is caused by a deletion and/or insertion in exon 18 or in exon 19 or in exon 20 of the EGFR gene; a kinase domain duplication in the EGFR gene; an amplification of the EGFR gene; at least one base mutation in the EGFR gene resulting in an amino acid substitution in the EGFR selected from the group consisting of L858R, G719S, G719A, G719C, V765A, T783A, S7681, S768V, L861Q, E709X, L819Q, A750P and combinations thereof, wherein X indicates any amino acid; and combinations of any of the foregoing.

Numbered embodiment 4: A compound according to the present invention or a pharmaceutical composition according to the present invention in combination with an EGFR inhibitor for use according to any of numbered embodiments 1 to 3, wherein the oncogenic alteration is caused by a deletion in exon 19 of the EGFR gene, preferably a deletion resulting in the deletion of E746-A750 or L747-E749 in the EGFR; at least one base mutation in the EGFR gene resulting in the amino acid substitution L858R or A750P in the EGFR; and combinations thereof. Numbered embodiment 5: A compound according to the present invention or a pharmaceutical composition according to the present invention in combination with an EGFR inhibitor for use according to any of numbered embodiments 1 to 4 with the proviso that, if the NSCLC additionally exhibits a resistance alteration in the EGFR due to previous administration of an EGFR inhibitor, the EGFR inhibitor of the combination is not the EGFR inhibitor previously administered.

Numbered embodiment 6: A compound according to the present invention or a pharmaceutical composition according to the present invention in combination with an EGFR inhibitor for use according to numbered embodiment 5, wherein the resistance alteration in the EGFR is caused by at least one base mutation in the EGFR gene resulting in an amino acid substitution in the EGFR selected from the group consisting of T790M, C797X, L792X, G796X, L718Q, L718V, G724S, D761Y, V834L, T854A, and combinations thereof, wherein X indicates any amino acid.

Numbered embodiment 7: A compound according to the present invention or a pharmaceutical composition according to the present invention in combination with an EGFR inhibitor for use according to numbered embodiment 5 or 6, wherein the resistance alteration in the EGFR is caused by at least one base mutation in the EGFR gene resulting in the amino acid substitution T790M in the EGFR.

Numbered embodiment 8: A compound according to the present invention or a pharmaceutical composition according to the present invention in combination with an EGFR inhibitor for use according to any of numbered embodiments 1 to 7 wherein the EGFR inhibitor is selected from the group consisting of ABBV-321, abivertinib, afatinib, AFM24, alflutinib (AST2818), almonertinib (HS-10296), apatinib, ASK120067, avitinib (ACO0010), AZD3759, BBT-176, BTDX-1535, BLU-451, BLU-701, BLU-945, brigatinib, CK-101 (RX-518), CLN-081 (TAS6417), CM93, D 0316, D 0317, D 0318, dacomitinib, DZD9008, EMB-01, erlotinib, FCN-411, gefitinib, icotinib, keynatinib, lapatinib, lazertinib, MCLA-129, MRG003, mobocertinib, nazartinib, neratinib, olafertinib, osimertinib, poziotinib, pyrotinib, rezivertinib, SH-1028 (oritinib), sutetinib, TAS2940, TAS6417, vandetanib, varlitinib, XZP-5809, amivantamab, CDP1, cetuximab, GC1118, HLX07, JMT101, M1231, necitumumab, nimotuzumab, matuzumab, panitumumab, SCT200, SI-B001, SYN004, Z650, zalutumumab, ZN-e4, ZZ06, and combinations thereof. Numbered embodiment 9: A compound according to the present invention or a pharmaceutical composition according to the present invention in combination with an EGFR inhibitor for use according to any of numbered embodiments 1 to 8, wherein the EGFR inhibitor is selected from the group consisting of ABBV-321, abivertinib, afatinib, alflutinib, almonertinib, apatinib, AZD3759, brigatinib, D 0316, D 0317, D 0318, dacomitinib, DZD9008, erlotinib, FCN-411, gefitinib, icotinib, lapatinib, lazertinib, mobocertinib, nazartinib, neratinib, olafertinib, osimertinib, poziotinib, pyrotinib, rezivertinib, TAS6417, vandetanib, varlitinib, XZP-5809, amivantamab, CDP1, cetuximab, GC1118, HLX07, JMT101, M1231, necitumumab, nimotuzumab, matuzumab, panitumumab, SCT200, SI-B001, SYN004, zalutumumab, and combinations thereof.

Numbered embodiment 10: A compound according to the present invention or a pharmaceutical composition according to the present invention in combination with an EGFR inhibitor for use according to any of numbered embodiments 1 to 9, wherein the combination is administered to the patient during each treatment cycle.

Numbered embodiment 11: A compound according to the present invention or a pharmaceutical composition according to the present invention in combination with an EGFR inhibitor for use according to any of numbered embodiments 1 to 10, wherein (i) the compound according to the present invention or a pharmaceutical composition according to the present invention and (ii) the EGFR inhibitor are administered as separate dosage forms or comprised in a single dosage form.

Numbered embodiment 12: A compound according to the present invention or a pharmaceutical composition according to the present invention in combination with an EGFR inhibitor for use according to numbered embodiments 11, wherein the administration during each treatment cycle is concomitantly or sequentially if (i) and (ii) are administered as separate dosage forms.

Numbered embodiment 113: A compound according to the present invention or a pharmaceutical composition according to the present invention in combination with an EGFR inhibitor for use according to any of numbered embodiments 1 to 12, wherein the treatment results in an extended duration of the therapeutic effect compared to the duration of the therapeutic effect of the EGFR inhibitor when administered as the sole active agent or wherein the treatment results in an increased therapeutic efficacy compared to the therapeutic efficacy of the EGFR inhibitor when administered as the sole active agent or wherein the treatment results in the prevention of resistance to the EGFR inhibitor.

Numbered embodiment 14: A compound according to the present invention or a pharmaceutical composition according to the present invention in combination with an EGFR inhibitor for use according to any of numbered embodiments 1 to 13, wherein the compound according to the present invention is selected from the group consisting of

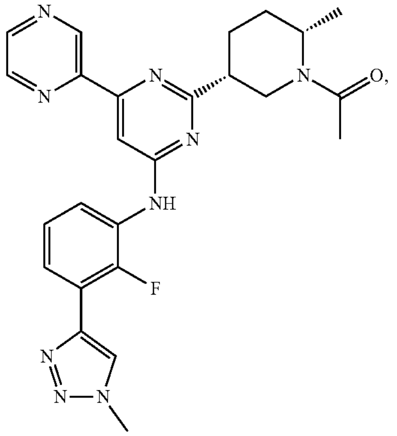

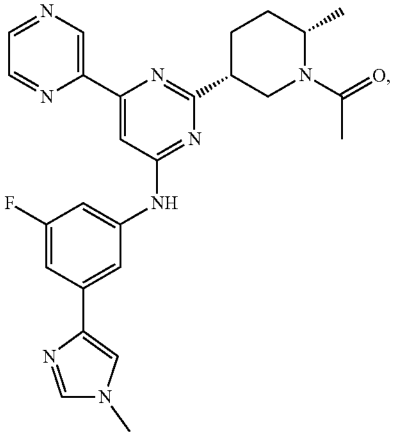

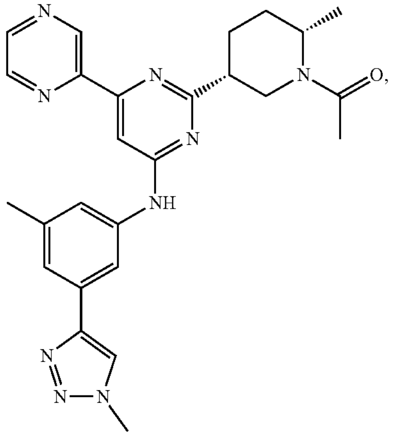

-continued

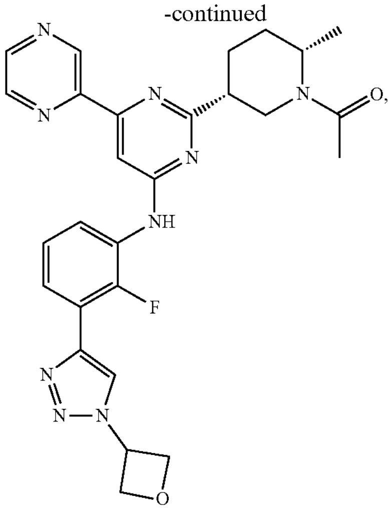

and

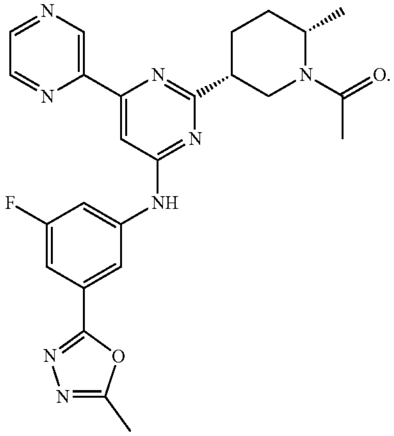 [SMILES: CC(=O)N1C[C@H](c2nc(Nc3cc(F)cc(-c4nnc(C)o4)c3)cc(-c3cnccn3)n2)CC[C@@H]1C]

Embodiments relating to the combination with a KRAS inhibitor The present invention in an aspect also relates to a compound of the present invention or a pharmaceutical composition of the invention in combination with a KRAS inhibitor for use in the treatment of a patient suffering from cancer, wherein the cancer exhibits an oncogenic alteration in the KRAS. This aspect may also be referred to as a combination of compound of the present invention or a pharmaceutical composition of the invention in combination with a KRAS inhibitor for use in the treatment of a patient suffering from cancer, wherein the cancer is characterized by the KRAS-mutational profile given in the one or more indications of the label of the KRAS inhibitor used in the combination (such as e.g. KRAS G12C) or wherein the cancer is characterized by the KRAS-mutational profile targeted in the clinical trial setting by the KRAS inhibitor used in the combination (such as e.g. KRAS G12C).

In a preferred embodiment of this aspect, the oncogenic alteration in the KRAS results in overactivation of KRAS signalling. The oncogenic alteration in the KRAS may even result in constitutively active KRAS signalling (in the meaning that the signaling activity of the GTP-bound KRAS is constitutively active).

In a further preferred embodiment of this aspect, the oncogenic alteration in the KRAS is caused by at least one base mutation in the KRAS gene resulting in an amino acid substitution in the KRAS selected from the group consisting of G12C, G12V, G12D, G13D, Q61H, Q61L, Q61R, K117N and combinations thereof. It can be preferred that the oncogenic alteration is caused by at least one base mutation in the KRAS gene resulting in an amino acid substitution in the KRAS selected from the group consisting of G12C, G12V and G12D. It is most preferred that the oncogenic alteration in the KRAS is caused by at least one base mutation in the KRAS gene resulting in the amino acid substitution G12C in the KRAS.

In another embodiment of this aspect, the cancer is selected from the group consisting of lung cancer, colorectal cancer and pancreatic cancer. The lung cancer is preferably non-small cell lung cancer (NSCLC) and may be locally advanced or metastatic NSCLC, most preferably KRAS G12C-mutated locally advanced or metastatic NSCLC (which may, in the language as used herein, be alternatively formulated as the treatment of a patient suffering from NSCLC, optionally locally advanced or metastatic NSCLC, wherein the NSCLC exhibits the oncogenic alteration G12C in the KRAS).

In another embodiment of this aspect, the KRAS inhibitor is a small molecule inhibitor. Thus, in such an embodiment, the KRAS inhibitor is not a nucleic acid-based inhibitor, such as e.g. a shRNA or RNAi directed to KRAS. In a further embodiment of the first aspect, the KRAS inhibitor is targeted to KRAS G12C, i.e. targeted to treat a cancer that exhibits the oncogenic alteration G12C in the KRAS. Such an inhibitor may in particular be a covalent inhibitor, which targets the cysteine at position 12 present in the G12C KRAS through covalent interactions. The KRAS inhibitor may be selected from the group consisting of RSC-1255, GFH925, JAB-21822, YL-15293, JDQ443, LY3537982, D-1553, GH35, SDGR5, GH52, ERAS-9, AMG510, MRTX849, JNJ-74699157/ARS-3248, BI 1701963, BI 1823911, BAY-293, GDC-6036, MRTX1133, a RAS(ON) inhibitor, and combinations thereof. Alternatively, the KRAS inhibitor may be selected from the group consisting of AMG510, MRTX849, JNJ-74699157/ARS-3248, BI 1701963, BI 1823911, BAY-293, GDC-6036, MRTX1133, a RAS(ON) inhibitor (wherein the RAS(ON) inhibitor is preferably RMC-6291 or RMC-6236), and combinations thereof. In a more preferred embodiment, the KRAS inhibitor is AMG510 or MRTX849. It can be most preferred that the KRAS inhibitor is AMG510.

In a preferred embodiment of this aspect, the combination is administered to the patient during each treatment cycle.

In another embodiment of this aspect, the compound of the present invention and the KRAS inhibitor are administered as separate dosage forms or comprised in a single dosage form. If the compound of the present invention and the KRAS inhibitor are administered as separate dosage forms, the administration during each treatment cycle may be concomitantly or sequentially. This includes the option that the compound of the present invention is administered first, followed by the administration of the KRAS inhibitor.

In yet another embodiment of this aspect, the treatment results in an extended duration of the therapeutic effect of the KRAS inhibitor compared to the duration of the therapeutic effect of the KRAS inhibitor when administered as the sole active agent. In still another embodiment, the treatment results in an increased therapeutic efficacy of the KRAS inhibitor compared to the therapeutic efficacy of the KRAS inhibitor when administered as the sole active agent. In another embodiment, the treatment results in the prevention of resistance to the KRAS inhibitor.

In another embodiment of this aspect, a compound of the present invention is administered at a daily amount of between about 1 mg and about 3000 mg, preferably of between about 10 mg and about 2000 mg, more preferably of between about 15 mg and about 1000 mg. It can be preferred to administer the compound of the present invention at a daily amount of about 10 mg, about 15 mg, about 20 mg, about 50 mg, about 100 mg, about 250 mg, about 500 mg, about 1000 mg, about 1500 mg, about 2000 mg, about 2500 mg, or about 3000 mg. The administration may take place intermittently, i.e. not every day, but on a day the administration takes place, the afore-mentioned daily amount may be administered.

In another embodiment of this aspect, the KRAS inhibitor is administered at a daily amount that is in the range of a typical daily amount (in particular the daily amount mentioned for the KRAS inhibitor in the label, if available) if the KRAS inhibitor is administered as the sole active agent. The typical daily amount (or the indicated daily amount, if available) depends on the specific KRAS inhibitor that will be used. Typically, a KRAS inhibitor will be administered at a daily amount of between about 10 mg and about 2000 mg. Thus, AMG510 may e.g. be administered in the combination for use of the present invention at a daily amount of between about 240 mg and about 1200 mg, about 480 mg and about 1200 mg, or about 600 mg to about 1200 mg, preferably of between about 720 mg to about 1080 mg, more preferably of between about 840 mg and about 960 mg or about 960 mg. MRTX849 may e.g. be administered in the combination for use of the present invention at a daily amount of between about 200 mg and about 1400 mg, or about 400 mg and about 1300 mg, preferably of between about 600 mg and about 1200 mg, most preferably at about 1200 mg.

In another embodiment of this aspect, the KRAS inhibitor is administered at a daily amount that is lower than the above-mentioned typical daily amount if the KRAS inhibitor is administered as the sole active agent. In other words, if a KRAS inhibitor is not administered as the sole active agent but in the combination for use according to the present invention, the KRAS inhibitor may be administered at a lower amount than the amount used when the KRAS inhibitor is administered as the sole active agent. This e.g. means for the examples given above that the daily amount would be at the lower ends of the ranges given or even below these ranges.

In yet a further embodiment of this aspect, the present invention is directed to (i) a compound of the present invention in combination with (ii) a KRAS inhibitor for use in the treatment of a patient suffering from cancer, wherein the cancer exhibits an oncogenic alteration in the KRAS, wherein the compound of the present invention is selected from the group consisting of

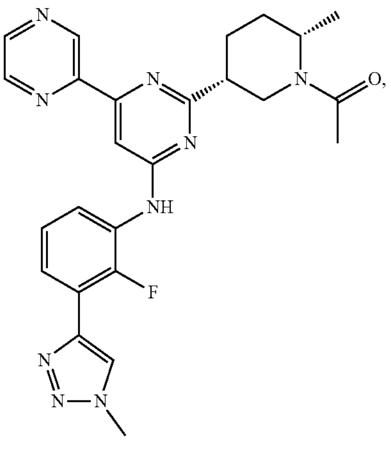
,

-continued

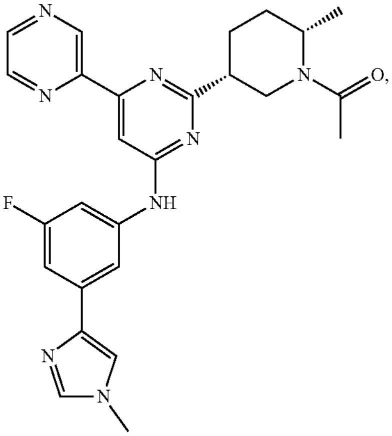
,

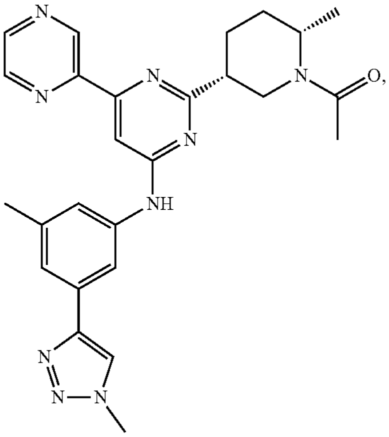
,

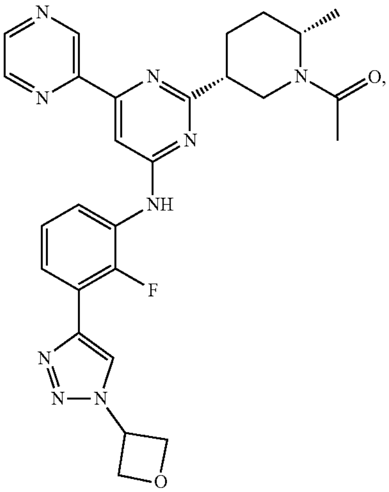
, and

-continued

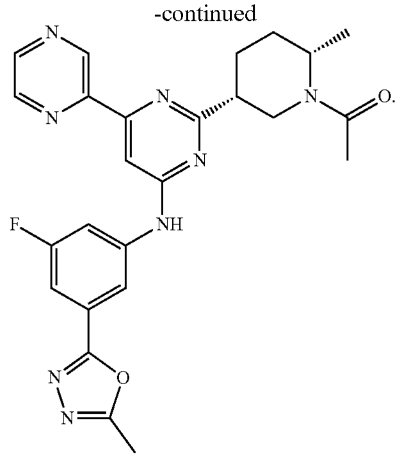

In a related aspect, the present invention is directed to a method of treating cancer in a patient in need thereof, said method comprising administering to the patient an effective amount of (i) a compound of the present invention and an effective amount of (ii) a KRAS inhibitor, wherein the cancer exhibits an oncogenic alteration in the KRAS.

In another related aspect, the present invention is directed to a method of extending the duration of the therapeutic effect of a KRAS inhibitor in a patient in need thereof, said method comprising administering to the patient an effective amount of (i) a compounds of the present invention and an effective amount of (ii) the KRAS inhibitor, wherein the cancer exhibits an oncogenic alteration in the KRAS. In other words, the duration of the therapeutic effect of the KRAS inhibitor (when administered in the combination) is extended compared to the duration of the therapeutic effect of the KRAS inhibitor when administered as the sole active agent in cancer treatment.

In another related aspect, the present invention is directed to a method of increasing the therapeutic efficacy of a KRAS inhibitor in a patient in need thereof, said method comprising administering to the patient an effective amount of (i) a compound of the present invention and an effective amount of (ii) the KRAS inhibitor, wherein the cancer exhibits an oncogenic alteration in the KRAS. In other words, the therapeutic efficacy of the KRAS inhibitor (when administered in the combination) is increased compared to the therapeutic efficacy of the KRAS inhibitor when administered as the sole active agent in cancer treatment. In another related aspect, the present invention is directed to a method of blocking proliferation of a cancer cell, said method comprising administering to the cell an effective amount of (i) a compound of the present invention and an effective amount of (ii) a KRAS inhibitor, wherein the cancer cell exhibits an oncogenic alteration in the KRAS.

In another related aspect, the present invention is directed to a method of retarding the proliferation of a cancer cell, said method comprising administering to the cell an effective amount of (i) a compound of the present invention and an effective amount of (ii) a KRAS inhibitor, wherein the cancer cell exhibits an oncogenic alteration in the KRAS.

In the above related aspects, the embodiments outlined above for the initial aspect equally apply.

The term "KRAS" as used herein refers to the "Kirsten Rat Sarcoma" protein. KRAS is a GTPase that is an essential mediator of intracellular signaling pathways involved in tumor cell growth and survival. In normal cells, KRAS functions as a molecular switch, alternating between inactive GDP-bound and active GTP-bound states. Transition between these states is facilitated by guanine nucleotide exchange factors (GEFs), which load GTP and activate KRAS, and GTP hydrolysis, which is catalyzed by GTPase-activating proteins (GAPs) to inactivate KRAS. GTP-binding to KRAS promotes binding of effectors to trigger signal transduction pathways including RAF-MEK-ERK (MAPK). Somatic activating mutations in KRAS are a hallmark of cancer and prevent the association of GAPs, thereby stabilizing effector-binding and enhancing KRAS signaling. Patients with KRAS mutant tumors have significantly poorer outcomes and worse prognosis.

The term "KRAS inhibitor" as used herein refers to molecules capable of acting on KRAS such that intracellular downstream signaling, which ultimately results in cell proliferation, is inhibited. The term "inhibited" in this context means that preferably no downstream signaling takes place any more. However, when a given downstream signaling (set to 100%) is greatly reduced, e.g. to a level of about 70%, about 60%, about 50%, about 40%, about 30%, preferably about 20%, more preferably about 10% or most preferably about 5% or less, such a reduced downstream signaling is still encompassed by the term "inhibiting intracellular downstream signaling". In terms of the medical use of a compound inhibiting downstream signaling, a complete inhibition of the signaling may not be required to achieve a sufficient therapeutic effect. Thus, it needs to be understood that the term "inhibiting" as used herein in this context also refers to a reduction of a downstream signaling, which is sufficient to achieve a desired effect. A KRAS inhibitor may covalently bind to KRAS, in particular to the cysteine at position 12 in the KRAS G12C. If the KRAS inhibitor targets and/or binds to this cysteine, the inhibitor is typically referred to as "KRAS G12C inhibitor" and examples of such inhibitors are AMG510 (CAS-Nr. 2296729-00-3), MRTX849 (CAS-Nr. 2326521-71-3), JNJ-74699157/ARS-3248, BI 1823911, GDC-6036 and RMC-6291. Very recently, the first KRAS G12C-modulating agent obtained FDA-approval, namely LUMAKRAS (sotorasib corresponding to AMG510 from Amgen) tablets for the treatment of KRAS G12C-mutated locally advanced or metastatic non-small cell lung cancer (NSCLC). Another KRAS G12C-modulating agent is expected to follow soon, namely adagrasib (corresponding to MRTX849 from Mirati Therapeutics). A "KRAS G12D inhibitor" is an inhibitor specific for KRAS G12D, and so on. An example of a KRAS G12D inhibitor is MRTX1133. Alternatively, a KRAS inhibitor may block the interactions of KRAS with other proteins, in particular the KRAS-SOS1 interaction. Such KRAS-SOS1 inhibitors are e.g. BI 1701963 and BAY-293 (CAS Nr. 2244904-70-7). There are also so-called RAS(ON) inhibitors, which bind to the mutated GTP-bound KRAS (e.g. G12C GTP-bound KRAS or G12V GTP-bound KRAS or G12D GTP-bound KRAS or G13D GTP-bound KRAS or Q61H GTP-bound KRAS or Q61L GTP-bound KRAS or Q61R GTP-bound KRAS) and prevent RAF engagement by blocking the effector face of the respective KRAS in that they form a three-component complex between the RAS (ON) inhibitor (a synthetic ligand), KRAS and cyclophilin A (see Revolution Medicines for further details, e.g. WO 2021/091956). RMC-6291 is a $RAS^{G12C}$(ON) inhibitor by Revolution Medicines that targets $KRAS^{G12C}$ by the afore-mentioned mechanism. RMC-6236 is a RAS(ON) inhibitor by Revolution Medicines that targets multiple RAS mutations including KRAS mutations by the afore-mentioned mechanism.

The term "wherein the cancer exhibits an oncogenic alteration in the KRAS" as used herein means that the tumor has a mutated version of the KRAS, wherein this mutated version of the KRAS is implicated in the development of the cancer. In other words, the mutated version of the KRAS can be regarded as being linked to or causative of the development of the cancer, optionally amongst other factors. The mutated version of the KRAS is present in the tumor because of an alteration in the KRAS gene, wherein such an alteration is in particular at least one base mutation in the KRAS gene resulting in an amino acid substitution in the KRAS. Corresponding specific alterations are outlined above, wherein a prominent alteration is in particular the KRAS G12C alteration. As noted above, KRAS mutations are present in up to 25% of cancers, wherein the oncogenic variants have different prevalence rates in different cancers (see Box 1 of Mullard, *Nature reviews DRUG DISCOVERY*, Vol. 18, December 2019:887-891). The term "overactivation" of the KRAS as used herein means that the KRAS is more active compared to the wild-type situation, in particular more active with respect to downstream activation and signaling, thus resulting in cancerous cell growth.

Numbered embodiments relating to the above aspect are given in the following. Numbered embodiment 1: A compound according to the present invention or a pharmaceutical composition according to the present invention in combination with a KRAS inhibitor for use in the treatment of a patient suffering from cancer, wherein the cancer exhibits an oncogenic alteration in the KRAS.

Numbered embodiment 2: A compound according to the present invention or a pharmaceutical composition according to the present invention in combination with a KRAS inhibitor for use according to numbered embodiment 1, wherein the oncogenic alteration in the KRAS results in overactivation of KRAS signalling. Numbered embodiment 3: A compound according to the present invention or a pharmaceutical composition according to the present invention in combination with a KRAS inhibitor for use according to numbered embodiment 1 or 2, wherein the oncogenic alteration is caused by at least one base mutation in the KRAS gene resulting in an amino acid substitution in the KRAS selected from the group consisting of G12C, G12V, G12D, G13D, Q61H, Q61L, Q61R, K117N and combinations thereof.

Numbered embodiment 4: A compound according to the present invention or a pharmaceutical composition according to the present invention in combination with a KRAS inhibitor for use according to any of numbered embodiments 1 to 4, wherein the KRAS inhibitor is selected from the group consisting of RSC-1255, GFH925, JAB-21822, YL-15293, JDQ443, LY3537982, D-1553, GH35, SDGR5, GH52, ERAS-9, AMG510, MRTX849, JNJ-74699157/ARS-3248, BI 1701963, BI 1823911, BAY-293, GDC-6036, MRTX1133, a RAS(ON) inhibitor, and combinations thereof.

Numbered embodiment 5: A compound according to the present invention or a pharmaceutical composition according to the present invention in combination with a KRAS inhibitor for use according to any of numbered embodiments 1 to 4, wherein the KRAS inhibitor is selected from the group consisting of AMG510, MRTX849, JNJ-74699157/ARS-3248, BI 1701963, BI 1823911, BAY-293, GDC-6036, MRTX1133, a RAS(ON) inhibitor, and combinations thereof.

Numbered embodiment 6: A compound according to the present invention or a pharmaceutical composition according to the present invention in combination with a KRAS inhibitor for use according to any of numbered embodiments 1 to 5, wherein the oncogenic alteration is caused by at least one base mutation in the KRAS gene resulting in the amino acid substitution G12C in the KRAS.

Numbered embodiment 7: A compound according to the present invention or a pharmaceutical composition according to the present invention in combination with a KRAS inhibitor for use according to any of numbered embodiments 1 to 5, wherein the oncogenic alteration is caused by at least one base mutation in the KRAS gene resulting in the amino acid substitution G12C in the KRAS and the KRAS inhibitor is a KRAS G12C inhibitor.

Numbered embodiment 8: A compound according to the present invention or a pharmaceutical composition according to the present invention in combination with a KRAS inhibitor for use according to any of numbered embodiments 1 to 7, wherein the cancer is selected from the group consisting of lung cancer, colorectal cancer and pancreatic cancer.

Numbered embodiment 9: A compound according to the present invention or a pharmaceutical composition according to the present invention in combination with a KRAS inhibitor for use according to any of numbered embodiments 1 to 8, wherein the combination is administered to the patient during each treatment cycle.

Numbered embodiment 10: A compound according to the present invention or a pharmaceutical composition according to the present invention in combination with a KRAS inhibitor for use according to any of numbered embodiments 1 to 9, wherein (i) the compound according to the present invention or a pharmaceutical composition according to the present invention and (ii) the KRAS inhibitor are administered as separate dosage forms or comprised in a single dosage form.

Numbered embodiment 11: A compound according to the present invention or a pharmaceutical composition according to the present invention in combination with a KRAS inhibitor for use according to numbered embodiment 10, wherein the administration during each treatment cycle is concomitantly or sequentially if (i) and (ii) are administered as separate dosage forms.

Numbered embodiment 12: A compound according to the present invention or a pharmaceutical composition according to the present invention in combination with a KRAS inhibitor for use according to any of numbered embodiments 1 to 11, wherein the treatment results in an extended duration of the therapeutic effect compared to the duration of the therapeutic effect of the KRAS inhibitor when administered as the sole active agent; or wherein the treatment results in an increased therapeutic efficacy compared to the therapeutic efficacy of the KRAS inhibitor when administered as the sole active agent; or wherein the treatment results in the prevention of resistance to the KRAS inhibitor.

Numbered embodiment 13: A compound according to the present invention or a pharmaceutical composition according to the present invention in combination with a KRAS inhibitor for use according to any of numbered embodiments 1 to 12, wherein the compound according to the present invention is selected from the group consisting of

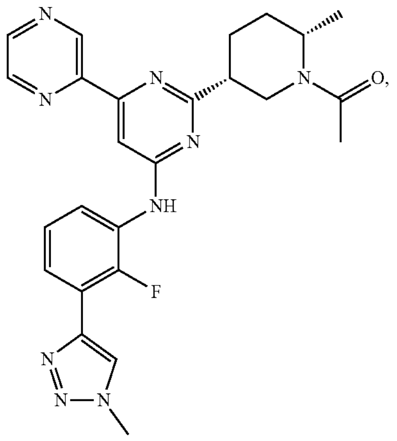

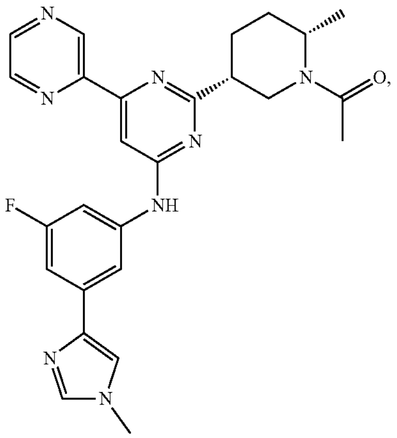

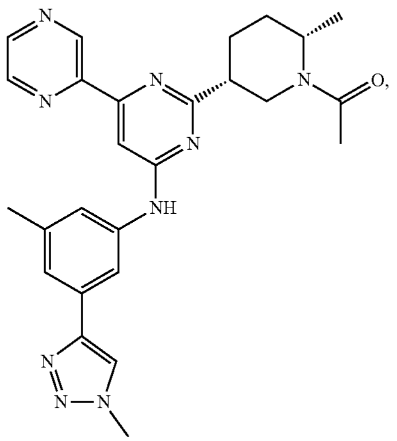

-continued

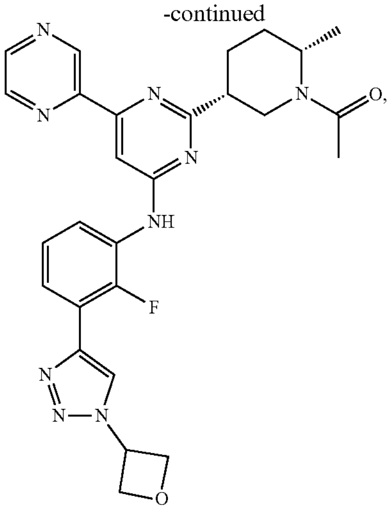

and

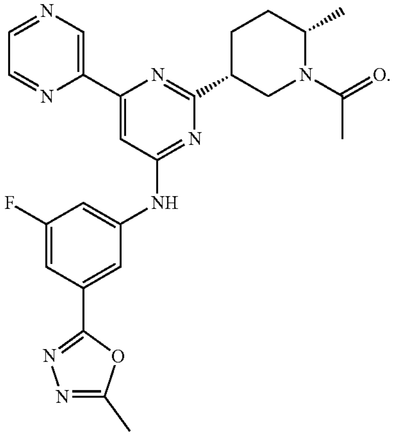 [SMILES: CC(=O)N1C[C@H](c2nc(Nc3cc(F)cc(-c4nnc(C)o4)c3)cc(-c3cnccn3)n2)CC[C@@H]1C]

Numbered embodiment 14: A kit comprising (i) a pharmaceutical dosage form comprising a compound according to the present invention and (ii) a pharmaceutical dosage form comprising a KRAS inhibitor.

Numbered embodiment 15: A pharmaceutical dosage form comprising (i) a compound of the present invention and (ii) a KRAS inhibitor.

Numbered embodiment 16: The kit according to numbered embodiment 14 or the pharmaceutical dosage form according to numbered embodiment 15, wherein the KRAS inhibitor is selected from the group consisting of RSC-1255, GFH925, JAB-21822, YL-15293, JDQ443, LY3537982, D-1553, GH35, SDGR5, GH52, ERAS-9, AMG510, MRTX849, JNJ-74699157/ARS-3248, BI 1701963, BI 1823911, BAY-293, GDC-6036, MRTX1133, a RAS(ON) inhibitor, and combinations thereof.

Numbered embodiment 17: The kit according to numbered embodiment 16 or the pharmaceutical dosage form according to numbered embodiment 16, wherein the KRAS inhibitor is selected from the group consisting AMG510, MRTX849, JNJ-74699157/ARS-3248, BI 1701963, BI 1823911, BAY-293, GDC-6036, MRTX1133, a RAS(ON) inhibitor, and combinations thereof.

Numbered embodiment 18: The kit according to numbered embodiment 14, 16 or 17, or the pharmaceutical dosage form according to numbered embodiment 15, 16 or 17, wherein the compound according to the present invention is selected from the group consisting of

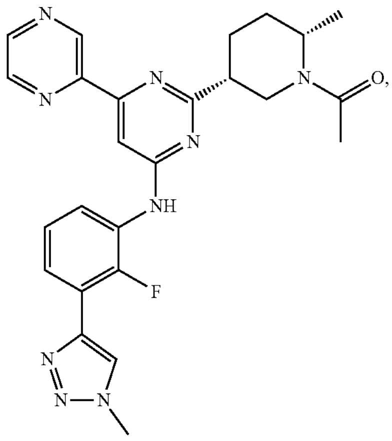

,

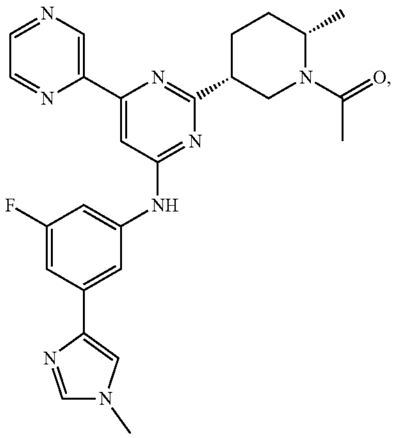

,

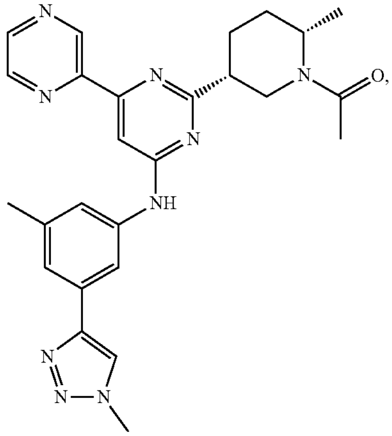

,

-continued

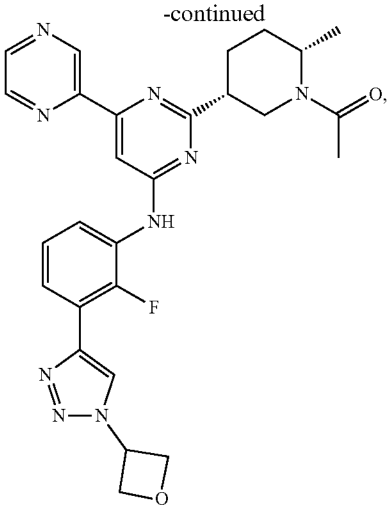

, and

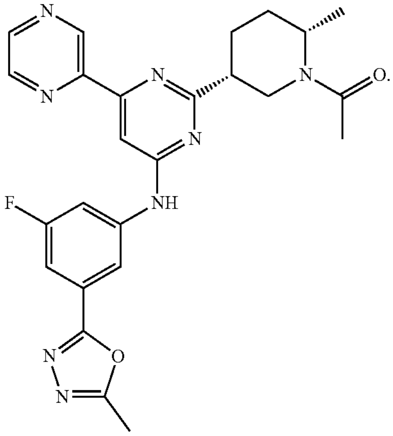 [SMILES: CC(=O)N1C[C@H](c2nc(Nc3cc(F)cc(-c4nnc(C)o4)c3)cc(-c3cnccn3)n2)CC[C@@H]1C]

.

Embodiments Relating to a Fibrotic Disease

The present invention also relates to a compound of the present invention or a pharmaceutical composition of the invention for use in the treatment or amelioration of a fibrotic disease, in particular idiopathic pulmonary fibrosis (IPF) or non-alcoholic steatohepatitis (NASH), optionally in combination with known anti-fibrotic or anti-inflammatory agents.

The fibrotic disease may be selected from the group consisting of pulmonary fibrosis, idiopathic pulmonary fibrosis, radiation-induced pneumonitis, radiation fibrosis, acute respiratory distress syndrome, chronic obstructive pulmonary disease, interstitial lung disease, myocardial infarction, cardiac fibrosis and hypertrophy, ischemic stroke, ischemic kidney disease, renal fibrosis, rheumatoid arthritis, liver fibrosis, NASH (non-alcoholic steatohepatitis), chronic hepatitis, cirrhosis, inflammatory bowel disease, Crohn's disease, scleroderma, keloid, post-operative fibrosis, chemotherapy induced fibrosis (e.g., chemotherapy induced pulmonary fibrosis or ovarian cortical fibrosis), nephrogenic systemic fibrosis, retroperitoneal fibrosis, myelofibrosis, mediastinal fibrosis, cystic fibrosis, asbestosis, asthma, pulmonary hypertension, systemic fibrosis, skin fibrosis, hypertension induced renal and cardiac fibrosis. The fibrotic disease may also be interstitial lung disease (IDL), in particular idiopathic interstitial pneumonia (IIP). IIP can be selected from the group consisting of chronic fibrosing interstitial pneumonia, smoking-related interstitial pneumonia and acute/subacute interstitial pneumonia, wherein the chronic fibrosing interstitial pneumonia can be idiopathic pulmonary fibrosis (IPF) or non-specific interstitial pneumonia (NSIP).

In particular when it comes to the treatment of NASH, the known anti-fibrotic or anti-inflammatory agent may be selected from the group consisting of vitamine E (RRR-α-tocopherol), Pioglitazone (Actos), MGL-3196 (Resmetirom), Elafibranor, selonsertib (SEL; GS-4997), Dapagliflozin, Nesinaact 25/15 (Alogliptin benzoate 25 mg, pioglitazone hydrochloride 15 mg), Losartan, Aramchol, Cenicriviroc, MSDC-0602K and Metformin.

The compounds provided herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, and/or solubility enhancers, or any combination thereof. In particular, the pharmaceutical compositions may comprise one or more solubility enhancers, such as, e.g., poly(ethylene glycol), including poly (ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, α-cyclodextrin, β-cyclodextrin, γ-cyclodextrin, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, sulfobutylether-β-cyclodextrin, sulfobutylether-γ-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcellulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

The pharmaceutical compositions can be formulated by techniques known to the person skilled in the art, such as the techniques published in "Remington: The Science and Practice of Pharmacy", Pharmaceutical Press, 22nd edition. The pharmaceutical compositions can be formulated as dosage forms for oral, parenteral, such as intramuscular, intravenous, subcutaneous, intradermal, intraarterial, intracardial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of formula (I) or the above described pharmaceutical compositions comprising a compound of formula (I) may be administered to a subject by any convenient route of administration, whether systemically/peripherally or at the site of desired action, including but not limited to one or more of: oral (e.g., as a tablet, capsule, or as an ingestible solution), topical (e.g., transdermal, intranasal, ocular, buccal, and sublingual), parenteral (e.g., using injection techniques or infusion techniques, and including, for example, by injection, e.g., subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g., through mouth or nose), gastrointestinal, intrauterine, intraocular, subcutaneous, ophthalmic (including intravitreal or intracameral), rectal, and vaginal.

If said compounds or pharmaceutical compositions are administered parenterally, then examples of such administration include one or more of: intravenously, intraarterially, intraperitoneally, intrathecally, intraventricularly, intraurethrally, intrasternally, intracardially, intracranially, intramuscularly or subcutaneously administering the compounds or pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Said compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

Alternatively, said compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

Said compounds or pharmaceutical compositions may also be administered by sustained release systems. Suitable examples of sustained-release compositions include semipermeable polymer matrices in the form of shaped articles, e.g., films, or microcapsules. Sustained-release matrices include, e.g., polylactides (see, e.g., U.S. Pat. No. 3,773, 919), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP133988). Sustained-release pharmaceutical compositions also include liposomally entrapped compounds. Liposomes containing a compound of the present invention can be prepared by methods known in the art, such as, e.g., the methods described in any one of: DE3218121; Epstein et al., Proc. Natl. Acad. Sci. (USA) 82:3688-3692 (1985); Hwang et al., Proc. Natl. Acad. Sci. (USA) 77:4030-4034 (1980); EP0052322; EP0036676; EP088046; EP0143949; EP0142641; JP 83-118008; U.S. Pat. Nos. 4,485,045; 4,544,545; and EP0102324.

Said compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

It is also envisaged to prepare dry powder formulations of the compounds of formula (I) for pulmonary administration, particularly inhalation. Such dry powders may be prepared by spray drying under conditions which result in a substantially amorphous glassy or a substantially crystalline bioactive powder. Accordingly, dry powders of the compounds of the present invention can be made according to the emulsification/spray drying process disclosed in WO 99/16419 or WO 01/85136. Spray drying of solution formulations of the compounds of the present invention can be carried out, e.g., as described generally in the "Spray Drying Handbook", 5th ed., K. Masters, John Wiley & Sons, Inc., NY (1991), and in WO 97/41833 or WO 03/053411.

For topical application to the skin, said compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

The present invention thus relates to the compounds or the pharmaceutical compositions provided herein, wherein the corresponding compound or pharmaceutical composition is to be administered by any one of: an oral route; topical route, including by transdermal, intranasal, ocular, buccal, or sublingual route; parenteral route using injection techniques or infusion techniques, including by subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intrasternal, intraventricular, intraurethral, or intracranial route; pulmonary route, including by inhalation or insufflation therapy; gastrointestinal route; intrauterine route; intraocular route; subcutaneous route; ophthalmic route, including by intravitreal, or intracameral route; rectal route; or vaginal route. Particularly preferred routes of administration of the compounds or pharmaceutical compositions of the present invention are oral forms of administration.

Typically, a physician will determine the dosage which will be most suitable for an individual subject. The specific dose level and frequency of dosage for any particular individual subject may be varied and will depend upon a variety of factors including the age, body weight, general health, sex, diet, mode and time of administration, rate of excretion, drug combination, the severity of the particular condition, and the individual subject undergoing therapy.

A proposed, yet non-limiting dose of the compounds according to the invention for administration to a human (of approximately 70 kg body weight) may be 0.05 to 2000 mg, preferably 0.1 mg to 1000 mg, of the active ingredient per unit dose. The unit dose may be administered, e.g., 1, 2, 3 or more times per day. The unit dose may also be administered 1 to 7 times per week, e.g., with one, two or more administration(s) per day. It will be appreciated that it may be necessary to make routine variations to the dosage depending on the age and weight of the patient/subject as well as the severity of the condition to be treated. The precise dose and also the route of administration will ultimately be at the discretion of the attendant physician.

The compounds of formula (I) can be used in combination with other therapeutic agents, including in particular other anticancer agents. When a compound of the invention is used in combination with a second therapeutic agent active against the same disease, the dose of each compound may differ from that when the compound is used alone. The combination of a compound of the present invention with a second therapeutic agent may comprise the administration of the second therapeutic agent simultaneously/concomitantly or sequentially/separately with the compound of the invention.

Preferably, the second therapeutic agent to be administered in combination with a compound of this invention is an anticancer drug. The anticancer drug to be administered in combination with a compound of formula (I) according to the present invention may, e.g., be a androgen receptor (AR) antagonists, a receptor tyrosine kinase (RTK) inhibitor, a MAPK kinase inhibitor, a checkpoint kinase inhibitor, and/or, in general, an agent used in immunotherapy of cancer. For example, many cancers are known to involve AR, BRAF, MEK, ERK and/or EGFR expression. Thus, within the present invention the second therapeutic agent to be administered in combination with a compound of this invention, may be an inhibitor of AR, BRAF, MEK, ERK and/or EGFR. In particular not limiting embodiments:

(i) said androgen receptor antagonist is enzalutamide or the complementary CYP17A1 (17alpha-hydroxylase/C17,20 lyase) inhibitor abiraterone
(ii) said BRAFi is vemurafenib, dabrafenib, encorafenib, LGX818, PLX4720, TAK-632, MLN2480, SB590885, XL281, BMS-908662, PLX3603, R05185426, GSK2118436 or RAF265,
(iii) said MEKi is AZD6244, trametinib, selumetinib, cobimetinib, binimetinib, MEK162, R05126766, GDC-0623, PD 0325901, CI-1040, PD-035901, hypothemycin or TAK-733,
(iv) said ERKi is ulixertinib, corynoxeine, SCH772984, XMD8-92, FR 180204, GDC-0994, ERK5-IN-1, DEL-22379, BIX 02189, ERK inhibitor (CAS No. 1049738-54-6), ERK inhibitor III (CAS No. 331656-92-9), GDC-0994, honokiol, LY3214996, CC-90003, deltonin, VRT752271, TIC10, astragaloside IV, XMD8-92, VX-11e, mogrol, or VTX11e, and/or (v) said EGFRi is cetuximab, panitumumab, zalutumumab, nimotuzumab, matuzumab, gefitinib, erlotinib, lapatinib, neratinib, vandetanib, necitumumab, osimertinib, afatinib, dacomitinib, AP26113, EGFR inhibitor (CAS No. 879127-07-8), EGFR/ErbB-2/ErbB-4 Inhibitor (CAS No. 881001-19-0), EGFR/ErbB-2 Inhibitor (CAS No. 179248-61-4), EGFR inhibitor II (BIBX 1382,CAS No. 196612-93-8), EGFR inhibitor III (CAS No. 733009-42-2), EGFR/ErbB-2/ErbB-4 Inhibitor II (CAS No. 944341-54-2) or PKCβII/EGFR Inhibitor (CAS No. 145915-60-2).

In particular embodiments of the invention, the second therapeutic agent administered in combination with a compound of the invention may be an immunotherapy agent, more particular immuno-oncology agent, such as, e.g. an agent targeting CD52, PD-L1, CTLA4, CD20, or PD-1. Agents that may be used in combination with a compound of the present invention include, for example, alemtuzumab, atezolizumab, ipilimumab, nivolumab, ofatumumab, pembrolizumab, rituximab.

The second therapeutic agent may also be selected from: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analogue antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is dysregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and corresponding kinase inhibitors (such as epidermal growth factor receptor (EGFR) kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine, aminopeptidase inhibitors, proteasome inhibitors, cyclooxygenase inhibitors (for example, cyclooxygenase-1 or cyclooxygenase-2 inhibitors), topoisomerase inhibitors (for example, topoisomerase I inhibitors or topoisomerase II inhibitors), and poly ADP ribose polymerase inhibitors (PARP inhibitors).

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate. A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, or tesetaxel), a *Vinca* alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with a compound of the present invention may be, for example, afatinib, acalabrutinib, alectinib, apatinib, axitinib, bosutinib, cabozantinib, canertinib, crenolanib, cediranib, crizotinib, damnacanthal, dasatinib, dacomitinib, entospletinib, entrectinib, erlotinib, foretinib, fostamatinib, gilteritinib, glesatinib, gefitinib, ibrutinib, icotinib, imatinib, linafanib, lapatinib, lestaurtinib, motesanib, mubritinib, nintedanib, nilotinib, ONT-380, osimertinib, pazopanib, quizartinib, regorafenib, rociletinib, radotinib, savolitinib, sitravatinib, semaxanib, sorafenib, sunitinib, savolitinib, sitravatinig, tesevatinib, vatalanib, vemurafenib or vandetanib.

A topoisomerase-inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin). A PARP inhibitor which can be used as an anticancer drug in combination with a compound of the present invention may be, for example, BMN-673, olaparib, rucaparib, veliparib, CEP 9722, MK 4827, BGB-290, or 3-aminobenzamide. Further anticancer drugs may also be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, vorinostat, or iniparib.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the compounds of the invention. Antibodies may, for example, be immuno-oncology antibodies, such as ado-trastuzumab, alemtuzumab, atezolizumab, avelumab, bevacizumab, blinatumomab, brentuximab, capromab, cetuximab, ipilimumab, necitumumab, nivolumab, panitumumab, pembrolizumab, pertuzumab, ramucirumab, trastuzumab, or rituximab.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the compound of the present invention (i.e., the compound of formula (I) or a pharmaceutically acceptable salt, solvate, cocrystal, tautomer, racemate, enantiomer, or diastereomer or mixture thereof) or the second therapeutic agent may be administered first. When administration is simultaneous, the combination may be administered either in the same pharmaceutical composition or in different pharmaceutical compositions. When combined in the same formulation, it will be appreciated that the two compounds must be stable and compatible with each other and the other components of the formulation. When formulated separately, they may be provided in any convenient formulation.

The compounds of formula (I) can also be administered in combination with physical therapy, such as radiotherapy. Radiotherapy may commence before, after, or simultaneously with administration of the compounds of the invention. For example, radiotherapy may commence 1-10 minutes, 1-10 hours or 24-72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens.

The present invention thus relates to a compound of formula (I) or a pharmaceutically acceptable salt, solvate, cocrystal, tautomer, racemate, enantiomer, or diastereomer or mixture thereof, or a pharmaceutical composition comprising any of the aforementioned entities in combination with a pharmaceutically acceptable excipient, for use in the treatment or prevention of cancer, wherein the compound or the pharmaceutical composition is to be administered in combination with an anticancer drug and/or in combination with radiotherapy.

Yet, the compounds of formula (I) can also be used in monotherapy, particularly in the monotherapeutic treatment or prevention of cancer (i.e., without administering any other anticancer agents until the treatment with the compound(s) of formula (I) is terminated). Accordingly, the invention also relates to a compound of formula (I) or a pharmaceutically acceptable salt, solvate, cocrystal, tautomer, racemate, enantiomer, or diastereomer or mixture thereof, or a pharmaceutical composition comprising any of the aforementioned entities in combination with a pharmaceutically acceptable excipient, for use in the monotherapeutic treatment or prevention of cancer.

The subject or patient, such as the subject in need of treatment or prevention, may be an animal (e.g., a non-human animal), a vertebrate animal, a mammal, a rodent (e.g., a guinea pig, a hamster, a rat, a mouse), a murine (e.g., a mouse), a canine (e.g., a dog), a feline (e.g., a cat), a porcine (e.g., a pig), an equine (e.g., a horse), a primate, a simian (e.g., a monkey or ape), a monkey (e.g., a marmoset, a baboon), an ape (e.g., a gorilla, chimpanzee, orang-utan, gibbon), or a human. In the context of this invention, it is particularly envisaged that animals are to be treated which are economically, agronomically or scientifically important. Scientifically important organisms include, but are not limited to, mice, rats, and rabbits. Lower organisms such as, e.g., fruit flies like *Drosophila melanogaster* and nematodes like *Caenorhabditis elegans* may also be used in scientific approaches. Non-limiting examples of agronomically important animals are sheep, cattle and pigs, while, for example, cats and dogs may be considered as economically important animals. Preferably, the subject/patient is a mammal; more preferably, the subject/patient is a human or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orang-utan, a gibbon, a sheep, cattle, or a pig); most preferably, the subject/patient is a human.

The term "treatment" of a disorder or disease as used herein (e.g., "treatment" of cancer) is well known in the art. "Treatment" of a disorder or disease implies that a disorder or disease is suspected or has been diagnosed in a patient/subject. A patient/subject suspected of suffering from a disorder or disease typically shows specific clinical and/or pathological symptoms which a skilled person can easily attribute to a specific pathological condition (i.e., diagnose a disorder or disease). The "treatment" of a disorder or disease may, for example, lead to a halt in the progression of the disorder or disease (e.g., no deterioration of symptoms) or a delay in the progression of the disorder or disease (in case the halt in progression is of a transient nature only). The "treatment" of a disorder or disease may also lead to a partial response (e.g., amelioration of symptoms) or complete response (e.g., disappearance of symptoms) of the subject/patient suffering from the disorder or disease. Accordingly, the "treatment" of a disorder or disease may also refer to an amelioration of the disorder or disease, which may, e.g., lead to a halt in the progression of the disorder or disease or a delay in the progression of the disorder or disease. Such a partial or complete response may be followed by a relapse. It is to be understood that a subject/patient may experience a broad range of responses to a treatment (such as the exemplary responses as described herein above). The treatment of a disorder or disease may, inter alia, comprise curative treatment (preferably leading to a complete response and eventually to healing of the disorder or disease) and palliative treatment (including symptomatic relief).

The "amelioration" of a disorder or disease may, for example, lead to a halt in the progression of the disorder or disease or a delay in the progression of the disorder or disease.

The term "prevention" of a disorder or disease as used herein (e.g., "prevention" of cancer) is also well known in the art. For example, a patient/subject suspected of being prone to suffer from a disorder or disease may particularly benefit from a prevention of the disorder or disease. The subject/patient may have a susceptibility or predisposition for a disorder or disease, including but not limited to hereditary predisposition. Such a predisposition can be determined by standard methods or assays, using, e.g., genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term “prevention” comprises the use of a compound of the present invention before any clinical and/or pathological symptoms are diagnosed or determined or can be diagnosed or determined by the attending physician.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

In this specification, a number of documents including patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The present invention may be better understood with reference to the following examples. These examples are intended to be representative of specific embodiments of the invention, and are not intended as limiting the scope of the invention.

EXAMPLES

General Experimental Methods

LCMS methods:

Method A: Apparatus: Agilent 1260 Bin. Pump: G1312B, degasser; autosampler, ColCom, DAD: Agilent G1315D, 220-320 nm, MSD: Agilent LC/MSD G6130B ESI, pos/neg 100-800, ELSD Alltech 3300 gas flow 1.5 mL/min, gas temp: 40° C.; column: Waters XSelect™ C18, 30×2.1 mm, 3.5p, Temp: 35° C., Flow: 1 mL/min, Gradient: $t_0$=5% A, $t_{1.6\ min}$=98% A, $t_{3\ min}$=98% A, Posttime: 1.3 min, Eluent A: 0.1% formic acid in acetonitrile, Eluent B: 0.1% formic acid in water).

Method B: Apparatus: Agilent 1260 Bin. Pump: G1312B, degasser; autosampler, ColCom, DAD: Agilent G1315D, 220-320 nm, MSD: Agilent LC/MSD G6130B ESI, pos/neg 100-800, ELSD Alltech 3300 gas flow 1.5 mL/min, gas temp: 40° C.; column: Waters XSelect™ C18, 50×2.1 mm, 3.5μ, Temp: 35° C., Flow: 0.8 mL/min, Gradient: $t_0$=5% A, $t_{3.5\ min}$=98% A, $t_{6\ min}$=98% A, Posttime: 2 min; Eluent A: 0.1% formic acid in acetonitrile, Eluent B: 0.1% formic acid in water).

Method C: Apparatus: Agilent 1260 Bin. Pump: G1312B, degasser; autosampler, ColCom, DAD: Agilent G1315C, 220-320 nm, MSD: Agilent LC/MSD G6130B ESI, pos/neg 100-800; column: Waters XSelect™ CSH C18, 30×2.1 mm, 3.5μ, Temp: 25° C., Flow: 1 mL/min, Gradient: $t_0$=5% A, $t_{1.6\ min}$=98% A, $t_{3\ min}$=98% A, Posttime: 1.3 min, Eluent A: 95% acetonitrile+5% 10 mM ammoniumbicarbonate in water in acetonitrile, Eluent B: 10 mM ammoniumbicarbonate in water (pH=9.5).

Method D: Apparatus: Agilent 1260 Bin. Pump: G1312B, degasser; autosampler, ColCom, DAD: Agilent G1315C, 220-320 nm, MSD: Agilent LC/MSD G6130B ESI, pos/neg 100-800; column: Waters XSelect™ CSH C18, 50×2.1 mm, 3.5μ, Temp: 25° C., Flow: 0.8 mL/min, Gradient: $t_0$=5% A, $t_{3.5\ min}$=98% A, $t_{6\ min}$=98% A, Posttime: 2 min, Eluent A: 95% acetonitrile+5% 10 mM ammoniumbicarbonate in water in acetonitrile, Eluent B: 10 mM ammoniumbicarbonate in water (pH=9.5).

UPLC methods:

Method A: Apparatus: Agilent Infinity II; Bin. Pump: G7120A, Multisampler, VTC, DAD: Agilent G7117B, 220-320 nm, PDA: 210-320 nm, MSD: Agilent G6135B ESI, pos/neg 100-1000, ELSD G7102A: Evap 40° C., Neb 50° C., gasflow 1.6 mL/min, Column: Waters XSelect CSH C18, 50×2.1 mm, 2.5 μm Temp: 25° C., Flow: 0.6 mL/min, Gradient: $t_0$=5% B, $t_{2\ min}$=98% B, $t_{2.7\ min}$=98% B, Post time: 0.3 min, Eluent A: 10 mM ammonium bicarbonate in water (pH=9.5), Eluent B: acetonitrile.

Method B: Apparatus: Agilent Infinity II; Bin. Pump: G7120A, Multisampler, VTC, DAD: Agilent G7117B, 220-320 nm, PDA: 210-320 nm, MSD: Agilent G6135B ESI, pos/neg 100-1000, ELSD G7102A: Evap 40° C., Neb 40° C., gasflow 1.6 mL/min, Column: Waters XSelect™ CSH C18, 50×2.1 mm, 2.5 μm Temp: 40° C., Flow: 0.6 mL/min, Gradient: $t_0$=5% B, $t_{2\ min}$=98% B, $t_{2.7\ min}$=98% B, Post time: 0.3 min, Eluent A: 0.1% formic acid in water, Eluent B: 0.1% formic acid in acetonitrile.

GCMS methods:

Method A: Instrument: GC: Agilent 6890N G1530N and MS: MSD 5973 G2577A, El-positive, Det.temp.: 280° C. Mass range: 50-550; Column: RXi-5MS 20 m, ID 180 μm, df 0.18 μm; Average velocity: 50 cm/s; Injection vol: 1 μl; Injector temp: 250° C.; Split ratio: 100/1; Carrier gas: He; Initial temp: 100° C.; Initial time: 1.5 min; Solvent delay: 1.0 min; Rate 75° C./min; Final temp 250° C.; Hold time 4.3 min.

Method B: Instrument: GC: Agilent 6890N G1530N, FID: Det. temp: 300° C. and MS: MSD 5973 G2577A, El-positive, Det.temp.: 280° C. Mass range: 50-550; Column: Restek RXi-5MS 20 m, ID 180 μm, df 0.18 μm; Average velocity: 50 cm/s; Injection vol: 1 μl; Injector temp: 250° C.; Split ratio: 20/1; Carrier gas: He; Initial temp: 60° C.; Initial time: 1.5 min; Solvent delay: 1.3 min; Rate 50° C./min; Final temp 250° C.; Hold time 3.5 min.

Method C: Instrument: GC: Agilent 6890N G1530N, FID: Det. temp: 300° C. and MS: MSD 5973 G2577A, El-positive, Det.temp.: 280° C. Mass range: 50-550; Column: Restek RXi-5MS 20 m, ID 180 μm, df 0.18 μm; Average velocity: 50 cm/s; Injection vol: 1 μl; Injector temp: 250° C.; Split ratio: 20/1; Carrier gas: He; Initial temp: 100° C.; Initial time: 1.5 min; Solvent delay: 1.3 min; Rate 75° C./min; Final temp 250° C.; Hold time 4.5 min.

Chiral LC:

Method A: (apparatus: Agilent 1260Quart. Pump: G1311C, autosampler, ColCom, DAD: Agilent G4212B, 220-320 nm, column: Chiralcel©OD-H 250×4.6 mm, Temp: 25° C., Flow: 1 mL/min, Isocratic: 90/10, time: 30 min, Eluent A: heptane, Eluent B: ethanol).

Preparative Reversed Phase Chromatography:

Method A: Instrument type: Reveleris™ prep MPLC; Column: Phenomenex LUNA C18 (150×25 mm, 10μ); Flow: 40 mL/min; Column temp: room temperature; Eluent A: 0.1% (v/v) formic acid in water, Eluent B: 0.1% (v/v)

formic acid in acetonitrile; Gradient: t=0 min 5% B, t=1 min 5% B, t=2 min 30% B, t=17 min 70% B, t=18 min 100% B, t=23 min 100% B; Detection UV: 220/254 nm. Appropriate fractions combined and lyophilized.

Method B: Instrument type: Reveleris™ prep MPLC; Column: Waters XSelect™ CSH C18 (145×25 mm, 10μ); Flow: 40 mL/min; Column temp: room temperature; Eluent A: 10 mM ammoniumbicarbonate in water pH=9.0); Eluent B: 99% acetonitrile+1% 10 mM ammoniumbicarbonate in water; Gradient: t=0 min 5% B, t=1 min 5% B, t=2 min 30% B, t=17 min 70% B, t=18 min 100% B, t=23 min 100% B; Detection UV: 220/254 nm. Appropriate fractions combined and lyophilized.

Chiral (preparative) SFC

Method A: (Column: SFC instrument modules: Waters Prep100q SFC System, PDA: Waters 2998, Fraction Collector: Waters 2767; Column: Phenomenex Lux Amylose-1 (250×20 mm, 5 μm), column temp: 35° C.; flow: 100 mL/min; ABPR: 170 bar; Eluent A: $CO_2$, Eluent B: 20 mM ammonia in methanol; isocratic 10% B, time: 30 min, detection: PDA (210-320 nm); fraction collection based on PDA). Method B: (Column: SFC instrument modules: Waters Prep100q SFC System, PDA: Waters 2998, Fraction Collector: Waters 2767; Column: Phenomenex Lux Cellulose-1 (250×20 mm, 5 μm), column temp: 35° C.; flow: 100 mL/min; ABPR: 170 bar; Eluent A: $CO_2$, Eluent B: 20 mM ammonia in methanol; isocratic 10% B, time: 30 min, detection: PDA (210-320 nm); fraction collection based on PDA).

Method C: (Column: SFC instrument modules: Waters Prep100q SFC System, PDA: Waters 2998; Column: Chiralpak IC (100×4.6 mm, 5 μm), column temp: 35° C.; flow: 2.5 mL/min; ABPR: 170 bar; Eluent A: $CO_2$, Eluent B: methanol with 20 mM ammonia; t=0 min 5% B, t=5 min 50% B, t=6 min 50% B, detection: PDA (210-320 nm); fraction collection based on PDA).

Method D: (Column: SFC instrument modules: Waters Prep 100 SFC UV/MS directed system; Waters 2998 Photodiode Array (PDA) Detector; Waters Acquity QDa MS detector; Waters 2767 Sample Manager; Column: Waters Torus 2-PIC 130A OBD (250×19 mm, 5 μm); Column temp: 35° C.; Flow: 70 mL/min; ABPR: 120 bar; Eluent A: CO2, Eluent B: 20 mM Ammonia in Methanol; Linear gradient: t=0 min 10% B, t=4 min 50% B, t=6 min 50% B; Detection: PDA (210-400 nm); Fraction collection based on PDA TIC).

Starting Materials

Standard reagents and solvents were obtained at highest commercial purity and used as such, specific reagents purchased are described below.

| Compound name | Supplier | CAS |
|---|---|---|
| tetrakis(triphenylphosphine)palladium(0) | Sigma-Aldrich | 14221-01-3 |
| 1,1'-bis(diphenylphosphino)ferrocenepalladium(II) dichloride | Sigma-Aldrich | 72287-26-4 |
| 2-dicyclohexylphosphino-2',4',6'-triisopropyl-biphenyl | Sigma-Aldrich | 564483-18-7 |
| bis(triphenylphosphine)palladium(II) dichloride | Fluorochem | 13965-03-2 |
| 2-tributylstannylpyrazine | Combi-Blocks | 205371-27-3 |
| N-acetyl-D-leucine | Accela Chembio | 19764-30-8 |
| methyl 6-methylpiperidine-3-carboxylate | Combi-Blocks | 908245-03-4 |
| 3-bromo-5-fluoroaniline | Combi-Blocks | 134168-97-1 |
| 1-methyl-4-(tributylstannyl)-1H-imidazole | Synthonix | 446285-73-0 |
| 3-fluoro-5-iodoaniline | Combi-Blocks | 660-49-1 |
| 4-(4,4,5,5-tetramethyl-1,3,2-dioxaborolan-2-yl)-1H-pyrazol | Combi-Blocks | 269410-08-4 |
| 3-bromoaniline | Combi-Blocks | 591-19-5 |
| 1,3,5-trimethyl-4-(4,4,5,5-tetramethyl-1,3,2-dioxaborolan-2-yl)-1H-pyrazole | Combi-Blocks | 844891-04-9 |
| 3-fluoro-5-nitrobenzoic acid | Combi-Blocks | 14027-75-9 |
| acetohydrazide | Combi-Blocks | 1068-57-1 |
| N-(3-dimethylaminopropyl)-N'-ethylcarbodiimide hydrochloride | Fluorochem | 25952-53-8 |
| 1-hydroxy-7-azabenzotriazole | Enamine | 39968-33-7 |
| (methoxycarbonylsulfamoyl)triethylammonium hydroxide (Burgess reagent) | Combi-Blocks | 29684-56-8 |
| 3-nitrophenylacetylene | Combi-Blocks | 3034-94-4 |
| L-ascorbic acid sodium salt | Sigma-Aldrich | 134-03-2 |
| 2-azidopropane, 2.5M in DMF | Enamine | 691-57-6 |
| azidooxetane, 0.5M in MTBE | Enamine | 81764-67-2 |
| azidotrimethylsilane | Acros | 4648-54-8 |
| 1-fluoro-3-iodo-5-nitrobenzene | Combi-Blocks | 3819-88-3 |
| 1-bromo-3-chloro-5-nitrobenzene | Combi-Blocks | 219817-43-3 |
| 2-lodo-1-methyl-4-nitrobenzene | Fluorochem | 7745-92-8 |
| 3-bromo-5-nitrotoluene | Combi-Blocks | 52488-28-5 |
| 4-bromo-1-methyl-1,2,3-triazole | Combi-Blocks | 13273-53-5 |
| 3-nitrobenzaldehyde | Acros | 99-61-6 |
| 3-nitrophenylacetylene | Combi-Blocks | 3034-94-4 |
| chloro(pentamethylcyclopentadienyl)bis(triphenylphosphine)ruthenium(II) | STREM chemicals | 92361-49-4 |
| tetrabutylammonium fluoride 1.0M solution in THF | Fluorochem | 429-41-4 |
| 3-ethynyl-4-fluoroaniline | Synthonix | 77123-60-5 |

Intermediate 1: Synthesis of 1-((2S,5R)-5-(4-chloro-6-(pyrazin-2-yl)pyrimidin-2-yl)-2-methylpiperidin-1-yl)ethan-1-one

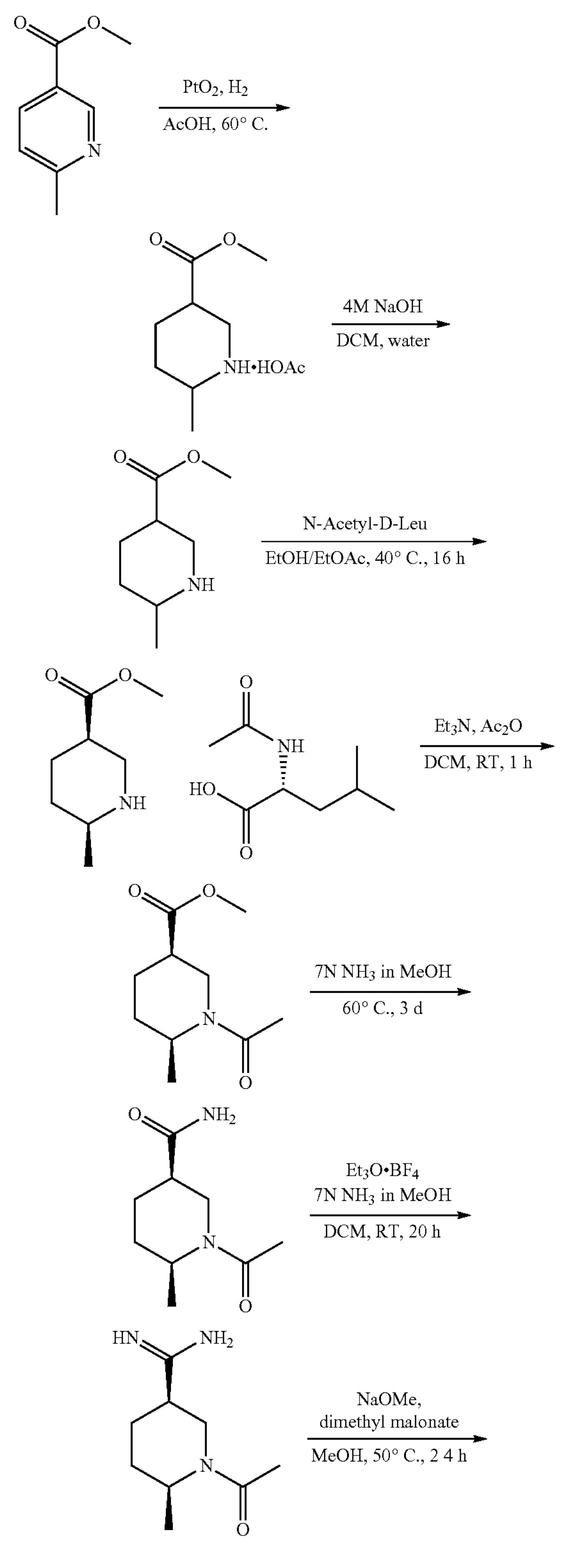

-continued

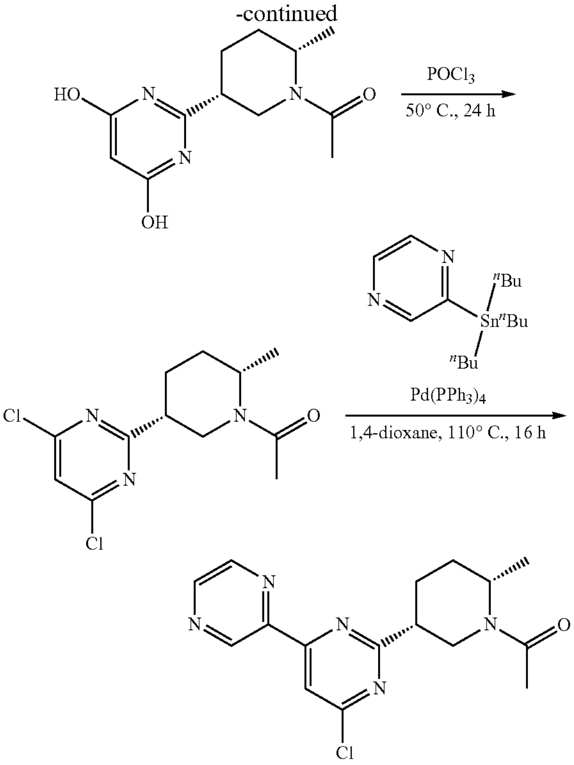

To a solution of methyl 6-methylnicotinate (100 g, 662 mmol) in acetic acid (250 mL) in a 1 L steel autoclave, platinum(IV) oxide (0.5 g, 2.202 mmol) was added after which the reaction mixture was stirred under 10 bar hydrogen atmosphere at 60° C. Rapid hydrogen consumption was observed and the autoclave was refilled several times until hydrogen consumption stopped. The mixture was cooled to room temperature and filtered over Celite. The filtrate was carefully concentrated to afford methyl 6-methylpiperidine-3-carboxylate acetate as a mixture of diastereoisomers (143.8 g, 100%) that was used as such in the next step. GCMS (Method A): $t_R$ 2.40 (80%) and 2.48 min (20%), 100%, MS (EI) 157.1 $(M)^+$. Methyl 6-methylpiperidine-3-carboxylate acetate as a mixture of diastereoisomers (2.1 kg, 9924 mmol) was diluted with dichloromethane (4 L) and 4M sodium hydroxide solution was added slowly until pH 9. The layers were separated and the aqueous layer was extracted with dichloromethane twice (the aqueous layer was re-basified with 4M sodium hydroxide solution to pH~9 after each extraction). The combined organic layers were dried with sodium sulfate and concentrated (35° C., 450 mbar) to a smaller volume (~2 L) to afford methyl 6-methylpiperidine-3-carboxylate (2.8 kg, 8905 mmol) as a ~50% yellow solution in dichloromethane. $^1H$ NMR (400 MHz, $CDCl_3$, mixture of rotamers) δ 5.10 (s, 3H), 3.63 (s, 1H), 3.49-3.42 (m, 2.2H), 3.41-3.34 (m, 0.8H), 3.18-3.10 (m, 0.8H), 3.09-3.03 (m, 0.2H), 2.64-2.54 (m, 0.8H), 2.53-2.34 (m, 1.2H), 2.30-2.20 (m, 1H), 1.95-1.76 (m, 1H), 1.53-1.36 (m, 1H), 1.35-1.21 (m, 1H), 1.04-0.90 (m, 1H), 0.89-0.84 (m, 0.8H), 0.83-0.76 (m, 2.2H). To a solution of N-acetyl-D-leucine (1 kg, 5.77 mol) in ethanol (1.5 L) was added a solution of methyl 6-methylpiperidine-3-carboxylate (934 g, 2.38 mol) in ethyl acetate (3 L) and the mixture was heated to 40° C. The resulting solution was allowed to reach room temperature over 16 hours during which precipitation occurred. The precipitate was filtered off, washed with diethyl ether (500 mL) and air dried to afford crude methyl (3R,6S)-6-methylpiperidine-3-carboxylate acetyl-D-leucinate (287 g, 34%) as a white solid. The crude methyl (3R,6S)-6-methylpiperidine-3-carboxylate acetyl-D-leucinate (287 g, 869 mmol) was crystallized from a hot mixture of ethanol and ethyl acetate 1:2 (1 L). The precipitate was filtered off and the filter cake was triturated in a mixture of diethyl ether and n-pentane 1:1 (500 mL). The precipitate was filtered off and air dried to afford methyl (3R,6S)-6-methylpiperidine-3-carboxylate acetyl-D-leucinate (128 g, 44%) as a white solid. $^{1}$H-NMR (400 MHz, DMSO-d6) δ 7.80 (d, J=8.2 Hz, 1H), 5.80-5.00 (s, 2H), 4.20-4.04 (m, 1H), 3.63 (s, 3H), 3.32-3.21 (m, 1H), 2.93-2.80 (m, 2H), 2.73-2.65 (m, 1H), 2.04-1.94 (m, 1H), 1.82 (s, 3H), 1.68-1.49 (m, 3H), 1.49-1.37 (m, 2H), 1.30-1.15 (m, 1H), 1.02 (d, J=6.4 Hz, 3H), 0.85 (m, 6H). To a solution of methyl (3R,6S)-6-methylpiperidine-3-carboxylate acetyl-D-leucinate (128 g, 387 mmol) in dichloromethane (1 L) was added a saturated sodium carbonate solution (1 L). The biphasic system was stirred vigorous for 10 minutes and the layers were separated. The organic layer was dried with sodium sulfate and filtered to afford a clear solution. Next, triethylamine (65 mL, 465 mmol) and acetic anhydride (44 mL, 465 mmol) were added and the mixture was stirred at room temperature for 1 hour. The mixture was washed with saturated aqueous sodium bicarbonate solution, dried over sodium sulfate and concentrated to afford methyl (3R,6S)-1-acetyl-6-methylpiperidine-3-carboxylate (93 g) as a light yellow solid. $^{1}$H-NMR (400 MHz, $CDCl_3$, mixture of rotamers) δ 5.02-4.87 (m, 0.5H), 4.84-4.68 (m, 0.5H), 4.18-4.05 (m, 0.5H), 3.89-3.77 (m, 0.5H), 3.71 (d, J=11.6 Hz, 3H), 3.31-3.18 (m, 0.5H), 2.79-2.67 (m, 0.5H), 2.51-2.31 (m, 1H), 2.11 (d, J=6.7 Hz, 3H), 2.01-1.90 (m, 1H), 1.88-1.55 (m, 3H), 1.33-1.21 (m, 1.5H), 1.20-1.06 (m, 1.5H). An autoclave was charged with methyl (3R,6S)-1-acetyl-6-methylpiperidine-3-carboxylate (93 g, 387 mmol) in 7N ammonia in methanol (600 mL, 4200 mmol) and was heated to 60° C. for 3 days. The mixture was concentrated to afford (3R,6S)-1-acetyl-6-methylpiperidine-3-carboxamide (102 g) as a pale yellow oil. Assuming quantitative yield, the product was used as such in the next step. $^{1}$H-NMR (400 MHz, DMSO-d6, mixture of rotamers) δ 7.38 (s, 1H), 6.89 (d, J=24.7 Hz, 1H), 4.76-4.59 (m, 0.5H), 4.39-4.24 (m, 0.5H), 4.16-4.01 (m, 0.5H), 3.72-3.51 (m, 0.5H), 3.14-2.99 (m, 0.5H), 2.68-2.51 (m, 0.5H), 2.30-2.12 (m, 0.5H), 2.11-1.92 (m, 3.5H), 1.78-1.38 (m, 4H), 1.23-1.11 (m, 1.5H), 1.09-0.94 (m, 1.5H); Chiral LC (Method A) $t_R$=12.35 min, >98% ee. To a solution of (3R,6S)-1-acetyl-6-methylpiperidine-3-carboxamide (50 g, 271 mmol) in dichloromethane (500 mL) was added triethyloxonium tetrafluoroborate (77 g, 407 mmol) portion wise and the mixture was stirred at room temperature for 4 hours. Slowly, 7N ammonia in methanol (200 mL, 9.15 mol) was added and the mixture was stirred at room temperature for 16 hours. The mixture was concentrated to afford (3R,6S)-1-acetyl-6-methylpiperidine-3-carboximidamide (50 g) as a pink solid which was used as such in the next step. To a solution of 5.4M sodium methoxide in methanol (99 mL, 535 mmol) in methanol (200 mL) was added, (3R,6S)-1-acetyl-6-methylpiperidine-3-carboximidamide (49 g, 267 mmol) in methanol (400 mL) and dimethyl malonate (61.4 mL, 535 mmol). The mixture was heated to 50° C. and stirred for 24 hours. The mixture was acidified (pH ~3) with concentrated hydrochloric acid and was concentrated to a smaller volume. The residue was filtered through silica (20% methanol in dichloromethane) and concentrated to afford an orange oil. The crude product was purified with silica column chromatography (0% to 20% methanol in dichloromethane) to afford 1-((2S,5R)-5-(4,6-dihydroxypyrimidin-2-yl)-2-methylpiperidin-1-yl)ethan-1-one (12 g, 17%) as a colorless gum. LCMS (Method C): $t_R$ 0.17 min, 100%, MS (ESI) 252.1 $(M+H)^+$. A solution of 1-((2S,5R)-5-(4,6-dihydroxypyrimidin-2-yl)-2-methylpiperidin-1-yl)ethan-1-one (12 g, 47.8 mmol) in phosphorus oxychloride (80 mL, 858 mmol) was stirred at 60° C. for 24 hours. The reaction mixture was concentrated and co-evaporated with toluene twice to afford a yellow oil. The oil was dissolved in ethyl acetate and washed with saturated sodium bicarbonate solution. The aqueous layer was extracted with ethyl acetate twice. The combined organic layers were washed with brine, dried over sodium sulfate and concentrated to afford a yellow oil. The oil was purified with silica column chromatography (0% to 20% tetrahydrofuran in toluene) to afford 1-((2S,5R)-5-(4,6-dichloropyrimidin-2-yl)-2-methylpiperidin-1-yl)ethan-1-one (1.5 g, 11%) as a colorless gum. $^{1}$H-NMR (400 MHz, DMSO-d6, mixture of rotamers) δ 7.95 (d, J=7.3 Hz, 1H), 4.85-4.72 (m, 1H), 4.69-4.62 (m, 1H), 4.23-4.13 (m, 1H), 4.07-3.98 (m, 1H), 3.97-3.88 (m, 1H), 3.00-2.89 (m, 1H), 2.81-2.67 (m, 1H), 2.09-1.72 (m, 7H), 1.71-1.58 (m, 2H), 1.25-1.14 (m, 3H), 1.12-1.05 (m, 2H); LCMS (Method B): $t_R$ 3.34 min, MS (ESI) 288.0 $(M+H)^+$; Chiral UPLC (Method: A) $t_R$ 2.54 min, >95% ee and de. Under argon, 2-tributylstannylpyrazine (607 mg, 1.65 mmol), 1-((2S,5R)-5-(4,6-dichloropyrimidin-2-yl)-2-methylpiperidin-1-yl)ethan-1-one (500 mg, 1.74 mmol) and bis (triphenylphosphine)palladium(II) chloride (244 mg, 0.34 mmol) in 1,4-dioxane (20 mL) were heated to 100° C. and stirred for 32 hours. The mixture was diluted with dichloromethane containing 1% triethylamine and coated onto silica. This was purified with silica column chromatography (0% to 40% acetonitrile in dichloromethane containing 1% triethylamine) to afford 1-((2S,5R)-5-(4-chloro-6-(pyrazin-2-yl)pyrimidin-2-yl)-2-methylpiperidin-1-yl)ethan-1-one (Intermediate 1, 134 mg, 18%) as an orange gum. $^{1}$H-NMR (400 MHz, DMSO-d6, mixture of rotamers) δ 9.46-9.41 (m, 1H), 8.80-8.76 (m, 1H), 8.65-8.59 (m, 1H), 8.33-8.29 (m, 1H), 7.66-7.59 (m, 1H), 4.86-4.70 (m, 0.5H), 4.27-4.17 (m, 0.5H), 4.09-3.97 (m, 0.5H), 3.55-3.41 (m, 0.5H), 3.06-2.98 (m, 0.5H), 2.88-2.82 (m, 0.5H), 2.10-1.90 (m, 6H), 1.89-1.76 (m, 0.5H), 1.75-1.61 (m, 1.5H), 1.29-1.20 (m, 1.5H), 1.17-1.10 (m, 1.5H); LCMS (Method C): $t_R$ 1.81 min, MS (ESI) 331.1 $(M+H)^+$.

Synthetic Procedures for Final Products

Example 1: Synthesis of 1-((2S,5R)-5-(4-((3-fluoro-5-(1-methyl-1H-imidazol-4-yl)phenyl)amino)-6-(pyrazin-2-yl)pyrimidin-2-yl)-2-methylpiperidin-1-yl)ethan-1-one (001)

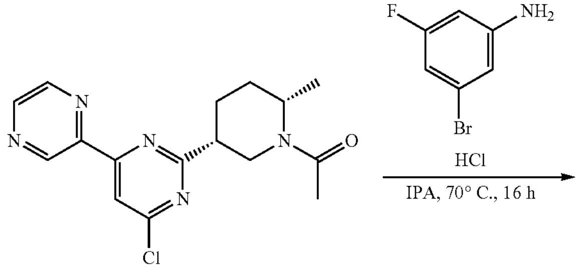

-continued

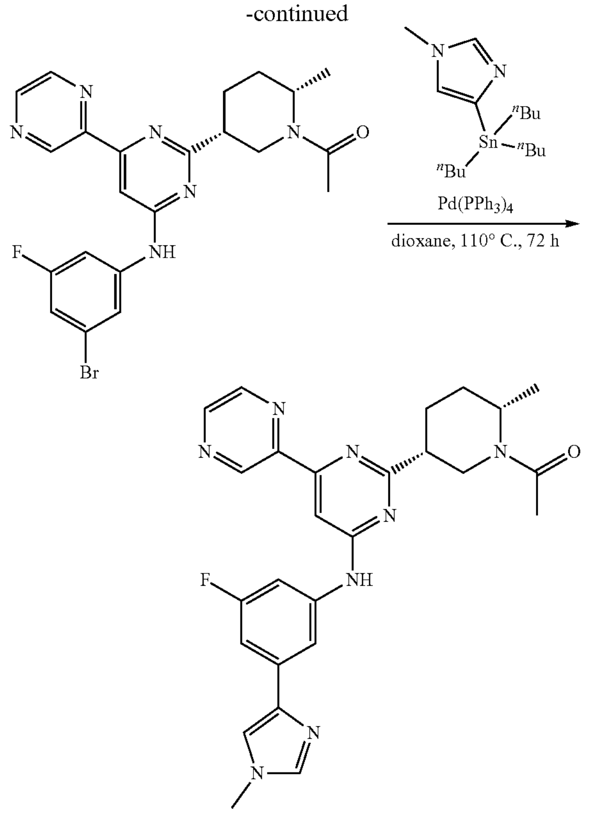

001

To a mixture of 1-((2S,5R)-5-(4-chloro-6-(pyrazin-2-yl)pyrimidin-2-yl)-2-methylpiperidin-1-yl)ethan-1-one (Intermediate 1, 4.64 g, 8.95 mmol) in 2-propanol (60 mL) were added 3-bromo-5-fluoroaniline (2.21 g, 11.63 mmol) and concentrated hydrochloric acid (1.49 mL, 17.90 mmol). The mixture was stirred at 60° C. for 4 days and at room temperature for 1 day. The mixture was neutralized to pH 7 using saturated aqueous sodium bicarbonate solution and concentrated in vacuo. The residue was extracted three times with ethyl acetate and twice with a mixture of 10% methanol in dichloromethane. The combined organic layers were dried over sodium sulfate, filtered and coated onto silica. The residue was purified by silica column chromatography (0% to 10% methanol in dichloromethane), to afford 1-((2S,5R)-5-(4-((3-bromo-5-fluorophenyl)amino)-6-(pyrazin-2-yl)pyrimidin-2-yl)-2-methylpiperidin-1-yl)ethan-1-one (2.58 g, 56%) as an off-white solid. LCMS (Method C): $t_R$ 2.02 min, 94%, MS (ESI) 485.0 and 487.0 $(M+H)^+$. Under nitrogen atmosphere, 1-((2S,5R)-5-(4-((3-bromo-5-fluorophenyl)amino)-6-(pyrazin-2-yl)pyrimidin-2-yl)-2-methylpiperidin-1-yl)ethan-1-one (2.88 g, 5.70 mmol) and 1-methyl-4-(tributylstannyl)-1H-imidazole (2.54 g, 6.84 mmol) were dissolved in dry 1,4-dioxane (55 mL) and tetrakis(triphenylphosphine)palladium(0) (1.32 g, 1.14 mmol) was added. The mixture was stirred at 110° C. for 3 days, allowed to cool to room temperature and coated onto silica. The coated mixture was purified by silica column chromatography (0% to 10% methanol in dichloromethane) twice. The product was further purified by preparative reversed phase chromatography (Method A) and concentrated in vacuo. The residue was extracted three times with ethyl acetate, the combined organic layers were dried over sodium sulfate, filtered and dried in vacuo. The residue was purified by chiral (preparative) SFC (Method D) and lyophilized to afford 1-((2S,5R)-5-(4-((3-fluoro-5-(1-methyl-1H-imidazol-4-yl)phenyl)amino)-6-(pyrazin-2-yl)pyrimidin-2-yl)-2-methylpiperidin-1-yl)ethan-1-one (001, 1.21 g, 44%) as a white solid. $^1$H-NMR (400 MHz, DMSO-d6, mixture of rotamers) δ 10.14 (d, J=8.5 Hz, 1H), 9.56 (d, J=12.7 Hz, 1H), 8.84-8.78 (m, 2H), 7.98 (d, J=6.0 Hz, 1H), 7.76-7.62 (m, 4H), 7.22-7.14 (m, 1H), 4.88-4.73 (m, 1H), 4.28-4.19 (m, 0.5H), 4.09 (dd, J=13.6, 4.1 Hz, 0.5H), 3.75-3.66 (m, 3H), 3.57-3.47 (m, 0.5H), 3.02-2.89 (m, 1H), 2.85-2.74 (m, 0.5H), 2.14-2.00 (m, 5H), 1.93-1.82 (m, 0.5H), 1.77-1.65 (m, 1.5H), 1.33-1.27 (m, 1.5), 1.19-1.13 (m, 1.5H); UPLC (Method A): $t_R$ 1.45 min, 97%, MS (ESI) 487.2 $(M+H)^+$.

Example 2: Synthesis of 1-((2S,5R)-5-(4-((3-fluoro-5-(1H-pyrazol-4-yl)phenyl)amino)-6-(pyrazin-2-yl)pyrimidin-2-yl)-2-methylpiperidin-1-yl)ethan-1-one (002)

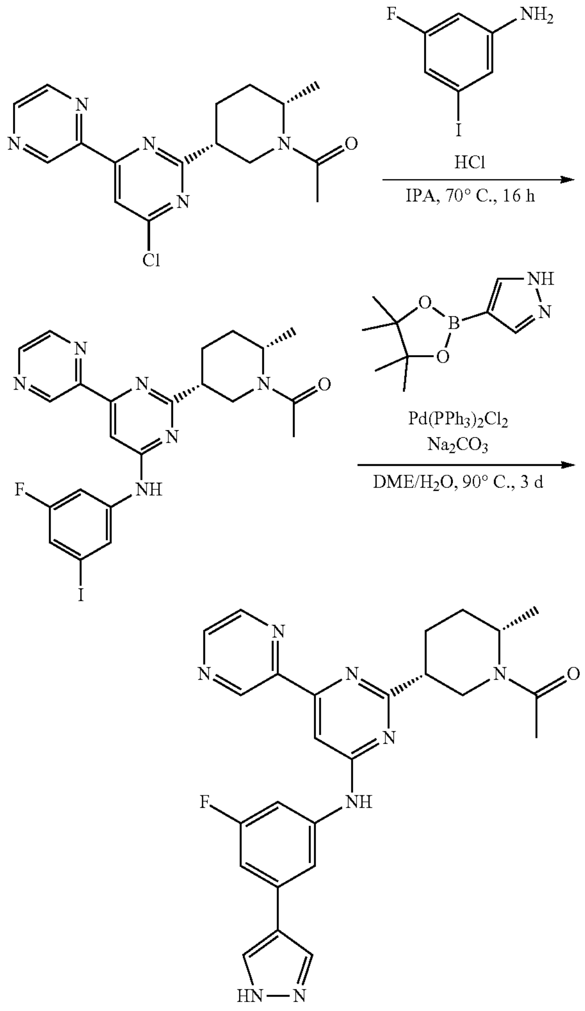

002

To a mixture of 1-((2S,5R)-5-(4-chloro-6-(pyrazin-2-yl)pyrimidin-2-yl)-2-methylpiperidin-1-yl)ethan-1-one (Intermediate 1, 457 mg, 1.38 mmol) and 3-fluoro-5-iodoaniline (326 mg, 1.38 mmol) in 2-propanol (10 mL) was added concentrated hydrochloric acid (0.23 mL, 2.75 mmol). The mixture was stirred at 60° C. for 16 hours. The mixture was concentrated in vacuo, redissolved in water, neutralized with saturated aqueous sodium bicarbonate solution and extracted with ethyl acetate three times. The combined organic layers were dried over sodium sulfated, filtered and coated onto silica. The residue was purified by silica column chromatography (0% to 100% ethyl acetate in n-heptane) followed by silica column chromatography (0% to 10% methanol in dichloromethane) to afford 1-((2S,5R)-5-(4-((3-fluoro-5-iodophenyl)amino)-6-(pyrazin-2-yl)pyrimidin-2-yl)-2-methylpiperidin-1-yl)ethan-1-one (403 mg, 47%) as an off-white solid. LCMS (Method C): $t_R$ 2.20 min, 86%, MS (ESI) 533.0 $(M+H)^+$. Under nitrogen atmosphere, 1-((2S,5R)-5-(4-((3-fluoro-5-iodophenyl)amino)-6-(pyrazin-2-yl)pyrimidin-2-yl)-2-methylpiperidin-1-yl) ethan-1-one (50 mg, 0.09 mmol), 4-(4,4,5,5-tetramethyl-1,3,2-dioxaborolan-2-yl)-1H-pyrazole (54.7 mg, 0.28 mmol) and sodium carbonate (29.9 mg, 0.28 mmol) were dissolved in 1,2-dimethoxyethane (1 mL) and water (0.33 mL) and 1,1'-bis(diphenylphosphino)ferrocenepalladium(II)dichloride dichloromethane complex (7.67 mg, 9.39 μmol) was added. The mixture was stirred at 90° C. for 3 days. The reaction mixture was allowed to cool to room temperature, filtered over C18-material, coated onto silica and purified by silica column chromatography (0% to 10% methanol in dichloromethane). The product was further purified by preparative reversed phase chromatography (Method B) and lyophilized to afford 1-((2S,5R)-5-(4-((3-fluoro-5-(1H-pyrazol-4-yl)phenyl)amino)-6-(pyrazin-2-yl)pyrimidin-2-yl)-2-methylpiperidin-1-yl)ethan-1-one (002, 20.0 mg, mmol, 45%) as a white solid. $^1$H-NMR (400 MHz, DMSO-d6, mixture of rotamers) δ 13.06 (s, 1H), 10.13 (d, J=7.8 Hz, 1H), 9.56 (d, J=14.3 Hz, 1H), 8.91-8.70 (m, 2H), 8.33-7.82 (m, 2H), 7.73-7.61 (m, 3H), 7.21-7.09 (m, 1H), 4.88-4.72 (m, 1H), 4.28-4.18 (m, 0.5H), 4.18-4.01 (m, 0.5H), 3.53-3.43 (m, 0.5H), 3.01-2.89 (m, 1H), 2.85-2.74 (m, 0.5H), 2.13-2.00 (m, 5H), 1.93-1.82 (m, 0.5H), 1.78-1.63 (m, 1.5H), 1.31-1.23 (m Hz, 1.5H), 1.19-1.09 (m 1.5H); UPLC (Method A): $t_R$ 1.44 min, 99%, MS (ESI) 473.2 $(M+H)^+$.

Example 3: Synthesis of 1-((2S,5R)-5-(4-((3-fluoro-5-(1,3,5-trimethyl-1H-pyrazol-4-yl)phenyl)amino)-6-(pyrazin-2-yl)pyrimidin-2-yl)-2-methylpiperidin-1-yl)ethan-1-one (003)

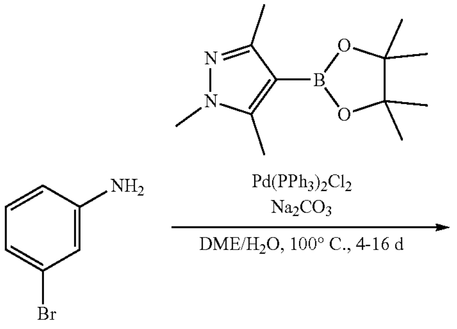

-continued

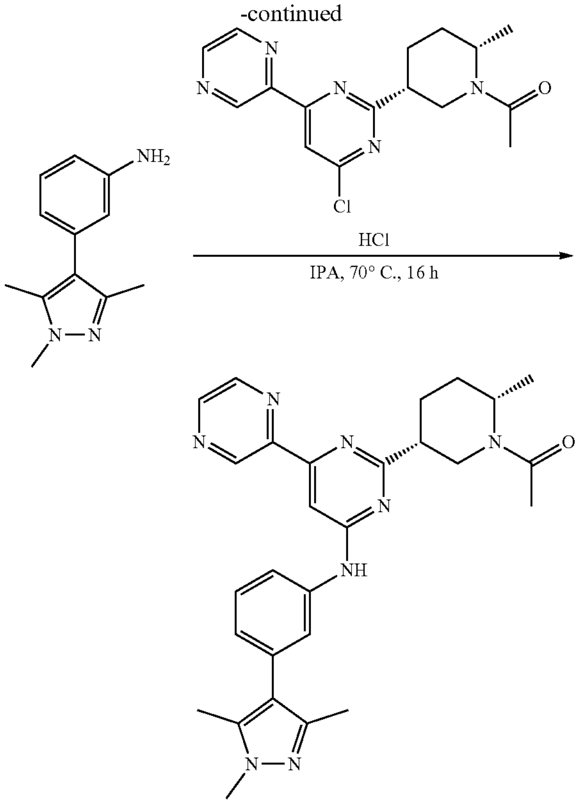

003

A mixture of 3-bromoaniline (0.13 mL, 1.16 mmol), 1,3,5-trimethyl-4-(4,4,5,5-tetramethyl-1,3,2-dioxaborolan-2-yl)-1H-pyrazole (302 mg, 1.28 mmol) and sodium carbonate (370 mg, 3.49 mmol) in 1,2-dimethoxyethane (8 mL) and water (2 mL) was degassed with argon for 5 minutes.

Bis(triphenylphosphine)palladium(II) dichloride (40.8 mg, 0.06 mmol) was added and the mixture was heated at 100° C. for 16 hours. The mixture was allowed to cool to room temperature, diluted with water and extracted with ethyl acetate three times. The combined organic layers were washed with brine, dried over sodium sulfate, filtered and concentrated in vacuo. The residue was purified by silica column chromatography (0% to 75% ethyl acetate in n-heptane) to afford 3-(1,3,5-trimethyl-1H-pyrazol-4-yl)aniline (100 mg, 43%) as a yellow oil. $^1$H-NMR (400 MHz, DMSO-d6) δ 7.05-6.99 (m, 1H), 6.48-6.42 (m, 2H), 6.38-6.33 (m, 1H), 5.03 (s, 2H), 3.67 (s, 3H), 2.18 (s, 3H), 2.09 (s, 3H). To a mixture of 1-((2S,5R)-5-(4-chloro-6-(pyrazin-2-yl)pyrimidin-2-yl)-2-methylpiperidin-1-yl)ethan-1-one (Intermediate 1, 100 mg, 0.25 mmol) and 3-(1,3,5-trimethyl-1H-pyrazol-4-yl)aniline (60.4 mg, 0.30 mmol) in 2-propanol (4 mL) was added concentrated hydrochloric acid (0.02 mL, 0.25 mmol). The mixture was stirred at 70° C. for 16 hours, allowed to cool to room temperature and was concentrated in vacuo. The residue was dissolved in methanol and purified by chiral (preparative) SFC (Method D) and lyophilized to afford 1-((2S,5R)-2-methyl-5-(4-(pyrazin-2-yl)-6-((3-(1,3,5-trimethyl-1H-pyrazol-4-yl)phenyl)amino)pyrimidin-2-yl)piperidin-1-yl)ethan-1-one (003, 68.2 mg, 55%) as a white solid. $^1$H-NMR (400 MHz, DMSO-d6, mixture of rotamers) δ 9.94 (d, J=7.5 Hz, 1H), 9.55 (dd, J=13.0, 1.3 Hz, 1H), 8.98-8.65 (m, 2H), 7.87-7.71 (m, 1H), 7.66 (d, J=2.1 Hz, 1H), 7.62-7.50 (m, 1H), 7.43-7.35 (m, 1H), 6.94 (d, J=7.5 Hz, 1H), 4.86-4.76 (m, 0.5H), 4.71-4.61 (m, 0.5H), 4.25-4.14 (m, 0.5H), 4.06-3.96 (m, 0.5H), 3.70 (s, 3H), 3.52-3.41 (m, 0.5H), 2.96-2.81 (m, 1H), 2.77-2.68 (m, 0.5H), 2.25 (s, 3H), 2.16 (s, 3H), 2.11-1.90 (m, 5H), 1.90-1.76 (m, 0.5H), 1.74-1.58 (m, 1.5H), 1.22-1.16 (m, 1.5H), 1.11-1.04 (m, 1.5H); UPLC (Method A): $t_R$ 1.50 min, 99%, MS (ESI) 497.4 $(M+H)^+$.

The following compounds were prepared following procedures analogous to Example 3, using the appropriate starting materials, and purified using reversed phase chromatography method A/B and/or prep-SFC.

| Compound # | Structure and compound name | Analytical data |
| --- | --- | --- |
| 004 | 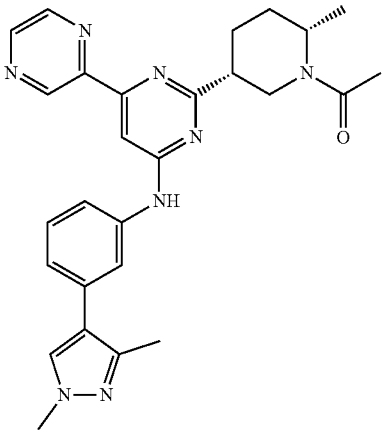 1-((2S,5R)-5-(4-((3-(1,3-dimethyl-1H-pyrazol-4-yl)phenyl)amino)-6-(pyrazin-2-yl)pyrimidin-2-yl)-2-methylpiperidin-1-yl)ethan-1-one | $^1$H-NMR (400 MHz, DMSO-d6, mixture of rotamers) δ 9.93 (d, J = 8.7 Hz, 1H), 9.56 (dd, J = 12.1, 1.3 Hz, 1H), 8.83-8.77 (m, 2H), 7.96 (d, J = 12.9 Hz, 1H), 7.87 (d, J = 8.4 Hz, 1H), 7.66 (d, J = 1.7 Hz, 1H), 7.58-7.47 (m, 1H), 7.36 (td, J = 7.9, 2.4 Hz, 1H), 7.10 (d, J = 7.4 Hz, 1H), 4.87-4.70 (m, 1H), 4.28-4.17 (m, 0.5H), 4.06-3.98 (m, 0.5H), 3.79 (d, J = 4.4 Hz, 3H), 3.53-3.43 (m, 0.5H), 2.97-2.83 (m, 1H), 2.79-2.69 (m, 0.5H), 2.32 (s, 3H), 2.12-1.90 (m, 5H), 1.90-1.77 (m, 0.5H), 1.75-1.60 (m, 1.5H), 1.26-1.20 (m, 1.5H), 1.13-1.07 (m, 1.5H); UPLC (Method A): $t_R$ 1.36 min, 100%, MS (ESI) 483.2 $(M + H)^+$. |
| 005 | 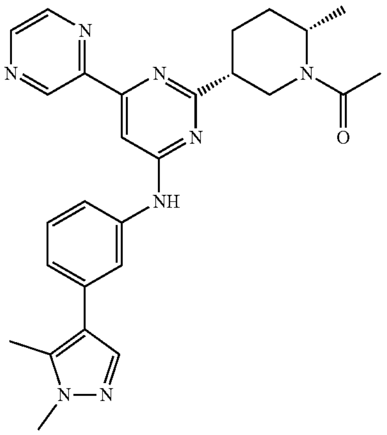 1-((2S,5R)-5-(4-((3-(1,5-dimethyl-1H-pyrazol-4-yl)phenyl)amino)-6-(pyrazin-2-yl)pyrimidin-2-yl)-2-methylpiperidin-1-yl)ethan-1-one | $^1$H-NMR (400 MHz, DMSO-d6, mixture of rotamers) δ 9.95 (d, J = 7.0 Hz, 1H), 9.55 (dd, J = 13.5, 1.2 Hz, 1H), 8.83-8.76 (m, 2H), 7.96-7.85 (m, 1H), 7.66 (d, J = 2.1 Hz, 1H), 7.61-7.51 (m, 2H), 7.38 (td, J = 7.8, 1.8 Hz, 1H), 7.08 (d, J = 7.6 Hz, 1H), 4.86-4.76 (m, 0.5H), 4.75-4.67 (m, 0.5H), 4.26-4.16 (m, 0.5H), 4.07-3.98 (m, 0.5H), 3.79 (s, 3H), 3.53-3.43 (m, 0.5H), 2.97-2.83 (m, 1H), 2.78-2.70 (m, 0.5H), 2.41 (s, 3H), 2.13-1.92 (m, 5H), 1.92-1.77 (m, 0.5H), 1.75-1.60 (m, 1.5H), 1.26-1.18 (m, 1.5H), 1.13-1.05 (m, 1.5H); UPLC (Method A): $t_R$ 1.37 min, 100%, MS (ESI) 483.2 $(M + H)^+$. |

Example 4: Synthesis of 1-((2S,5R)-5-(4-((3-fluoro-5-(5-methyl-1,3,4-oxadiazol-2-yl)phenyl)amino)-6-(pyrazin-2-yl)pyrimidin-2-yl)-2-methylpiperidin-1-yl)ethan-1-one (006)

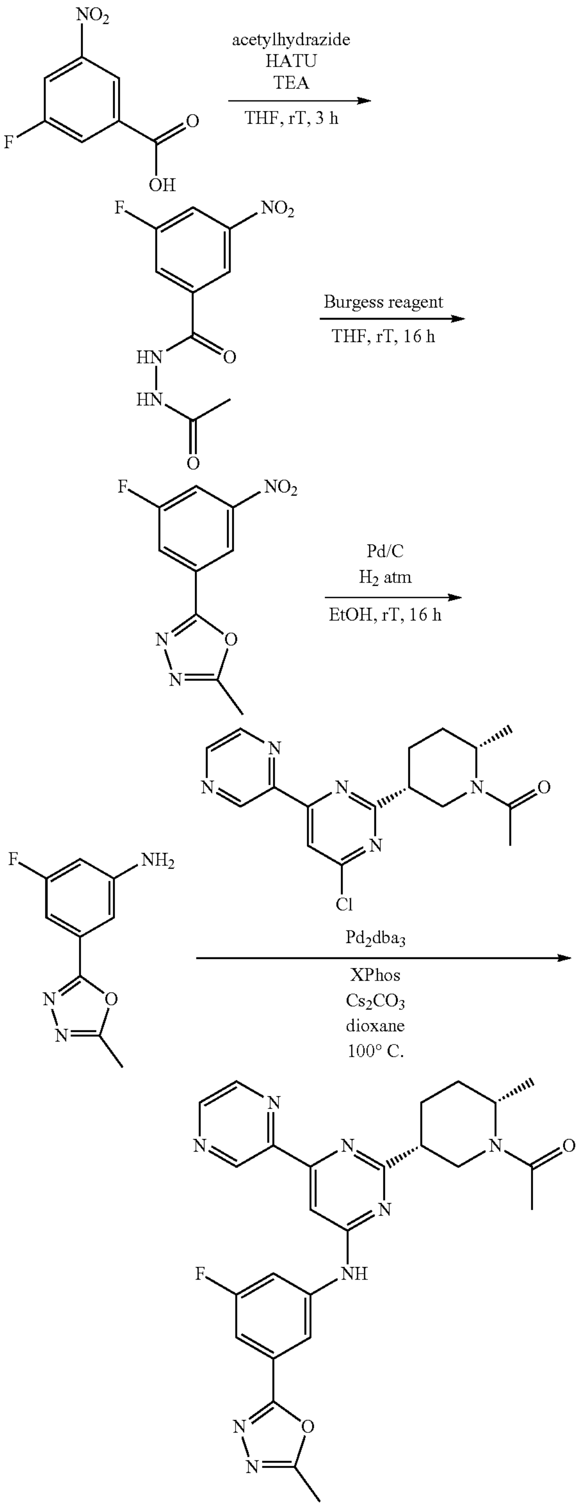

006

To a mixture of 3-fluoro-5-nitrobenzoic acid (200 mg, 1.08 mmol) and acetohydrazide (96 mg, 1.30 mmol) in dry N,N-dimethylformamide (10 mL) were added N-(3-dimethylaminopropyl)-N'-ethylcarbodiimide hydrochloride (249 mg, 1.30 mmol) and 1-hydroxy-7-azabenzotriazole (14.71 mg, 0.11 mmol). The mixture was stirred at room temperature for 3 days. The reaction mixture was diluted with ethyl acetate and saturated aqueous sodium bicarbonate solution. The layers were separated and the organic layer was washed with saturated aqueous sodium bicarbonate solution. The organic layer was dried over sodium sulfate, filtered and dried in vacuo. The residue was dissolved in dry tetrahydrofuran (10 mL) and (methoxycarbonylsulfamoyl)triethylammonium hydroxide (643 mg, 2.70 mmol) was added. The mixture was stirred at room temperature for 90 minutes and subsequently diluted with ethyl acetate and saturated aqueous sodium bicarbonate solution. The layers were separated and the aqueous phase was extracted twice with ethyl acetate. The combined organic layers were dried over sodium sulfate, filtered and coated onto silica. The residue was purified by silica column chromatography (0% to 100% ethyl acetate in n-heptane) to afford 2-(3-fluoro-5-nitrophenyl)-5-methyl-1,3,4-oxadiazole (131 mg, 54%) as a yellow oil. $^1$H-NMR (400 MHz, DMSO-d6) δ 8.53-8.47 (m, 1H), 8.44-8.37 (m, 1H), 8.32-8.25 (m, 1H), 2.63 (s, 3H); LCMS (Method A): $t_R$ 1.73 min, 99%, MS (ESI) 224.0 $(M+H)^+$. Under nitrogen atmosphere, 2-(3-fluoro-5-nitrophenyl)-5-methyl-1,3,4-oxadiazole (130 mg, 0.58 mmol) was dissolved in ethanol (5 mL) and 10% palladium on carbon (50% wet, 12.40 mg, 0.06 mmol) was added. Next, hydrogen atmosphere was introduced and the mixture was stirred at room temperature for 16 hours. The mixture was filtered over Celite, the filter cake was washed with ethanol and the filtrate was coated onto silica. The residue was purified by column chromatography (0% to 10% methanol in dichloromethane) to afford 3-fluoro-5-(5-methyl-1,3,4-oxadiazol-2-yl)aniline (76 mg, 68%) as a dark gum. $^1$H-NMR (400 MHz, DMSO-d6) δ 7.05-7.00 (m, 1H), 6.82-6.75 (m, 1H), 6.55-6.47 (m, 1H), 5.87 (s, 2H), 2.56 (s, 3H). Under nitrogen atmosphere, 1-((2S,5R)-5-(4-chloro-6-(pyrazin-2-yl)pyrimidin-2-yl)-2-methylpiperidin-1-yl)ethan-1-one (Intermediate 1, 50 mg, 0.15 mmol), 3-fluoro-5-(5-methyl-1,3,4-oxadiazol-2-yl)aniline (37.8 mg, 0.20 mmol) and cesium carbonate (147 mg, 0.45 mmol) were dissolved in 1,4-dioxane (2 mL) and tris(dibenzylideneacetone)dipalladium (0) (13.80 mg, 0.02 mmol) and 2-dicyclohexylphosphino-2',4',6'-triisopropylbiphenyl (14.37 mg, 0.03 mmol) were added. The mixture was heated in a microwave at 100° C. for 2 hours. The mixture was filtered over C18-material, purified by preparative reversed phase chromatography (Method A) and lyophilized to afford 1-((2S,5R)-5-(4-((3-fluoro-5-(5-methyl-1,3,4-oxadiazol-2-yl)phenyl)amino)-6-(pyrazin-2-yl)pyrimidin-2-yl)-2-methylpiperidin-1-yl) ethan-1-one (006, 40 mg, 54%) as a white solid. $^1$H-NMR (400 MHz, DMSO-d6, mixture of rotamers) δ 10.42 (d, J=6.4 Hz, 1H), 9.56 (d, J=14.4 Hz, 1H), 8.85-8.78 (m, 2H), 8.38-8.30 (m, 1H), 8.06-7.95 (m, 1H), 7.68 (d, J=3.1 Hz, 1H), 7.43-7.34 (m, 1H), 4.88-4.74 (m, 1H), 4.28-4.21 (m, 0.5H), 4.18-4.07 (m, 0.5H), 3.56-3.45 (m, 0.5H), 3.03-2.91 (m, 1H), 2.86-2.72 (m, 0.5H), 2.59 (s, 3H), 2.19-1.98 (m, 5H), 1.93-1.82 (m, 0.5H), 1.77-1.65 (m, 1.5H), 1.34-1.23 (m, 1.5H), 1.22-1.12 (m, 1.5H); UPLC (Method B): $t_R$ 1.49 min, 100%, MS (ESI) 489.2 $(M+H)^+$.

Example 5: Synthesis of 1-((2S,5R)-5-(4-((3-(1-isopropyl-1H-1,2,3-triazol-4-yl)phenyl)amino)-6-(pyrazin-2-yl)pyrimidin-2-yl)-2-methylpiperidin-1-yl)ethan-1-one (007)

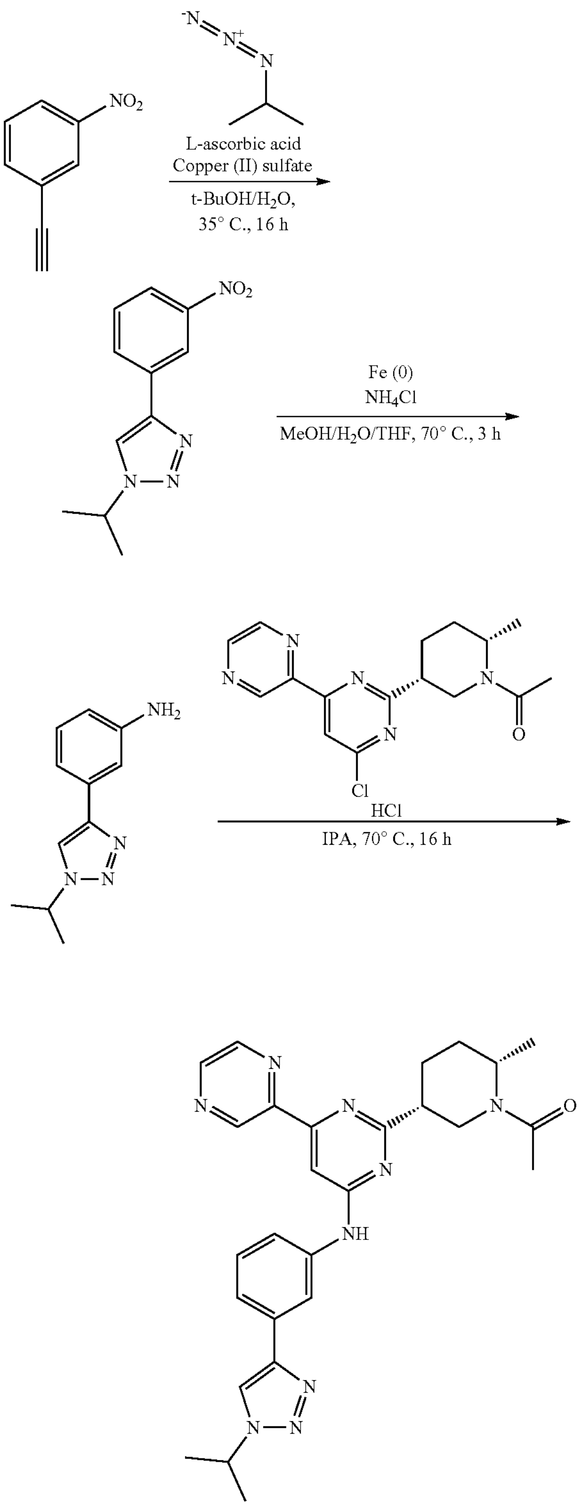

007

To a mixture of 3-nitrophenylacetylene (173 mg, 1.18 mmol), L-ascorbic acid sodium salt (46.6 mg, 0.24 mmol) and anhydrous copper(II) sulfate (37.5 mg, 0.24 mmol) in a mixture of t-butanol (5 mL) and water (5 mL) was added a solution of 2.5M 2-azidopropane in N,N-dimethylformamide (0.47 mL, 1.18 mmol). The reaction mixture was stirred at 35° C. for 16 hours and subsequently diluted with water and ethyl acetate. The mixture was extracted twice with ethyl acetate. The combined organic layers were washed with brine, dried over sodium sulfate, filtered and dried in vacuo. The residue was purified by silica column chromatography (0% to 50% ethyl acetate in n-heptane) to afford 1-isopropyl-4-(3-nitrophenyl)-1H-1,2,3-triazole (147.8 mg, 54%) as a white solid. LCMS (Method C): $t_R$ 1.93 min, 100%, MS (ESI) 233.1 $(M+H)^+$. Iron (106 mg, 1.90 mmol) was added to a stirring solution of ammonium chloride (102 mg, 1.90 mmol) in water (3 mL). A suspension of 1-isopropyl-4-(3-nitrophenyl)-1H-1,2,3-triazole (147 mg, 0.63 mmol) in a mixture of methanol (1.5 mL) and tetrahydrofuran (1.5 mL) was added slowly. The mixture was stirred at 70° C. for 3 hours, allowed to cool to room temperature, diluted with water and ethyl acetate. The organic layer was decanted and the process was repeated three times. The combined organic layers were dried over sodium sulfate, filtered and dried in vacuo to afford 3-(1-isopropyl-1H-1,2,3-triazol-4-yl)aniline (133 mg, 104%) as a yellow gum, which was continued crude without further purification. $^{1}$H-NMR (400 MHz, DMSO-d6) δ 8.47 (s, 1H), 7.11 (t, J=2.0 Hz, 1H), 7.06 (t, J=7.7 Hz, 1H), 6.93 (dt, J=7.6, 1.4 Hz, 1H), 6.54-6.48 (m, 1H), 5.15 (s, 2H), 4.87-4.73 (m, 1H), 1.52 (d, J=6.7 Hz, 6H); LCMS (Method C): $t_R$ 1.61 min, 98%, MS (ESI) 203.1 $(M+H)^+$. To a mixture of 1-((2S,5R)-5-(4-chloro-6-(pyrazin-2-yl)pyrimidin-2-yl)-2-methylpiperidin-1-yl)ethan-1-one (Intermediate 1, 100 mg, 0.25 mmol) and 3-(1-isopropyl-1H-1,2,3-triazol-4-yl)aniline (60.7 mg, 0.30 mmol) in 2-propanol (4 mL) was added concentrated hydrochloric acid (0.02 mL, 0.25 mmol). The mixture was stirred at 70° C. for 16 hours, allowed to cool to room temperature and dried in vacuo. The residue was purified by chiral (preparative) SFC (Method D) and lyophilized to afford 1-((2S,5R)-5-(4-((3-(1-isopropyl-1H-1,2,3-triazol-4-yl)phenyl)amino)-6-(pyrazin-2-yl)pyrimidin-2-yl)-2-methylpiperidin-1-yl)ethan-1-one (007, 77.8 mg, 63%) as a white solid. $^{1}$H-NMR (400 MHz, DMSO-d6, mixture of rotamers) δ 10.01 (d, J=6.2 Hz, 1H), 9.56 (d, J=12.3 Hz, 1H), 8.83-8.77 (m, 2H), 8.62 (d, J=6.1 Hz, 1H), 8.44 (d, J=10.1 Hz, 1H), 7.71-7.61 (m, 2H), 7.54-7.38 (m, 2H), 4.93-4.74 (m, 2H), 4.26-4.17 (m, 0.5H), 4.14-4.02 (m, 0.5H), 3.55-3.46 (m, 0.5H), 3.00-2.85 (m, 1H), 2.81-2.70 (m, 0.5H), 2.18-1.95 (m, 5H), 1.91-1.78 (m, 0.5H), 1.76-1.61 (m, 1.5H), 1.54 (dd, J=6.7, 3.5 Hz, 6H), 1.29-1.23 (m, 1.5H), 1.16-1.05 (m, 1.5H); UPLC (Method A): $t_R$ 1.52 min, 97%, MS (ESI) 498.4 $(M+H)^+$.

The following compounds were prepared following procedures analogous to Example 5, using the appropriate starting materials, and purified using reversed phase chromatography method A/B and/or prep-SFC.

| Compound # | Structure and compound name | Analytical data |
|---|---|---|
| 008 | 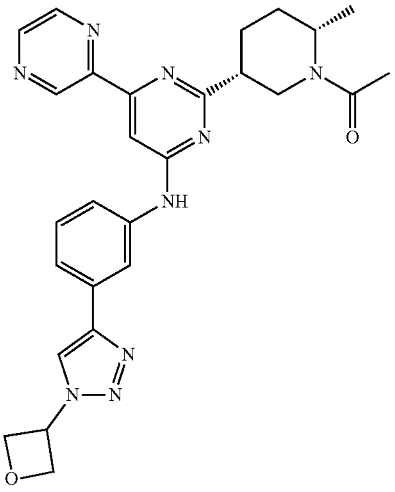 1-((2S,5R)-2-methyl-5-(4-((3-(1-(oxetan-3-yl)-1H-1,2,3-triazol-4-yl)phenyl)amino)-6-(pyrazin-2-yl)pyrimidin-2-yl)piperidin-1-yl)ethan-1-one | $^1$H-NMR (400 MHz, DMSO-d6, mixture of rotamers) δ 10.04 (d, J = 6.8 Hz, 1H), 9.60-9.53 (m, 1H), 8.85 (d, J = 9.8 Hz, 1H), 8.82-8.79 (m, 2H), 8.50 (s, 1H), 7.74-7.62 (m, 2H), 7.57-7.41 (m, 2H), 5.99-5.79 (m, 1H), 5.06 (t, J = 7.3 Hz, 2H), 5.02-4.92 (m, 2H), 4.88-4.74 (m, 1H), 4.29-4.16 (m, 0.5H), 4.11-4.02 (m, 0.5H), 3.56-3.47 (m, 0.5H), 3.01-2.87 (m, 1H), 2.83-2.71 (m, 0.5H), 2.17-1.96 (m, 5H), 1.85 (m, 0.5H), 1.76-1.63 (m, 1.5H), 1.31-1.25 (m, 1.5H), 1.18-1.02 (m, 1.5H); UPLC (Method A): $t_R$ 1.36 min, 99%, MS (ESI) 512.4 $(M + H)^+$. |

Example 6: Synthesis of 1-((2S,5R)-5-(4-((3-fluoro-5-(1H-1,2,3-triazol-4-yl)phenyl)amino)-6-(pyrazin-2-yl)pyrimidin-2-yl)-2-methylpiperidin-1-yl)ethan-1-one (009)

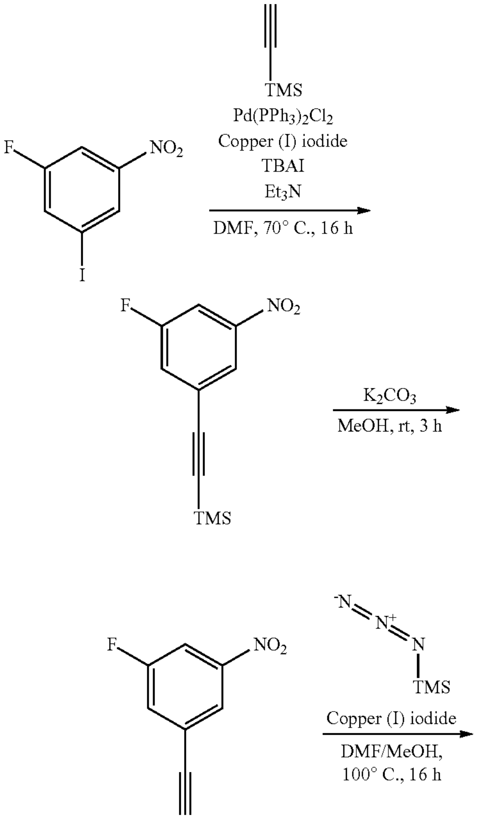

-continued

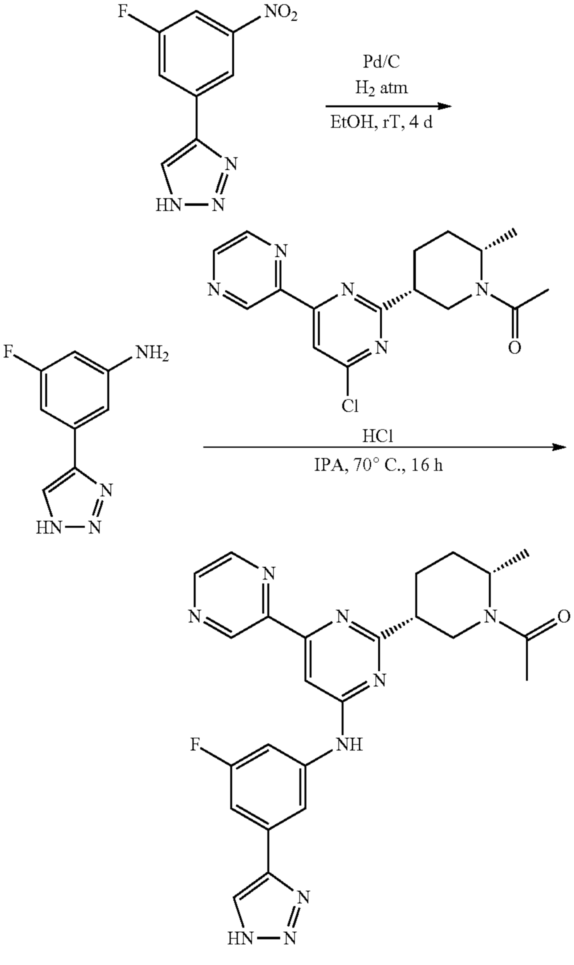

009

Under argon, 1-fluoro-3-iodo-5-nitrobenzene (2 g, 7.49 mmol) was dissolved in N,N-dimethylformamide (30 mL) and bis(triphenylphosphine)palladium(II) dichloride (0.26 g, 0.38 mmol), copper (1) iodide (0.14 g, 0.75 mmol), tetrabutylammonium iodide (0.55 g, 1.50 mmol), triethylamine (1.56 mL, 11.24 mmol) and trimethylsilylacetylene (1.81 mL, 12.73 mmol) were added. The mixture was stirred at 70° C. for 16 hours. The mixture was allowed to cool to room temperature, poured into saturated aqueous ammonium chloride solution and extracted with ethyl acetate three times. The combined organic layers were washed with brine, dried over sodium sulfate and concentrated in vacuo. The residue was coated onto hydromatrix and purified by silica column chromatography (0% to 15% ethyl acetate in n-heptane) twice to afford ((3-fluoro-5-nitrophenyl)ethynyl)trimethylsilane (680 mg, 38%) as a brown gum. $^1$H-NMR (400 MHz, $CDCl_3$) δ 8.14-8.09 (m, 1H), 7.91-7.84 (m, 1H), 7.51-7.44 (m, 1H), 0.28-0.26 (m, 9H). To a solution of ((3-fluoro-5-nitrophenyl)ethynyl)trimethylsilane (880 mg, 3.71 mmol) in methanol (35 mL) was added potassium carbonate (256 mg, 1.85 mmol) and the mixture was stirred at room temperature for 3 hours. The mixture was concentrated in vacuo to give an oil. The oil was diluted with diethyl ether and water. The aqueous layer was extracted with ethyl acetate twice. The combined organic layers were washed with brine, dried over sodium sulfate, and concentrated in vacuo to afford 1-ethynyl-3-fluoro-5-nitrobenzene (514 mg, 84%) as an orange solid. $^1$H-NMR (400 MHz, $CDCl_3$) δ 8.18-8.12 (m, 1H), 7.96-7.89 (m, 1H), 7.55-7.48 (m, 1H), 3.28 (s, 1H). Under argon atmosphere, azidotrimethylsilane (0.49 mL, 3.75 mmol) and copper(I) iodide (23.82 mg, 0.13 mmol) were added to a stirring solution of 1-ethynyl-3-fluoro-5-nitrobenzene (413 mg, 2.50 mmol) in dry N,N-dimethylformamide (20 mL) and methanol (2 mL). The mixture was stirred at 100° C. for 16 hours, allowed to cool to room temperature and poured into saturated aqueous sodium bicarbonate solution. The mixture was extracted with ethyl acetate three times, the combined organic layers were washed with brine, dried over sodium sulfate, filtered and concentrated in vacuo. The residue was purified by silica column chromatography (0% to 50% ethyl acetate in n-heptane) to afford 4-(3-fluoro-5-nitrophenyl)-1H-1,2,3-triazole (460 mg, 88%) as a white solid. $^1$H-NMR (400 MHz, DMSO-d6) δ 15.50 (s, 1H), 8.70 (s, 1H), 8.59-8.53 (m, 1H), 8.26-8.19 (m, 1H), 8.14-8.07 (m, 1H). Under nitrogen atmosphere, to a stirring solution of 4-(3-fluoro-5-nitrophenyl)-1H-1,2,3-triazole (460 mg, 2.21 mmol) in ethanol (30 mL) was added 10% palladium on carbon (50% wet, 47.0 mg, 0.22 mmol). Next, hydrogen atmosphere was introduced and the mixture was stirred at room temperature for 6 days. The mixture was filtered over Celite and the filter cake was rinsed with ethanol. The combined filtrate was concentrated in vacuo and purified by silica column chromatography (0% to 60% ethyl acetate in n-heptane) to afford 3-fluoro-5-(1H-1,2,3-triazol-4-yl)aniline (309 mg, 78%) as a yellow solid. $^1$H-NMR (400 MHz, DMSO-d6) δ 15.11 (s, 1H), 8.22 (s, 1H), 6.95-6.89 (m, 1H), 6.78-6.70 (m, 1H), 6.34-6.26 (m, 1H), 5.55 (s, 2H). LCMS (Method A): $t_R$ 1.11 min, 87%, MS (ESI) 179.0 $(M+H)^+$. To a solution of 1-((2S,5R)-5-(4-chloro-6-(pyrazin-2-yl)pyrimidin-2-yl)-2-methylpiperidin-1-yl)ethan-1-one (Intermediate 1, 100 mg, 0.30 mmol) and 3-fluoro-5-(1H-1,2,3-triazol-4-yl)aniline (64.4 mg, 0.36 mmol) in 2-propanol (4 mL) concentrated hydrochloric acid (0.05 mL, 0.51 mmol) was added and the mixture was heated at 70° C. for 16 hours. The mixture was concentrated in vacuo, purified by preparative reversed phase chromatography (Method A) and lyophilized to afford 1-((2S,5R)-5-(4-((3-fluoro-5-(1H-1,2,3-triazol-4-yl)phenyl)amino)-6-(pyrazin-2-yl)pyrimidin-2-yl)-2-methylpiperidin-1-yl)ethan-1-one (009, 88 mg, 62%) as a white solid. $^1$H-NMR (400 MHz, DMSO-d6, mixture of rotamers) δ 15.18 (s, 1H), 10.25 (d, J=4.8 Hz, 1H), 9.56 (d, J=14.5 Hz, 1H), 8.87-8.78 (m, 2H), 8.38 (s, 1H), 8.10 (d, J=15.1 Hz, 1H), 7.91-7.82 (m, 1H), 7.68 (d, J=2.1 Hz, 1H), 7.39-7.32 (m, 1H), 4.89-4.79 (m, 0.5H), 4.79-4.65 (m, 0.5H), 4.28-4.18 (m, 0.5H), 4.14-4.06 (m, 0.5H), 3.54-3.45 (m, 0.5H), 3.01-2.90 (m, 1H), 2.85-2.74 (m, 0.5H), 2.17-1.95 (m, 5H), 1.94-1.79 (m, 0.5H), 1.77-1.64 (m, 1.5H), 1.32-1.24 (m, 1.5H), 1.19-1.04 (m, 1.5H); UPLC (Method A): $t_R$ 1.29 min, 96%, MS (ESI) 474.2 $(M+H)^+$; Chiral SFC (Method D): $t_R$ 3.45 min, 97%, MS (ESI) 474.1 $(M+H)^+$.

Example 7: Synthesis of 1-((2S,5R)-5-(4-((3-chloro-5-(1H-1,2,3-triazol-4-yl)phenyl)amino)-6-(pyrazin-2-yl)pyrimidin-2-yl)-2-methylpiperidin-1-yl)ethan-1-one (010)

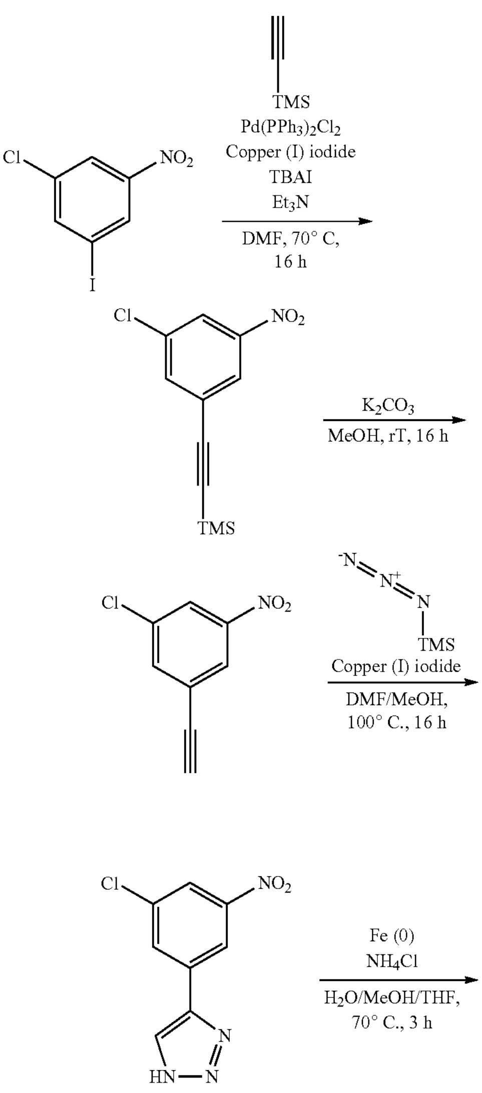

-continued

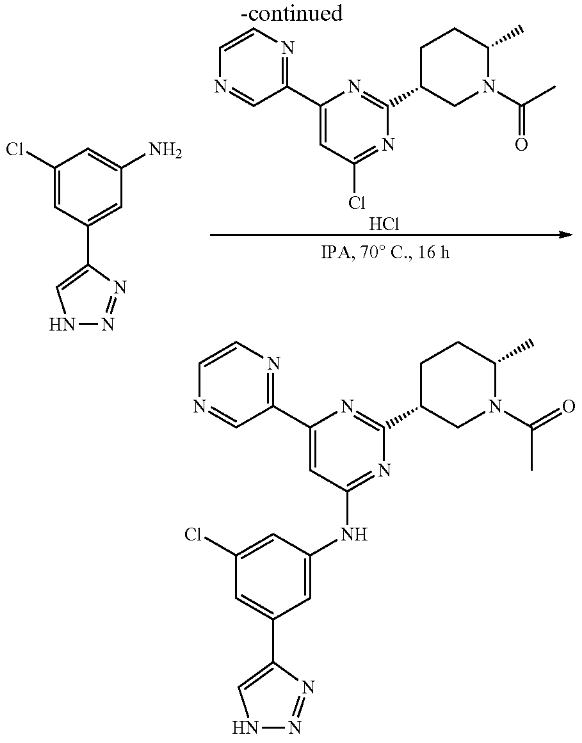

010

Under argon, 1-bromo-3-chloro-5-nitrobenzene (1.24 g, 5.24 mmol) was dissolved in N,N-dimethylformamide (40 mL) and bis(triphenylphosphine)palladium(II) dichloride (0.18 g, 0.26 mmol), copper (1) iodide (0.10 g, 0.52 mmol), tetrabutylammonium iodide (0.39 g, 1.05 mmol), triethylamine (1.09 mL, 7.87 mmol) and trimethylsilylacetylene (1.27 mL, 8.92 mmol) were added. The mixture was stirred at 70° C. for 16 hours. The mixture was allowed to cool to room temperature and concentrated in vacuo. The residue was coated onto hydromatrix and purified by silica column chromatography (0% to 10% ethyl acetate in n-heptane) to afford ((3-chloro-5-nitrophenyl)ethynyl)trimethylsilane (1.0 g, 75%) as a brown gum. $^1$H-NMR (400 MHz, $CDCl_3$) δ 8.22-8.16 (m, 1H), 8.16-8.10 (m, 1H), 7.77-7.72 (m, 1H), 0.30-0.25 (m, 9H); GCMS (Method C): $t_R$ 4.18 min, 94%, MS (EI) 238.1 (M). To a solution of ((3-chloro-5-nitrophenyl)ethynyl)trimethylsilane (1.0 g, 3.94 mmol) in methanol (40 mL) was added potassium carbonate (0.27 g, 1.97 mmol). The mixture was stirred at room temperature for 16 hours and concentrated in vacuo to give an oil. The oil was diluted with diethyl ether and water. The aqueous layer was extracted with ethyl acetate twice. The combined organic layers were washed with brine, dried over sodium sulfate, filtered and concentrated in vacuo to afford 1-chloro-3-ethynyl-5-nitrobenzene (700 mg, 98%) as a beige solid. $^1$H-NMR (400 MHz, $CDCl_3$) δ 8.25-8.17 (m, 2H), 7.80-7.74 (m, 1H), 3.28 (s, 1H). Under argon atmosphere, azidotrimethylsilane (0.76 mL, 5.78 mmol) and copper(I) iodide (47 mg, 0.25 mmol) were added to a stirring solution of 1-chloro-3-ethynyl-5-nitrobenzene (700 mg, 3.86 mmol) in dry N,N-dimethylformamide (30 mL) and methanol (3 mL). The mixture was stirred at 100° C. for 16 hours, allowed to cool to room temperature and poured into saturate aqueous sodium bicarbonate solution. The mixture was extracted with ethyl acetate three times. The combined organic layers were washed with brine, dried over sodium sulfate, filtered and concentrated in vacuo. The residue was coated onto hydromatrix and purified by silica column chromatography (0% to 50% ethyl acetate in n-heptane) to afford 4-(3-chloro-5-nitrophenyl)-1H-1,2,3-triazole (650 mg, 75%) as a white solid. LCMS (Method C): $t_R$ 1.64 min, 95%, MS (ESI) 225.0 $(M+H)^+$. Iron powder (224 mg, 4.01 mmol) was added to a stirring solution of ammonium chloride (214 mg, 4.01 mmol) in water (6 mL). A suspension of 4-(3-chloro-5-nitrophenyl)-1H-1,2,3-triazole (300 mg, 1.34 mmol) in methanol (3 mL) and tetrahydrofuran (3 mL) was added slowly and the mixture was stirred at 70° C. for 3 hours. The mixture was allowed to cool to room temperature, diluted with water and ethyl acetate and stirred for 15 minutes. The organic layer was decanted and the process was repeated three times. The combined organic layers were dried over sodium sulfate, filtered and concentrated in vacuo to afford 3-chloro-5-(1H-1,2,3-triazol-4-yl)aniline (143 mg, 55%) as a yellow gum. $^1$H-NMR (400 MHz, DMSO-d6) δ 15.12 (s, 1H), 8.26 (s, 1H), 7.07-7.01 (m, 1H), 7.01-6.96 (m, 1H), 6.59-6.54 (m, 1H), 5.55 (s, 2H); LCMS (Method C): $t_R$ 1.41 min, 87%, MS (ESI) 195.0 $(M+H)^+$. To a solution of 1-((2S,5R)-5-(4-chloro-6-(pyrazin-2-yl)pyrimidin-2-yl)-2-methylpiperidin-1-yl)ethan-1-one (Intermediate 1, 100 mg, 0.25 mmol) and 3-chloro-5-(1H-1,2,3-triazol-4-yl)aniline (58.4 mg, 0.30 mmol) in 2-propanol (4 mL) was added concentrated hydrochloric acid (0.02 mL, 0.25 mmol). The mixture was stirred at 70° C. for 16 hours, was allowed to cool to room temperature and concentrated in vacuo. The residue was purified by chiral (preparative) SFC (Method D) followed by preparative reversed phase chromatography (Method A) and lyophilized to afford 1-((2S,5R)-5-(4-((3-chloro-5-(1H-1,2,3-triazol-4-yl)phenyl)amino)-6-(pyrazin-2-yl)pyrimidin-2-yl)-2-methylpiperidin-1-yl)ethan-1-one (010, 50 mg, 41%) as a white solid. $^1$H-NMR (400 MHz, DMSO-d6, mixture of rotamers) δ 15.17 (br s, 1H), 10.23 (d, J=4.8 Hz, 1H), 9.56 (d, J=15.0 Hz, 1H), 8.88-8.79 (m, 2H), 8.40 (s, 1H), 8.22 (d, J=8.5 Hz, 1H), 8.15-8.05 (m, 1H), 7.68 (d, J=2.4 Hz, 1H), 7.60-7.53 (m, 1H), 4.90-4.79 (m, 0.5H), 4.76-4.64 (m, 0.5H), 4.27-4.19 (m, 0.5H), 4.12-3.99 (m, 0.5H), 3.54-3.45 (m, 0.5H), 3.04-2.89 (m, 1H), 2.85-2.74 (m, 0.5H), 2.14-2.00 (m, 5H), 1.93-1.79 (m, 0.5H), 1.77-1.62 (m, 1.5H), 1.34-1.27 (m, 1.5H), 1.21-1.12 (m, 1.5H); UPLC (Method A): $t_R$ 1.36 min, 99%, MS (ESI) 490.2 $(M+H)^+$.

Example 8: Synthesis of 1-((2S,5R)-5-(4-((3-(1-ethyl-1H-1,2,3-triazol-4-yl)phenyl)amino)-6-(pyrazin-2-yl)pyrimidin-2-yl)-2-methylpiperidin-1-yl)ethan-1-one (011)

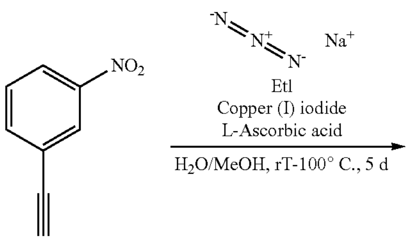

-continued

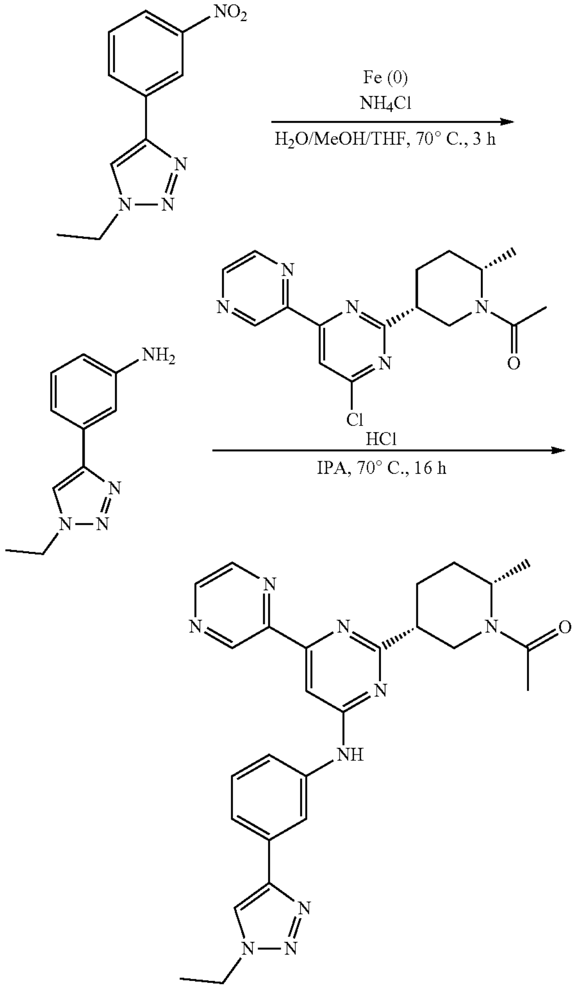

011

To a stirring solution of 3-nitrophenylacetylene (500 mg, 3.40 mmol), sodium azide (265 mg, 4.08 mmol), L-ascorbic acid sodium salt (673 mg, 3.40 mmol) and ethyl iodide (0.33 mL, 4.08 mmol) in methanol (15 mL) and water was added copper(I) iodide (32.4 mg, 0.17 mmol). The mixture was heated to reflux for 3 days followed by stirring at room temperature 2 days. The mixture was concentrated in vacuo, the residue was taken up in water, ethyl acetate and saturated aqueous ammonium chloride. The layers were separated and the aqueous layer was extracted with ethyl acetate twice. The combined organic layers were washed with brine twice, dried over sodium sulfate, filtered and concentrated in vacuo to afford 1-ethyl-4-(3-nitrophenyl)-1H-1,2,3-triazole (427 mg, 58%) as a yellow solid. $^1$H-NMR (400 MHz, DMSO-d6) δ 8.89 (s, 1H), 8.68-8.61 (m, 1H), 8.34-8.25 (m, 1H), 8.24-8.14 (m, 1H), 7.81-7.67 (m, 1H), 4.47 (q, J=7.3 Hz, 2H), 1.51 (t, J=7.3 Hz, 3H); LCMS (Method C): $t_R$ 1.69 min, 90%, MS (ESI) 219.1 $(M+H)^+$. A suspension of 1-ethyl-4-(3-nitrophenyl)-1H-1,2,3-triazole (427 mg, 1.96 mmol) in a mixture of methanol (5 mL) and tetrahydrofuran (5 mL) was added to a stirring mixture of ammonium chloride (314 mg, 5.87 mmol) and iron powder (328 mg, 5.87 mmol) in water (10 mL). The mixture was heated at 70° C. for 3 hours, was allowed to cool to room temperature and the organic solvent was removed in vacuo. The residue was stirred with ethyl acetate for 15 minutes, the organic layer was decanted and the process was repeated twice. The combined organic layers were washed with brine, dried over sodium sulfate, filtered and concentrated in vacuo to afford 3-(1-ethyl-1H-1,2,3-triazol-4-yl)aniline (357 mg, 88%) as a brown gum. $^1$H-NMR (400 MHz, DMSO-d6) δ 8.41 (s, 1H), 7.16-7.00 (m, 2H), 6.92 (d, J=7.6 Hz, 1H), 6.51 (d, J=8.0 Hz, 1H), 5.17 (s, 2H), 4.40 (q, J=7.3 Hz, 2H), 1.47 (t, J=7.3 Hz, 3H); LCMS (Method C): $t_R$ 1.39 min, 88%, MS (ESI) 189.1 $(M+H)^+$. To a solution of 1-((2S,5R)-5-(4-chloro-6-(pyrazin-2-yl)pyrimidin-2-yl)-2-methylpiperidin-1-yl)ethan-1-one (Intermediate 1, 100 mg, 0.25 mmol) and 3-(1-ethyl-1H-1,2,3-triazol-4-yl)aniline (64.2 mg, 0.30 mmol) in 2-propanol (4 mL) was added concentrated hydrochloric acid (0.02 mL, 0.25 mmol). The mixture was stirred at 70° C. for 16 hours, allowed to reach room temperature concentrated in vacuo. The residue was purified by chiral (preparative) SFC (Method D) and lyophilized to afford 1-((2S,5R)-5-(4-((3-(1-ethyl-1H-1,2,3-triazol-4-yl)phenyl)amino)-6-(pyrazin-2-yl)pyrimidin-2-yl)-2-methylpiperidin-1-yl)ethan-1-one (011, 72.2 mg, 60%) as a white solid. $^1$H-NMR (400 MHz, DMSO-d6, mixture of rotamers) δ 10.01 (d, J=5.8 Hz, 1H), 9.56 (dd, J=11.5, 1.0 Hz, 1H), 8.84-8.77 (m, 2H), 8.57 (d, J=6.5 Hz, 1H), 8.46 (s, 1H), 7.71-7.60 (m, 2H), 7.54-7.39 (m, 2H), 4.87-4.76 (m, 1H), 4.44 (p, J=7.3 Hz, 2H), 4.28-4.15 (m, 0.5H), 4.13-4.03 (m, 0.5H), 3.57-3.45 (m, 0.5H), 3.00-2.85 (m, 1H), 2.82-2.72 (m, 0.5H), 2.16-1.98 (m, 5H), 1.91-1.80 (m, 0.5H), 1.77-1.59 (m, 1.5H), 1.49 (td, J=7.3, 1.5 Hz, 3H), 1.31-1.22 (m, 1.5H), 1.17-1.09 (m, 1.5H); UPLC (Method A): $t_R$ 1.45 min, 99%, MS (ESI) 484.4 $(M+H)^+$; Chiral SFC (Method D): $t_R$ 3.00 min, 99%, MS (ESI) 484.2 $(M+H)^+$.

Example 9: Synthesis of 1-((2S,5R)-2-methyl-5-(4-((4-methyl-3-(1-methyl-1H-1,2,3-triazol-4-yl)phenyl)amino)-6-(pyrazin-2-yl)pyrimidin-2-yl)piperidin-1-yl)ethan-1-one (012)

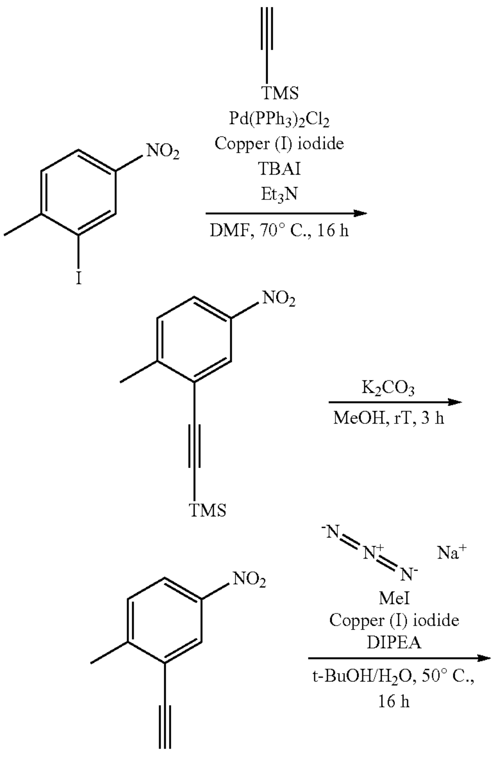

-continued

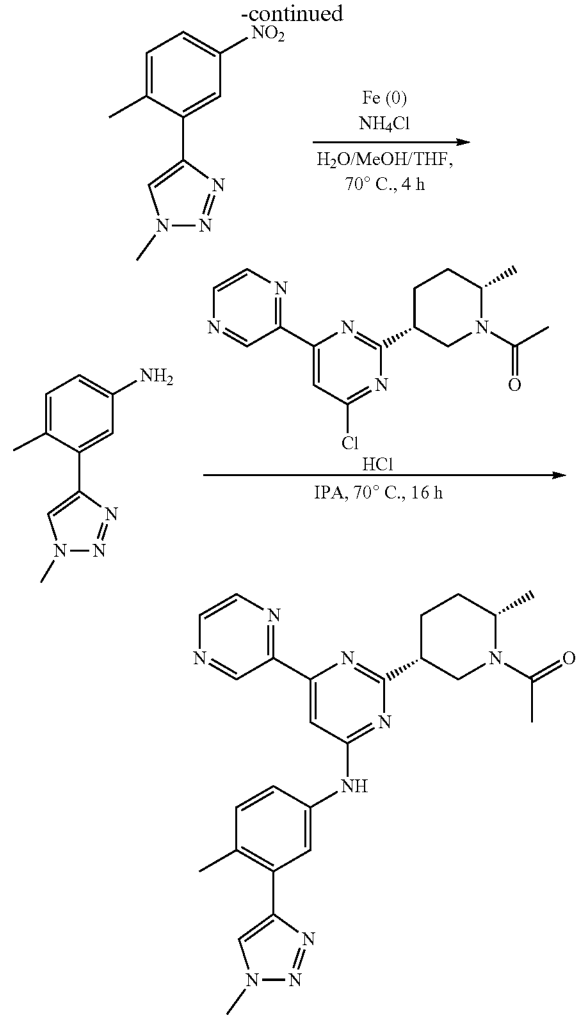

012

Under argon, 2-iodo-1-methyl-4-nitrobenzene (1.17 g, 4.43 mmol) was dissolved in dry N,N-dimethylformamide (15 mL) and bis(triphenylphosphine)palladium(II) dichloride (0.16 g, 0.22 mmol), copper(I) iodide (0.08 g, 0.44 mmol), tetrabutylammonium iodide (0.33 g, 0.89 mmol), triethylamine (0.92 mL, 6.64 mmol), and trimethylsilylacetylene (1.07 mL, 7.53 mmol) were added. The mixture was stirred at 70° C. for 16 hours. The mixture was allowed to cool to room temperature, poured into saturated ammonium chloride and extracted with ethyl acetate three times. The combined organic layers were washed with brine, dried over sodium sulfate and concentrated in vacuo. The dark oil was coated onto hydromatrix and purified by silica column chromatography (0% to 10% ethyl acetate in n-heptane) to afford trimethyl((2-methyl-5-nitrophenyl)ethynyl)silane (596 mg, 95%) as a dark yellow oil. $^1$H-NMR (400 MHz, $CDCl_3$) δ 8.28 (d, J=2.4 Hz, 1H), 8.05 (dd, J=8.5, 2.4 Hz, 1H), 7.35 (d, J=8.4 Hz, 1H), 2.53 (s, 3H), 0.34-0.27 (m, 9H). To a solution of trimethyl((2-methyl-5-nitrophenyl)ethynyl) silane (596 mg, 2.55 mmol) in methanol (25 mL) was added potassium carbonate (177 mg, 1.28 mmol) and the mixture was stirred at room temperate for 3 hours. The mixture was concentrated in vacuo to give an oil. The oil was diluted with ethyl acetate and water. The aqueous layer was extracted with ethyl acetate twice. The combined organic layers were washed with brine, dried over sodium sulfate, filtered and concentrated in vacuo. The residue was coated onto hydromatrix and purified by silica column chromatography (0% to 10% ethyl acetate in n-heptane) to afford 2-ethynyl-1-methyl-4-nitrobenzene (156 mg, 38%) as a yellow oil. $^1$H-NMR (400 MHz, $CDCl_3$) δ 8.31 (d, J=2.5 Hz, 1H), 8.09 (dd, J=8.5, 2.5 Hz, 1H), 7.38 (d, J=8.5 Hz, 1H), 3.41 (s, 1H), 2.55 (s, 3H). To solution of 2-ethynyl-1-methyl-4-nitrobenzene (156 mg, 0.97 mmol) in water (2 mL) and t-butanol (2 mL) were added iodomethane (0.05 mL, 0.78 mmol), sodium azide (50.7 mg, 0.78 mmol), N,N-diisopropylethylamine (0.14 mL, 0.78 mmol) and copper(I) iodide (13.53 mg, 0.07 mmol). The mixture was stirred at 50° C. for 16 hours. The mixture was diluted with water and ethyl acetate and saturated aqueous sodium bicarbonate was added. The layers were separated and the aqueous phase was extracted with ethyl acetate twice. The combined organic layers were washed with brine, dried over sodium sulfate, filtered and concentrated in vacuo. The residue was purified by silica column chromatography (0% to 75% ethyl acetate in n-heptane) to afford a 1-methyl-4-(2-methyl-5-nitrophenyl)-1H-1,2,3-triazole (75.6 mg, 36%) as a white solid. $^1$H-NMR (400 MHz, $CDCl_3$) δ 8.59 (d, J=2.5 Hz, 1H), 8.11 (dd, J=8.4, 2.5 Hz, 1H), 7.76 (s, 1H), 7.44 (d, J=8.5 Hz, 1H), 4.22 (s, 3H), 2.61 (s, 3H). To a solution of 1-methyl-4-(2-methyl-5-nitrophenyl)-1H-1,2,3-triazole (75 mg, 0.34 mmol) in methanol (1.5 mL) and tetrahydrofuran (1.5 mL) was added water (3 mL), ammonium chloride (55.2 mg, 1.03 mmol) and iron (57.6 mg, 1.03 mmol). The mixture was heated at 70° C. for 4 hours and a subsequently concentrated in vacuo. The aqueous residue was stirred with ethyl acetate for 15 minutes, the organic layer was decanted and the process was repeated twice. The combined organic layers were dried over sodium sulfate, filtered and concentrated in vacuo to afford 4-methyl-3-(1-methyl-1H-1,2,3-triazol-4-yl)aniline (56.9 mg, 88%) as a brown gum. $^1$H-NMR (400 MHz, DMSO-d6) δ 8.20 (s, 1H), 7.02 (d, J=2.4 Hz, 1H), 6.92 (d, J=8.1 Hz, 1H), 6.48 (dd, J=8.1, 2.5 Hz, 1H), 4.94 (s, 2H), 4.08 (s, 3H), 2.23 (s, 3H). To a solution of 1-((2S,5R)-5-(4-chloro-6-(pyrazin-2-yl)pyrimidin-2-yl)-2-methylpiperidin-1-yl)ethan-1-one (Intermediate 1, 80 mg, 0.24 mmol) and 4-methyl-3-(1-methyl-1H-1,2,3-triazol-4-yl)aniline (54.5 mg, 0.29 mmol) in 2-propanol (5 mL) was added concentrated hydrochloric acid and the mixture was stirred at 70° C. for 16 hours. The mixture was concentrated in vacuo, purified by preparative reversed phase chromatography (Method A) and lyophilized to afford 1-((2S,5R)-2-methyl-5-(4-((4-methyl-3-(1-methyl-1H-1,2,3-triazol-4-yl)phenyl) amino)-6-(pyrazin-2-yl)pyrimidin-2-yl)piperidin-1-yl) ethan-1-one (012, 49.1 mg, 42%) as a white solid. $^1$H-NMR (400 MHz, DMSO-d6, mixture of rotamers) δ 9.93 (d, J=6.9 Hz, 1H), 9.54 (dd, J=12.3, 1.1 Hz, 1H), 8.82-8.76 (m, 2H), 8.37-8.22 (m, 2H), 7.68-7.58 (m, 2H), 7.29 (d, J=8.2 Hz, 1H), 4.87-4.76 (m, 0.5H), 4.77-4.66 (m, 0.5H), 4.26-4.15 (m, 0.5H), 4.14-4.08 (m, 3H), 4.06-3.98 (m, 0.5H), 3.52-3.40 (m, 0.5H), 2.95-2.81 (m, 1H), 2.80-2.68 (m, 0.5H), 2.43-2.36 (m, 3H), 2.13-1.91 (m, 5H), 1.89-1.77 (m, 0.5H), 1.75-1.59 (m, 1.5H), 1.26-1.20 (m, 1.5H), 1.15-1.01 (m, 1.5H); UPLC (Method A): $t_R$ 1.42 min, 99%, MS (ESI) 484.4 $(M+H)^+$.

The following compounds were prepared following procedures analogous to Example 9, using the appropriate starting materials, and purified using reversed phase chromatography method A/B and/or prep-SFC.

| Compound # | Structure and compound name | Analytical data |
|---|---|---|
| 013 | 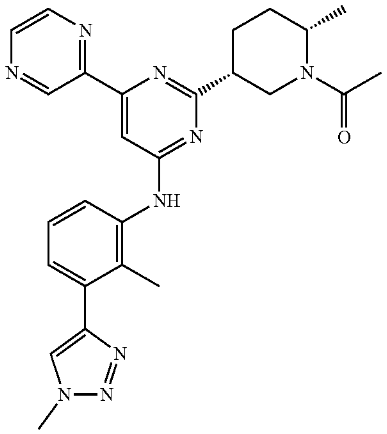 1-((2S,5R)-2-methyl-5-(4-((2-methyl-3-(1-methyl-1H-1,2,3-triazol-4-yl)phenyl)amino)-6-(pyrazin-2-yl)pyrimidin-2-yl)piperidin-1-yl)-ethan-1-one | $^{1}$H-NMR (400 MHz, DMSO-d6, mixture of rotamers) δ 9.54 (dd, J = 11.9, 1.4 Hz, 1H), 9.42 (s, 1H), 8.80-8.70 (m, 2H), 8.37 (d, J = 6.6 Hz, 1H), 7.59-7.43 (m, 2H), 7.34 (t, J = 7.8 Hz, 2H), 4.86-4.74 (m, 0.5H), 4.77-4.66 (m, 0.5H), 4.24-4.15 (m, 0.5H), 4.12 (s, 3H), 4.08-3.98 (m, 0.5H), 3.49-3.40 (m, 0.5H), 2.91-2.74 (m, 1H), 2.70-2.58 (m, 0.5H), 2.35-2.26 (m, 3H), 2.08-1.88 (m, 5H), 1.87-1.73 (m, 0.5H), 1.72-1.59 (m, 1.5H), 1.26-1.20 (m, 1.5H), 1.15-1.01 (m, 1.5H); UPLC (Method A): $t_R$ 1.34 min, 98%, MS (ESI) 484.4 (M + H)$^+$. |

Example 10: Synthesis of 1-((2S,5R)-2-methyl-5-(4-((3-methyl-5-(1-methyl-1H-1,2,3-triazol-4-yl)phenyl)amino)-6-(pyrazin-2-yl)pyrimidin-2-yl)piperidin-1-yl)ethan-1-one (014)

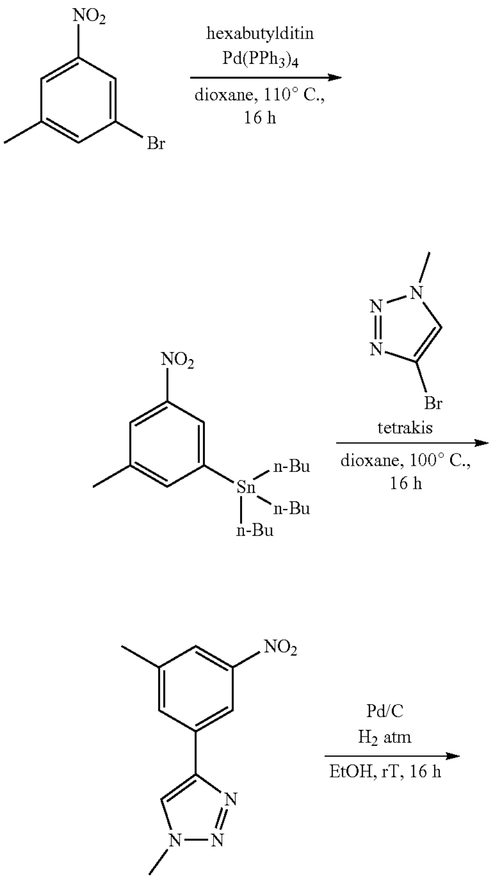

-continued

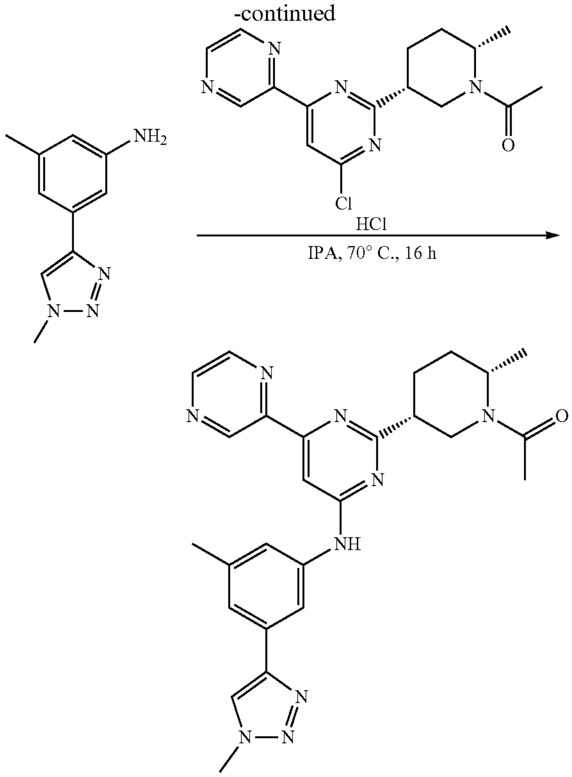

014

Under argon atmosphere, to a solution of 3-bromo-5-nitrotoluene (1 g, 4.63 mmol) in dry 1,4-dioxane (20 mL) were added hexa-n-butylditin (11.57 mL, 23.14 mmol) and tetrakis(triphenylphosphine)palladium(0) (1.07 g, 0.93 mmol). The mixture was stirred at 110° C. for 16 hours. The mixture was allowed to cool to room temperature, filtered through silica, and concentrated in vacuo to give a dark oil. The dark oil was coated onto hydromatrix and purified by silica column chromatography (0% to 50% ethyl acetate in n-heptane) to afford tributyl(3-methyl-5-nitrophenyl)stannane (1.3 g, 66%) as a yellow oil. $^1$H-NMR (400 MHz, $CDCl_3$) δ 8.15-8.02 (m, 1H), 7.95-7.90 (m, 1H), 7.61-7.48 (m, 1H), 2.48-2.40 (m, 3H), 1.78-1.43 (m, 6H), 1.43-1.21 (m, 6H), 1.21-0.99 (m, 6H), 0.99-0.80 (m, 9H). Under argon atmosphere, tributyl(3-methyl-5-nitrophenyl)stannane (1.3 g, 3.05 mmol) and 4-bromo-1-methyl-1,2,3-triazole (0.49 g, 3.05 mmol) were dissolved in dry 1,4-dioxane (15 mL). Next, tetrakis(triphenylphosphine)palladium(0) (0.71 g, 0.61 mmol) was added and the mixture was heated at 100° C. for 16 hours. The mixture was allowed to cool to room temperature, diluted with ethyl acetate and washed with a saturated aqueous potassium fluoride solution. The aqueous layer was extracted with ethyl acetate twice. The combined organic layers were washed with brine twice, dried over sodium sulfate, filtered and coated onto silica. The coated product was purified by silica column chromatography (0% to 50% ethyl acetate in n-heptane) to afford 1-methyl-4-(3-methyl-5-nitrophenyl)-1H-1,2,3-triazole (590 mg, 40%) as an off-white solid. LCMS (Method C): $t_R$ 1.84 min, 62%, MS (ESI) 219.1 $(M+H)^+$. Under argon atmosphere, 1-methyl-4-(3-methyl-5-nitrophenyl)-1H-1,2,3-triazole (590 mg, 1.07 mmol) was dissolved in ethanol (20 mL) and 10% palladium on carbon (50% wet, 227 mg, 0.11 mmol) was added. Hydrogen atmosphere was introduced and the mixture was stirred at room temperature for 16 hours. The mixture was filtered over Celite, the filter cake was rinsed with ethanol and the combined filtrate was concentrated in vacuo. The crude was purified twice by silica column chromatography (0% to 5% methanol in dichloromethane) to afford 3-methyl-5-(1-methyl-1H-1,2,3-triazol-4-yl)aniline (122 mg, 61%) as a sticky yellowish oil. LCMS (Method C): $t_R$ 1.40 min, 94%, MS (ESI) 198.1 $(M+H)^+$. To a solution of 1-((2S,5R)-5-(4-chloro-6-(pyrazin-2-yl)pyrimidin-2-yl)-2-methylpiperidin-1-yl)ethan-1-one (Intermediate 1, 100 mg, 0.30 mmol) and 3-methyl-5-(1-methyl-1H-1,2,3-triazol-4-yl)aniline (68.1 mg, 0.36 mmol) in 2-propanol (4 mL) was added concentrated hydrochloric acid (0.05 mL, 0.51 mmol). The mixture was stirred at 70° C. for 16 hours, allowed to cool to room temperature and concentrated in vacuo. The crude was purified by preparative reversed phase chromatography (Method A) followed by chiral (preparative) SFC (Method D) and lyophilized to afford 1-((2S,5R)-2-methyl-5-(4-((3-methyl-5-(1-methyl-1H-1,2,3-triazol-4-yl)phenyl)amino)-6-(pyrazin-2-yl)pyrimidin-2-yl)piperidin-1-yl)ethan-1-one (014, 46.8 mg, 32%) as a white solid. $^1$H-NMR (400 MHz, DMSO-d6, mixture of rotamers) δ 9.95 (d, J=5.3 Hz, 1H), 9.59-9.50 (m, 1H), 8.87-8.77 (m, 2H), 8.47 (d, J=15.0 Hz, 1H), 8.18 (s, 1H), 7.65 (s, 1H), 7.60 (d, J=15.0 Hz, 1H), 7.33 (d, J=20.8 Hz, 1H), 4.87-4.77 (m, 1H), 4.28-4.15 (m, 0.5H), 4.13-4.02 (m, 3.5H), 3.55-3.46 (m, 0.5H), 2.99-2.86 (m, 1H), 2.84-2.71 (m, 0.5H), 2.41-2.34 (m, 3H), 2.15-1.96 (m, 5H), 1.93-1.78 (m, 0.5H), 1.77-1.56 (m, 1.5H), 1.34-1.26 (m, 1.5H), 1.19-1.07 (m, 1.5H); UPLC (Method A): $t_R$ 1.44 min, 100%, MS (ESI) 484.4 $(M+H)^+$.

Example 11: Synthesis of 1-((2S,5R)-5-(4-((3-(1,5-dimethyl-1H-1,2,3-triazol-4-yl)phenyl)amino)-6-(pyrazin-2-yl)pyrimidin-2-yl)-2-methylpiperidin-1-yl)ethan-1-one (015) and 1-((2S,5R)-5-(4-((3-(2,5-dimethyl-2H-1,2,3-triazol-4-yl)phenyl)amino)-6-(pyrazin-2-yl)pyrimidin-2-yl)-2-methylpiperidin-1-yl)ethan-1-one (016)

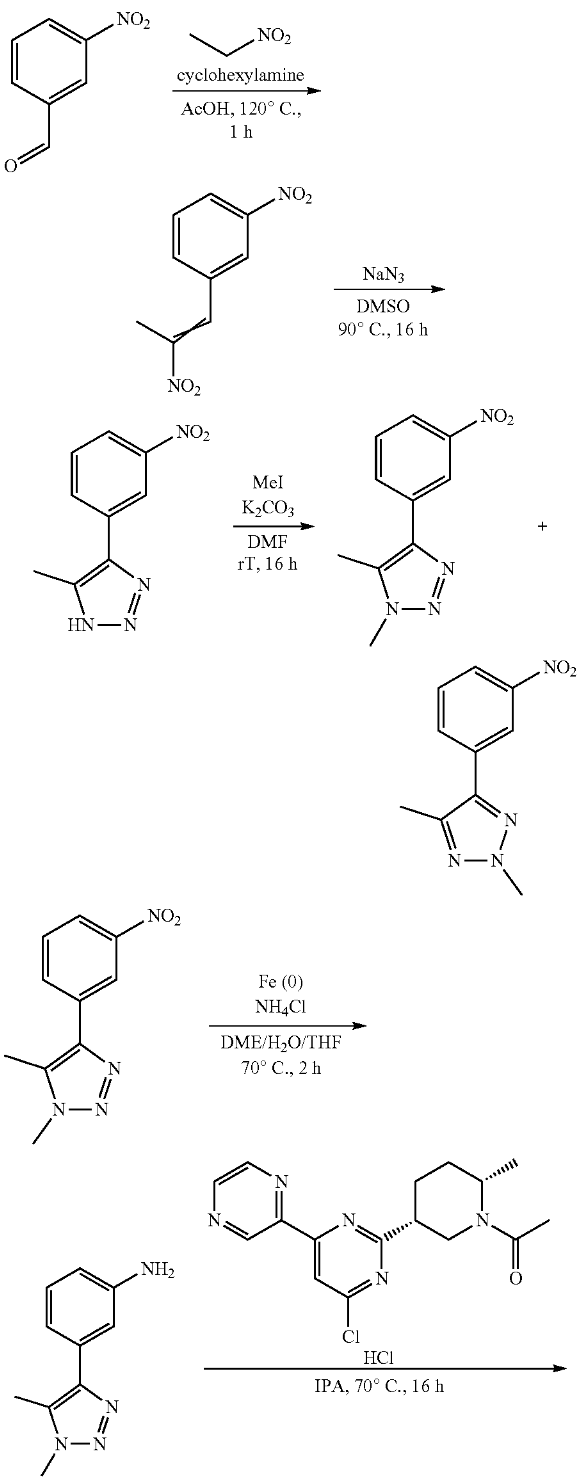

-continued

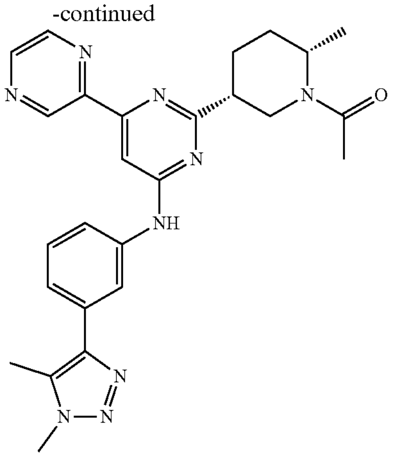

015

A microwave vial was charged with 3-nitrobenzaldehyde (2.5 g, 16.54 mmol), cyclohexylamine (2.08 mL, 18.20 mmol) and nitroethane (2.39 mL, 33.1 mmol) in acetic acid (25 mL) and the mixture was heated in a microwave to 120° C. for 1 hour. The mixture was diluted with water and extracted with dichloromethane three times. The combined organic layers were washed with saturated aqueous sodium bicarbonate solution three times, dried over sodium sulfate, filtered and concentrated in vacuo. The crude material was purified by silica column chromatography (0% to 50% dichloromethane in n-heptane) to afford 1-nitro-3-(2-nitroprop-1-en-1-yl)benzene (2.88 g, 80%) as a bright yellow solid. $^1$H-NMR (400 MHz, $CDCl_3$, E/Z-mixture) δ 8.33-8.26 (m, 2H), 8.10 (s, 1H), 7.77-7.71 (m, 1H), 7.71-7.64 (m, 1H), 2.51-2.46 (m, 3H); LCMS (Method A): $t_R$ 1.96 min, 95%, MS (ESI) 209.2 $(M+H)^+$. A solution of 1-nitro-3-(2-nitroprop-1-en-1-yl)benzene (2.88 g, 13.17 mmol) and sodium azide (1.3 g, 20.00 mmol) in dimethyl sulfoxide (30 mL) was heated to 90° C. for 16 hours. The mixture was allowed to cool to room temperature and poured into water (150 mL). A fine white solid crashed out and was triturated at room temperature for 2 hours. The solids were collected by filtration, washed with water and dried for 16 hours in a vacuum oven at 40° C. to afford 5-methyl-4-(3-nitrophenyl)-1H-1,2,3-triazole (2.12 g, 79%) as a white solid. $^1$H-NMR (400 MHz, DMSO-d6) δ 15.07 (s, 1H), 8.54-8.48 (m, 1H), 8.22 (dd, J=7.8, 2.2 Hz, 1H), 7.78 (t, J=8.0 Hz, 1H), 2.52 (s, 3H); LCMS (Method A): $t_R$ 1.71 min, 96%, MS (ESI) 205.1 $(M+H)^+$. To a solution of 5-methyl-4-(3-nitrophenyl)-1H-1,2,3-triazole (500 mg, 2.45 mmol) in dry N,N-dimethylformamide (20 mL) were added potassium carbonate (440 mg, 3.18 mmol) and iodomethane (0.20 mL, 3.18 mmol). The mixture was stirred at room temperature for 16 hours, concentrated in vacuo, diluted with dichloromethane, stirred at room temperature for 10 minutes and filtered over sand. The filtrate was purified by column chromatography (0% to 50% ethyl acetate in n-heptane) to afford 1,5-dimethyl-4-(3-nitrophenyl)-1H-1,2,3-triazole (173 mg, 32%) and 2,4-dimethyl-5-(3-nitrophenyl)-2H-1,2,3-triazole (299 mg, 56%) as white solids. 1,5-dimethyl-4-(3-nitrophenyl)-1H-1,2,3-triazole: LCMS (Method C): $t_R$ 1.77 min, 98%, MS (ESI) 219.0 $(M+H)^+$. 2,4-dimethyl-5-(3-nitrophenyl)-2H-1,2,3-triazole: LCMS (Method C): $t_R$ 1.97 min, 100%, MS (ESI): 219.0 $(M+H)^+$. To a mixture of ammonium chloride (167 mg, 3.12 mmol) and iron powder in water (8 mL) was added a solution of 1,5-dimethyl-4-(3-nitrophenyl)-1H-1,2,3-triazole (170 mg, 0.78 mmol) in methanol (4 mL) and tetrahydrofuran (4 mL). The suspension was stirred at 70° C. for 2 hours and the organic solvent was removed in vacuo. The aqueous solution was stirred with ethyl acetate for 10 minutes, the organic layer was decanted and the process was repeated twice. The combined organic layers were dried over sodium sulfate, filtered and concentrated in vacuo to afford 3-(1,5-dimethyl-1H-1,2,3-triazol-4-yl)aniline (153 mg, 104%) as a brown gum, which was continued crude without further purification. $^1$H-NMR (400 MHz, DMSO-d6) δ 7.08 (t, J=7.8 Hz, 1H), 6.95-6.90 (m, 1H), 6.78 (d, J=7.5 Hz, 1H), 6.55-6.50 (m, 1H), 5.17 (s, 2H), 3.95 (s, 3H), 2.41 (s, 3H); LCMS (Method C): $t_R$ 1.36 min, 97%, MS (ESI) 189.1 $(M+H)^+$. To a solution of 1-((2S,5R)-5-(4-chloro-6-(pyrazin-2-yl)pyrimidin-2-yl)-2-methylpiperidin-1-yl)ethan-1-one (Intermediate 1, 100 mg, 0.30 mmol) and 3-(1,5-dimethyl-1H-1,2,3-triazol-4-yl)aniline (68.1 mg, 0.36 mmol) in 2-propanol (4 mL) was added concentrated hydrochloric acid (0.05 mL, 0.51 mmol) and stirred at 70° C. for 16 hours. The mixture was allowed to cool to room temperature, concentrated in vacuo and purified by preparative reversed phase chromatography (Method A) followed by chiral (preparative) SFC (Method D) and lyophilized to afford 1-((2S,5R)-5-(4-((3-(1,5-dimethyl-1H-1,2,3-triazol-4-yl)phenyl)amino)-6-(pyrazin-2-yl)pyrimidin-2-yl)-2-methylpiperidin-1-yl)ethan-1-one (015, 58.5 mg, 40%) as a white solid. $^1$H-NMR (400 MHz, DMSO-d6, mixture of rotamers) δ 10.03 (d, J=5.1 Hz, 1H), 9.56 (dd, J=13.4, 1.2 Hz, 1H), 8.83-8.77 (m, 2H), 8.26 (s, 0.5H), 8.20 (s, 0.5H), 7.78-7.68 (m, 1H), 7.67 (d, J=2.1 Hz, 1H), 7.49-7.41 (m, 1H), 7.38-7.32 (m, 1H), 4.88-4.77 (m, 0.5H), 4.73-4.66 (m, 0.5H), 4.27-4.15 (m, 0.5H), 4.08-4.01 (m, 0.5H), 3.99 (s, 3H), 3.53-3.48 (m, 0.5H), 2.99-2.84 (m, 1H), 2.78-2.69 (m, 0.5H), 2.50 (s, 3H), 2.15-1.91 (m, 5H), 1.90-1.76 (m, 0.5H), 1.75-1.63 (m, 1.5H), 1.29-1.21 (m, 1.5H), 1.16-1.05 (m, 1.5H); UPLC (Method A): $t_R$ 1.39 min, 100%, MS (ESI) 484.4 $(M+H)^+$.

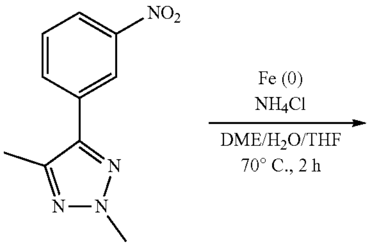

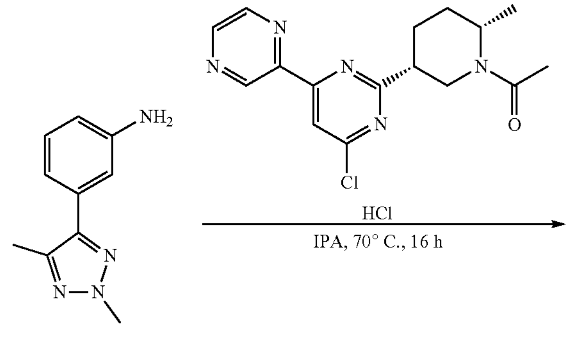

-continued

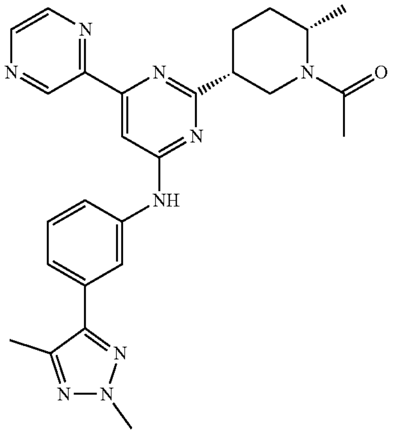

016

2,4-Dimethyl-5-(3-nitrophenyl)-2H-1,2,3-triazole was converted into 1-((2S,5R)-5-(4-((3-(2,5-dimethyl-2H-1,2,3-triazol-4-yl)phenyl)amino)-6-(pyrazin-2-yl)pyrimidin-2-yl)-2-methylpiperidin-1-yl)ethan-1-one (016) following procedures analogous to 015. $^1$H-NMR (400 MHz, DMSO-d6, mixture of rotamers) δ 10.03 (d, J=7.2 Hz, 1H), 9.56 (dd, J=13.7, 1.1 Hz, 1H), 8.83-8.77 (m, 2H), 8.33 (s, 0.5H), 8.27 (s, 0.5H), 7.75-7.64 (m, 2H), 7.45 (td, J=7.9, 2.1 Hz, 1H), 7.35 (d, J=7.8 Hz, 1H), 4.88-4.77 (m, 0.5H), 4.76-4.68 (m, 0.5H), 4.26-4.16 (m, 0.5H), 4.09-3.99 (m, 3.5H), 3.55-3.47 (m, 0.5H), 3.01-2.86 (m, 1H), 2.81-2.69 (m, 0.5H), 2.45 (s, 3H), 2.17-1.93 (m, 5H), 1.91-1.76 (m, 0.5H), 1.75-1.63 (m, 1.5H), 1.27-1.19 (m, 1.5H), 1.15-1.08 (m, 1.5H); UPLC (Method A): $t_R$ 1.57 min, 100%, MS (ESI) 484.4 $(M+H)^+$.

Example 12: Synthesis of 1-((2S,5R)-2-methyl-5-(4-((3-(1-methyl-1H-1,2,3-triazol-5-yl)phenyl)amino)-6-(pyrazin-2-yl)pyrimidin-2-yl)piperidin-1-yl)ethan-1-one (017)

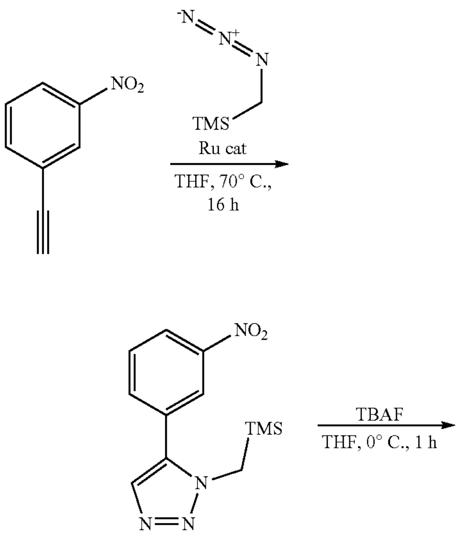

-continued

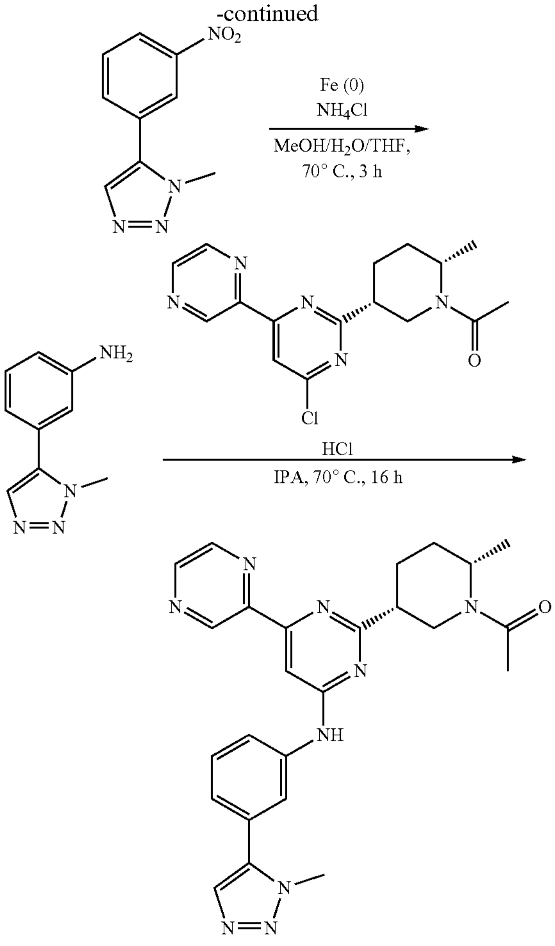

017

A mixture of 3-nitrophenylacetylene (500 mg, 3.40 mmol), trimethylsilyl methyl azide (0.56 mL, 3.74 mmol) and chloro(pentamethylcyclopentadienyl)bis(triphenylphosphine)ruthenium(II) (276 mg, 0.34 mmol) in tetrahydrofuran (20 mL) was stirred at 70° C. for 16 hours. The mixture was concentrated in vacuo and purified by silica column chromatography (20% to 50% ethyl acetate in n-heptane) to afford 5-(3-nitrophenyl)-1-((trimethylsilyl)methyl)-1H-1,2,3-triazole (614 mg, 65%) as a brown oil. LCMS (Method C): $t_R$ 2.07 min, 100%, MS (ESI) 277.1 $(M+H)^+$. A solution of 5-(3-nitrophenyl)-1-((trimethylsilyl)methyl)-1H-1,2,3-triazole (710 mg, 2.57 mmol) in tetrahydrofuran (25 mL) was cooled to 0° C. using an ice bath and 1M tetra-n-butylammonium fluoride in tetrahydrofuran (2.57 mL, 2.57 mmol) was added slowly. The mixture was stirred at 0° C. for 1 hour, quenched with water and extracted with ethyl acetate three times. The combined organic layers were washed with brine, dried over sodium sulfate, filtered and concentrated in vacuo. The residue was purified by silica column chromatography (0% to 50% ethyl acetate in n-heptane) to afford 1-methyl-5-(3-nitrophenyl)-1H-1,2,3-triazole (289 mg, 55%) as a white solid. LCMS (Method C): $t_R$ 1.68 min, 99%, MS (ESI) 205.1 $(M+H)^+$. To a mixture of iron powder (237 mg, 4.25 mmol) and ammonium chloride (227 mg, 4.25 mmol) in water (30 mL) was slowly added a suspension of 1-methyl-5-(3-nitrophenyl)-1H-1,2,3-triazole (289 mg, 1.42 mmol) in methanol (10 mL). The mixture was stirred at 70° C. for 3 hours, the mixture was allowed to cool to room temperature and the organic solvent was removed in vacuo. The red slurry was diluted with water and ethyl acetate and stirred for 15 minutes. The organic layer was decanted and the process was repeated twice. The combined organic layers were washed with brine, dried over sodium sulfate, filtered and concentrated in vacuo. The residue was co-evaporated with dichloromethane to afford 3-(1-methyl-1H-1,2,3-triazol-5-yl)aniline (232 mg, 94%) as a brown solid. LCMS (Method C): $t_R$ 1.29 min, 95%, MS (ESI) 175.1 $(M+H)^+$. To a solution of 1-((2S,5R)-5-(4-chloro-6-(pyrazin-2-yl)pyrimidin-2-yl)-2-methylpiperidin-1-yl) ethan-1-one (Intermediate 1, 100 mg, 0.30 mmol) and 3-(1-methyl-1H-1,2,3-triazol-5-yl)aniline (70.9 mg, 0.41 mmol) in 2-propanol (4 mL) was added concentrated hydrochloric acid (0.05 mL, 0.51 mmol) and the mixture was stirred at 70° C. for 3 days. The mixture was concentrated in vacuo, purified by preparative reversed phase chromatography (Method A) followed by chiral (preparative) SFC (Method D) and lyophilized to afford 1-((2S,5R)-2-methyl-5-(4-((3-(1-methyl-1H-1,2,3-triazol-5-yl)phenyl)amino)-6-(pyrazin-2-yl)pyrimidin-2-yl)piperidin-1-yl)ethan-1-one (017, 48.6 mg, 34%) as a white solid. $^1H$-NMR (400 MHz, DMSO-d6, mixtures of rotamers) δ 10.13 (d, J=7.7 Hz, 1H), 9.56 (dd, J=13.2, 1.2 Hz, 1H), 8.84-8.77 (m, 2H), 8.16 (s, 1H), 7.92 (d, J=2.2 Hz, 1H), 7.78-7.72 (m, 1H), 7.68 (d, J=2.3 Hz, 1H), 7.54 (td, J=7.9, 2.5 Hz, 1H), 7.29 (d, J=7.6 Hz, 1H), 4.87-4.75 (m, 0.5H), 4.75-4.67 (m, 0.5H), 4.24-4.16 (m, 0.5H), 4.11 (s, 3H), 4.07-3.95 (m, 0.5H), 3.48-3.39 (m, 0.5H), 2.95-2.84 (m, 1H), 2.79-2.70 (m, 0.5H), 2.11-1.92 (m, 5H), 1.91-1.75 (m, 0.5H), 1.71-1.59 (m, 1.5H), 1.28-1.17 (m, 1.5H), 1.13-1.04 (m, 1.5H); UPLC (Method A): $t_R$ 1.36 min, 100%, MS (ESI) 470.2 $(M+H)^+$.

Example 13: Synthesis of 1-((2S,5R)-5-(4-((4-fluoro-3-(1-methyl-1H-1,2,3-triazol-4-yl)phenyl)amino)-6-(pyrazin-2-yl)pyrimidin-2-yl)-2-methylpiperidin-1-yl)ethan-1-one (018)

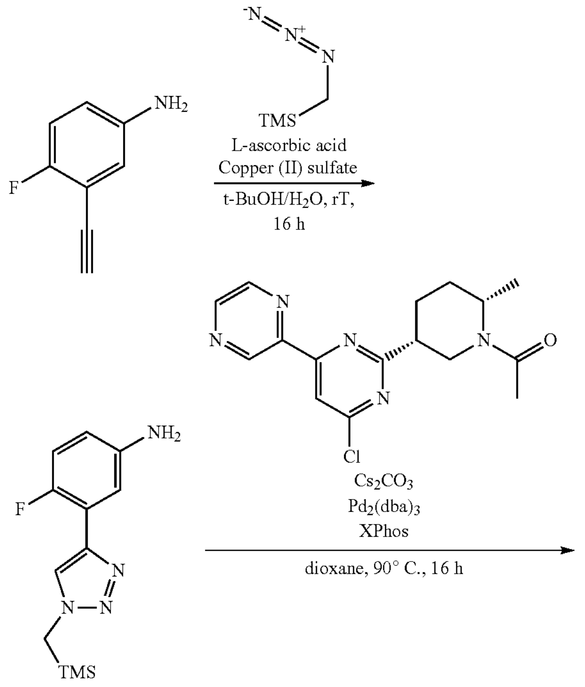

-continued

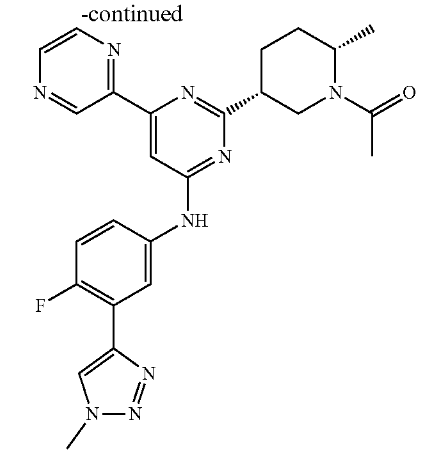

018

To a suspension of 3-ethynyl-4-fluoroaniline (50 mg, 0.37 mmol), L-ascorbic acid sodium salt (36.6 mg, 0.19 mmol) and copper(II) sulfate (14.76 mg, 0.09 mmol) in t-butanol (1 mL) and water (1 mL) was added trimethylsilylmethyl azide (0.06 mL, 0.37 mmol) and the mixture was stirred at room temperature for 16 hours. The mixture was filtered over Celite and the residue was rinsed with methanol. The filtrate was concentrated in vacuo to afford 4-fluoro-3-(1-((trimethylsilyl)methyl)-1H-1,2,3-triazol-4-yl)aniline (98 mg, 100%) as a yellow gum, which was used as such without further purification. LCMS (Method A): $t_R$ 1.72 min, 92%, MS (ESI) 265.1 $(M+H)^+$. Under argon atmosphere, 1-((2S,5R)-5-(4-chloro-6-(pyrazin-2-yl)pyrimidin-2-yl)-2-methylpiperidin-1-yl)ethan-1-one (Intermediate 1, 80 mg, 0.24 mmol), 4-fluoro-3-(1-((trimethylsilyl)methyl)-1H-1,2,3-triazol-4-yl)aniline (98 mg, 0.37 mmol) and cesium carbonate (157 mg, 0.48 mmol) were suspended in dry 1,4-dioxane (4 mL). Next, 2-dicyclohexylphosphino-2',4',6'-triisopropylbiphenyl (22.99 mg, 0.05 mmol) and tris(benzylideneacetone)dipalladium(0) (22.08 mg, 0.02 mmol) were added and the mixture was heated to 90° C. for 16 hours. The mixture was allowed to cool to room temperature, diluted with methanol and filtered over Celite, which was rinsed with methanol and the filtrate was concentrated in vacuo. The residue was redissolved in tetrahydrofuran (4 mL), 1M tetrabutylammonium fluoride in tetrahydrofuran (0.29 mL, 0.29 mmol) was added and the mixture was stirred at room temperature for 16 hours. The mixture was filtered over Celite, which was rinsed with methanol and the filtrate was concentrated in vacuo. The residue was purified by preparative reversed phase chromatography (Method B), chiral (preparative) SFC (Method D) and lyophilized to afford 1-((2S,5R)-5-(4-((4-fluoro-3-(1-methyl-1H-1,2,3-triazol-4-yl)phenyl)amino)-6-(pyrazin-2-yl)pyrimidin-2-yl)-2-methylpiperidin-1-yl) ethan-1-one (018, 9.8 mg, 8%) as a white solid. $^1H$-NMR (400 MHz, DMSO-d6, mixture of rotamers) δ 10.05 (d, J=5.5 Hz, 1H), 9.55 (d, J=14.1 Hz, 1H), 8.83-8.64 (m, 3H), 8.42 (d, J=3.7 Hz, 1H), 7.78-7.67 (m, 1H), 7.63 (d, J=3.4 Hz, 1H), 7.34 (td, J=9.7, 8.9, 2.3 Hz, 1H), 4.86-4.78 (m, 0.5H), 4.74-4.66 (m, 0.5H), 4.26-4.16 (m, 0.5H), 4.16-4.04 (m, 3.5H), 3.57-3.48 (m, 0.5H), 3.02-2.86 (m, 1H), 2.81-2.69 (m, 0.5H), 2.16-1.96 (m, 5H), 1.92-1.77 (m, 0.5H), 1.77-1.59 (m, 1.5H), 1.30-1.23 (m, 1.5H), 1.19-1.10 (m, 1.5H); UPLC (Method B): $t_R$ 1.34 min, 100%, MS (ESI) 488.2 $(M+H)^+$.

The following compounds were prepared following procedures analogous to Example 13, using the appropriate starting materials, and purified using reversed phase chromatography method A/B and/or prep-SFC.

| Compound # | Structure and compound name | Analytical data |
|---|---|---|
| 019 | 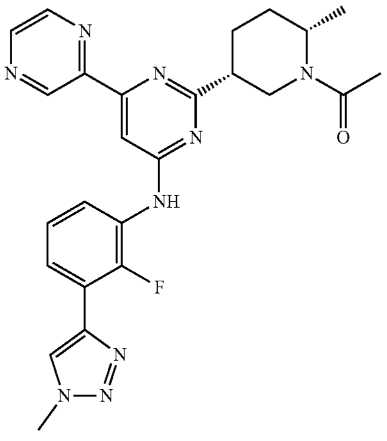 1-((2S,5R)-5-(4-((2-fluoro-3-(1-methyl-1H-1,2,3-triazol-4-yl)phenyl)amino)-6-(pyrazin-2-yl)pyrimidin-2-yl)-2-methylpiperidin-1-yl)ethan-1-one | $^{1}$H-NMR (400 MHz, DMSO-d6, mixture of rotamers) δ 9.77 (d, J = 6.5 Hz, 1H), 9.56 (dd, J = 12.3, 1.4 Hz, 1H), 8.83 - 8.76 (m, 2H), 8.44 (t, J = 3.7 Hz, 1H), 8.07-7.95 (m, 1H), 7.89 (t, J = 7.1 Hz, 1H), 7.71 (d, J = 7.6 Hz, 1H), 7.39-7.25 (m, 1H), 4.84-4.76 (m, 0.5H), 4.75-4.64 (m, 0.5H), 4.24-4.11 (m, 3.5H), 4.05-3.95 (m, 0.5H), 3.45-3.36 (m, 0.5H), 2.91-2.81 (m, 1H), 2.71 (m, 0.5H), 2.09-190 (m, 5H), 1.86-1.74 (m, 0.5H), 1.72-1.60 (m, 1.5H), 1.25-1.18 (m, 1.5H), 1.14-1.05 (m,1.5H); UPLC (Method B): $t_R$ 1.33 min, 100%, MS (ESI) 488.4 (M + H)$^+$. |
| 020 | 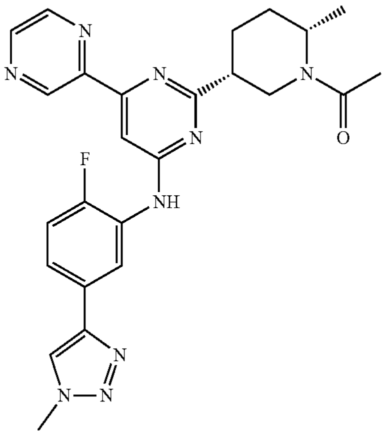 1-((2S,5R)-5-(4-((2-fluoro-5-(1-methyl-1H-1,2,3-triazol-4-yl)phenyl)amino)-6-(pyrazin-2-yl)pyrimidin-2-yl)-2-methylpiperidin-1-yl)ethan-1-one | $^{1}$H-NMR (400 MHz, DMSO-d6, mixture of rotamers) δ 9.75 (d, J = 11.7 Hz, 1H), 9.56 (dd, J = 11.1, 1.2 Hz, 1H), 8.82 - 8.78 (m, 2H), 8.71 (br s, 1H), 8.50 (d, J = 6.3 Hz, 1H), 7.84-7.70 (m, 1H), 7.65-7.52 (m, 1H), 7.43-7.35 (m, 1H), 4.83-4.71 (m, 1H), 4.27-4.14 (m, 0.5H), 4.09 (d, J = 7.5 Hz, 3H), 4.05-3.98 (m, 0.5H), 3.53-3.42 (m, 0.5H), 2.95-2.85 (m, 1H), 2.79-2.69 (m, 0.5H), 2.12-1.90 (m, 5H), 1.88-1.76 (m, 0.5H), 1.72-1.57 (m, 1.5H), 1.23-1.17 (m, 1.5H), 1.14-1.02 (m, 1.5H); UPLC (Method B): $t_R$ 1.35 min, 98%, MS (ESI) 488.2 (M + H)$^+$. |

Example 14: Synthesis of 1-((2S,5R)-5-(4-((3-chloro-5-(1-methyl-1H-1,2,3-triazol-4-yl)phenyl)amino)-6-(pyrazin-2-yl)pyrimidin-2-yl)-2-methylpiperidin-1-yl)ethan-1-one (021)

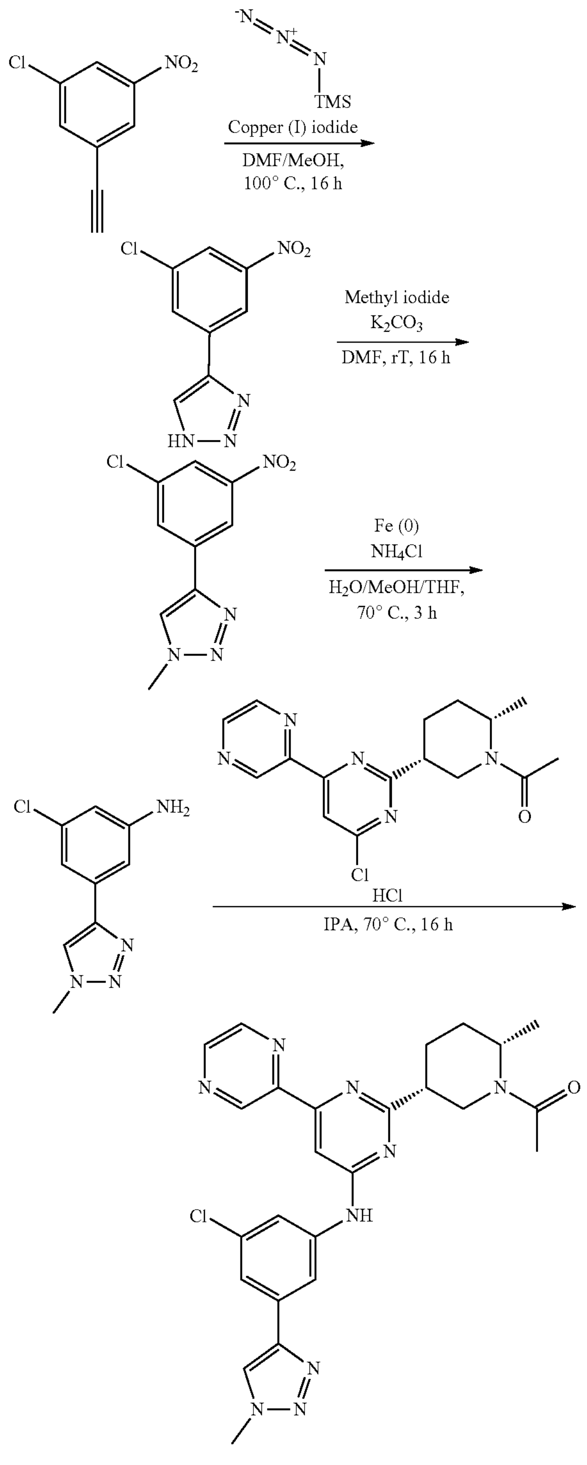

021

Under argon, azidotrimethylsilane (0.76 mL, 5.78 mmol) and copper(I) iodide (47 mg, 0.25 mmol) were added to a stirring solution of 1-chloro-3-ethynyl-5-nitrobenzene (700 mg, 3.86 mmol) in N,N-dimethylformamide (30 mL) and methanol (3 mL). The mixture was stirred at 100° C. for 16 hours. The mixture was allowed to cool to room temperature, poured into saturated aqueous ammonium chloride solution and extracted with ethyl acetate three times. The combined organic layers were washed with brine, dried over sodium sulfate, filtered and concentrated in vacuo. The residue was coated onto hydromatrix and purified by silica column chromatography (0% to 50% ethyl acetate in n-heptane) to afford 4-(3-chloro-5-nitrophenyl)-1H-1,2,3-triazole (650 mg, 75%) as a white solid. LCMS (Method C): $t_R$ 1.64 min, 95%, MS (ESI) 225.0 $(M+H)^+$. To a solution of 4-(3-chloro-5-nitrophenyl)-1H-1,2,3-triazole (290 mg, 1.29 mmol) in N,N-dimethylformamide (10 mL) were added potassium carbonate (232 mg, 1.68 mmol) and iodomethane (0.11 mL, 1.68 mmol). The mixture was stirred at room temperature for 16 hours and concentrated in vacuo The residue was coated onto hydromatrix and purified by silica column chromatography (0% to 50% ethyl acetate in n-heptane) to afford 4-(3-chloro-5-nitrophenyl)-1-methyl-1H-1,2,3-triazole (100 mg, 33%) as a yellow gum. $^1$H-NMR (400 MHz, DMSO-d6) δ 8.55-8.45 (m, 1H), 8.30-8.19 (m, 1H), 8.19-8.09 (m, 1H), 7.95 (s, 1H), 4.21 (s, 3H). To a solution of 4-(3-chloro-5-nitrophenyl)-1-methyl-1H-1,2,3-triazole (100 mg, 0.42 mmol) in water (3 mL), tetrahydrofuran (1.5 mL) and methanol (1.5 mL) were added ammonium chloride (67.2 mg, 1.26 mmol) and iron powder (70.2 mg, 1.26 mmol). The mixture was heated to 70° C. for 3 hours, the mixture was allowed to cool to room temperature and stirred with ethyl acetate. After 15 minutes the organic layer was decanted and the process was repeated twice. The combined organic layers were dried over sodium sulfate, filtered and concentrated in vacuo to afford 3-chloro-5-(1-methyl-1H-1,2,3-triazol-4-yl)aniline (80 mg, 91%) as an brown oil. LCMS (Method C): $t_R$ 1.68 min, 97%, MS (ESI) 209.0 $(M+H)^+$. To a mixture of 1-((2S,5R)-5-(4-chloro-6-(pyrazin-2-yl)pyrimidin-2-yl)-2-methylpiperidin-1-yl)ethan-1-one (Intermediate 1, 100 mg, 0.25 mmol) and 3-chloro-5-(1-methyl-1H-1,2,3-triazol-4-yl)aniline (80 mg, 0.38 mmol) in 2-propanol (5 mL) was added concentrated hydrochloric acid (drops) and the mixture was stirred at 70° C. for 3 days. The suspension was filtered over Celite, the filter cake was rinsed with diethyl ether three times, and dried in a vacuum oven at 40° C. for 16 hours to afford 1-((2S,5R)-5-(4-((3-chloro-5-(1-methyl-1H-1,2,3-triazol-4-yl)phenyl)amino)-6-(pyrazin-2-yl)pyrimidin-2-yl)-2-methylpiperidin-1-yl)ethan-1-one (021, 104 mg, 82%) as a white solid. $^1$H-NMR (400 MHz, DMSO-d6, mixture of rotamers) δ 10.34 (d, J=9.9 Hz, 1H), 9.56 (d, J=13.0 Hz, 1H), 8.85-8.79 (m, 2H), 8.61 (d, J=7.0 Hz, 1H), 8.30-8.22 (m, 1H), 8.15-8.01 (m, 1H), 7.69 (d, J=2.7 Hz, 1H), 7.55-7.50 (m, 1H), 4.87-4.80 (m, 0.5H), 4.80-4.70 (m, 0.5H), 4.30-4.18 (m, 0.5H), 4.14-4.04 (m, 3.5H), 3.55-3.46 (m, 0.5H), 3.02-2.92 (m, 1H), 2.88-2.76 (m, 0.5H), 2.16-1.97 (m, 5H), 1.93-1.79 (m, 0.5H), 1.77-1.61 (m, 1.5H), 1.36-1.27 (d, J=6.9 Hz, 1.5H), 1.19-1.13 (m, 1.5H). UPLC (Method A): $t_R$ 1.55 min, 97%, MS (ESI) 504.2 $(M+H)^+$; Chiral SFC (Method D): $t_R$ 3.18 min, 97%, MS (ESI) 504.1 $(M+H)^+$.

Example 15: Synthesis of 1-((2S,5R)-5-(4-((3-fluoro-5-(1-(oxetan-3-yl)-1H-1,2,3-triazol-4-yl)phenyl)amino)-6-(pyrazin-2-yl)pyrimidin-2-yl)-2-methylpiperidin-1-yl)ethan-1-one (022)

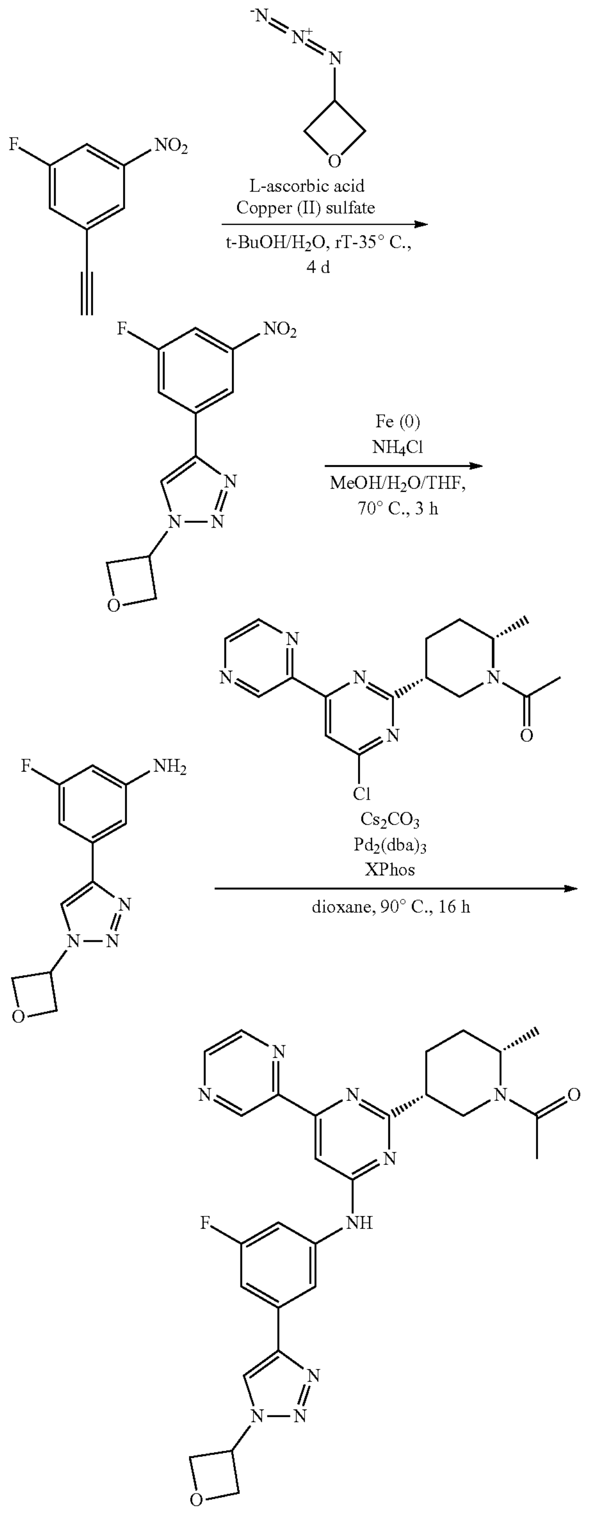

022

To a solution of 1-ethynyl-3-fluoro-5-nitrobenzene (prepared under Example 6, 125 mg, 0.76 mmol) in t-butanol (4 mL) and water (4 mL) was added 3-azidooxetane (0.5M in MTBE, 1.51 mL, 0.76 mmol) followed by L-ascorbic acid sodium salt (30.0 mg, 0.15 mmol) and copper(II) sulfate (24.2 mg, 0.15 mmol). The mixture was stirred at room temperature for 16 hours and at 35° C. for 16 hours. The mixture was diluted with ethyl acetate and water, the biphasic mixture was filtered over Celite and the layers of the filtrate were separated. The aqueous layer was extracted with ethyl acetate twice. The combined organic layers were washed with brine, dried over sodium sulfate, filtered and concentrated in vacuo. The residue was triturated in diethyl ether for 1 hour. The solids were filtered off, washed with diethyl ether and dried in a vacuum stove at 40° C. for 16 hours to afford 4-(3-fluoro-5-nitrophenyl)-1-(oxetan-3-yl)-1H-1,2,3-triazole (113 mg, 57%) as a beige solid. $^1$H-NMR (400 MHz, DMSO-d6) δ 9.27 (s, 1H), 8.60-8.57 (m, 1H), 8.24-8.18 (m, 1H), 8.14-8.07 (m, 1H), 5.97-5.88 (m, 1H), 5.12-5.05 (m, 2H), 4.96-4.90 (m, 2H); LCMS (Method A): $t_R$ 1.92 min, 100%, MS (ESI) 265.1 $(M+H)^+$. To a suspension of 4-(3-fluoro-5-nitrophenyl)-1-(oxetan-3-yl)-1H-1,2,3-triazole (139 mg, 0.53 mmol) in methanol (1.5 mL), tetrahydrofuran (1.5 mL) and water (3 mL) were added ammonium chloride (84 mg, 1.58 mmol) and iron powder (88 mg, 1.58 mmol). The mixture was stirred at 70° C. for 4 hours and room temperature for 16 hours. The mixture was diluted with ethyl acetate and water and stirred vigorously for 15 minutes. The organic layer was decanted and this procedure was repeated twice. The combined organic layers were dried over sodium sulfate, filtered and concentrated in vacuo to afford 3-fluoro-5-(1-(oxetan-3-yl)-1H-1,2,3-triazol-4-yl)aniline (108 mg, 75%) as a brown oil. $^1$H-NMR (400 MHz, DMSO-d6) δ 8.78 (s, 1H), 6.98-6.96 (m, 1H), 6.76-6.70 (m, 1H), 6.32-6.26 (m, 1H), 5.90-5.81 (m, 1H), 5.57 (s, 2H), 5.06-5.01 (m, 2H), 4.96-4.90 (m, 2H); LCMS (Method C): $t_R$ 1.43 min, 85%, MS (ESI) 235.1 $(M+H)^+$. Under argon, 1-((2S,5R)-5-(4-chloro-6-(pyrazin-2-yl)pyrimidin-2-yl)-2-methylpiperidin-1-yl)ethan-1-one (Intermediate 1, 80 mg, 0.24 mmol), 3-fluoro-5-(1-(oxetan-3-yl)-1H-1,2,3-triazol-4-yl)aniline (106 mg, 0.39 mmol), 2-dicyclohexylphosphino-2',4',6'-triisopropylbiphenyl (22.99 mg, 0.05 mmol), tris(dibenzylideneacetone)dipalladium(0) (22.1 mg, 0.02 mmol) and cesium carbonate (157 mg, 0.48 mmol) were suspended in dry 1,4-dioxane (4 mL) and the mixture was stirred at 90° C. for 16 hours. The mixture was allowed to cool to room temperature, diluted with methanol and filtered over Celite. The residue was rinsed with methanol and the filtrate was concentrated in vacuo. The crude product was purified by chiral (preparative) SFC (Method D) and lyophilized to afford 1-((2S,5R)-5-(4-((3-fluoro-5-(1-(oxetan-3-yl)-1H-1,2,3-triazol-4-yl)phenyl)amino)-6-(pyrazin-2-yl)pyrimidin-2-yl)-2-methylpiperidin-1-yl)ethan-1-one (022, 60.5 mg, 47%) as a light yellow solid. $^1$H-NMR (400 MHz, DMSO-d6, mixture of rotamers) δ 10.27 (d, J=9.7 Hz, 1H), 9.57 (d, J=12.9 Hz, 1H), 8.94 (d, J=8.4 Hz, 1H), 8.85-8.79 (m, 2H), 8.16 (d, J=7.2 Hz, 1H), 7.88 (dd, J=33.8, 11.6 Hz, 1H), 7.71-7.66 (m, 1H), 7.37-7.30 (m, 1H), 5.96-5.86 (m, 1H), 5.10-5.03 (m, 2H), 5.00-4.91 (m, 2H), 4.89-4.72 (m, 1H), 4.28-4.19 (m, 0.5H), 4.14-4.07 (m, 0.5H), 3.55-3.46 (m, 0.5H), 3.02-2.90 (m, 1H), 2.85-2.75 (m, 0.5H), 2.17-1.96 (m, 5H), 1.92-1.81 (m, 0.5H), 1.79-1.61 (m, 1.5H), 1.34-1.26 (m, 1.5H), 1.17-1.09 (m, 1.5H); UPLC (Method B): $t_R$ 1.42 min, 96%, MS (ESI) 530.4 $(M+H)^+$.

The following compounds were prepared following procedures analogous to Example 15, using the appropriate starting materials, and purified using reversed phase chromatography method A/B and/or prep-SFC.

| Compound # | Structure and compound name | Analytical data |
| --- | --- | --- |
| 023 | 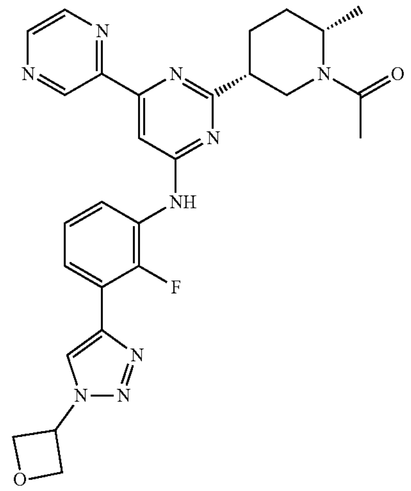 1-((2S,5R)-5-(4-((2-fluoro-3-(1-(oxetan-3-yl)-1H-1,2,3-triazol-4-yl)phenyl)amino)-6-(pyrazin-2-yl)pyrimidin-2-yl)-2-methylpiperidin-1-yl)-ethan-1-one | $^{1}$H-NMR (400 MHz, DMSO-d6, mixture of rotamers) δ 9.78 (d, J = 6.4 Hz, 1H), 9.56 (dd, J = 12.0, 1.4 Hz, 1H), 8.82-8.75 (m, 2H), 8.66 (d, J = 3.4 Hz, 1H), 8.11-7.95 (m, 1H), 7.95-7.86 (m, 1H), 7.71 (d, J = 9.0 Hz, 1H), 7.39-7.31 (m, 1H), 5.99-5.90 (m, 1H), 5.09-4.96 (m, 4H), 4.84-4.75 (m, 0.5H), 4.76-4.63 (m, 0.5H), 4.24-4.13 (m, 0.5H), 4.07-3.96 (m, 0.5H), 3.46-3.37 (m, 0.5H), 2.91-2.80 (m, 1H), 2.74-2.65 (m, 0.5H), 2.10-1.86 (m, 5H), 1.86-1.73 (m, 0.5H), 1.73-1.57 (m, 1.5H), 1.28-1.19 (m, 1.5H), 1.13-1.04 (m, 1.5H). UPLC (Method B): $t_R$ 1.33 min, 96%, one MS (ESI) 530.4 $(M + H)^+$. |

Example 16: Synthesis of sodium (2-((3R,6S)-1-acetyl-6-methyl piperidin-3-yl)-6-(pyrazin-2-yl)pyrimidin-4-yl)(2-fluoro-3-(1-methyl-1H-1,2,3-triazol-4-yl)phenyl)amide (019.Na)

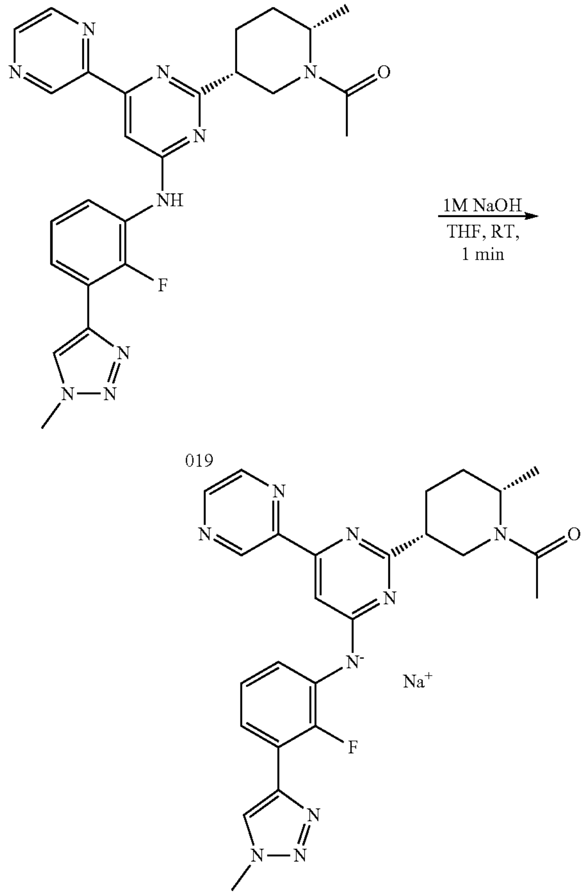

019

019.Na

To a suspension of 1-((2S,5R)-5-(4-((2-fluoro-3-(1-methyl-1H-1,2,3-triazol-4-yl)phenyl)amino)-6-(pyrazin-2-yl)pyrimidin-2-yl)-2-methylpiperidin-1-yl)ethan-1-one (019, 50 mg, 0.10 mmol) in tetrahydrofuran (1 mL) was added a 1M aqueous sodium hydroxide solution (0.10 mL, 0.10 mmol) and the mixture was stirred at room temperature for 1 minute to afford a light yellow solution. The solution was concentrated and co-evaporated with toluene (1 mL) twice. The residue was suspended in diethyl ether (2 mL) and stirred for 1 minute. The solid was filtered off and air-dried under nitrogen flow to afford sodium (2-((3R,6S)-1-acetyl-6-methylpiperidin-3-yl)-6-(pyrazin-2-yl)pyrimidin-4-yl)(2-fluoro-3-(1-methyl-1H-1,2,3-triazol-4-yl)phenyl)amide (019.Na, 45 mg, 86%) as a yellow solid. $^{1}$H-NMR (400 MHz, DMSO-$d_6$, mixture of rotamers) δ 9.50 (d, J=6.0 Hz, 1H), 8.74 (s, 2H), 8.38 (dd, J=8.4, 3.8 Hz, 1H), 7.91-7.67 (m, 2H), 7.57-7.34 (m, 1H), 7.30-7.11 (m, 1H), 4.85-4.73 (m, 0.5H), 4.71-4.60 (m, 0.5H), 4.21-4.15 (m, 0.5H), 4.15-4.08 (m, 3H), 4.00-3.92 (m, 0.5H), 2.93-2.80 (m, 0.5H), 2.80-2.70 (m, 0.5H), 2.70-2.56 (m, 1H), 2.16-1.86 (m, 5H), 1.86-1.72 (m, 0.5H), 1.72-1.56 (m, 1.5H), 1.27-1.18 (m, 1.5H), 1.12-1.09 (m, 1.5H).

The following compound was prepared following procedures analogous to Example 16, using the appropriate starting materials.

| Compound # | Structure and compound name | Analytical data |
|---|---|---|
| 001.Na | 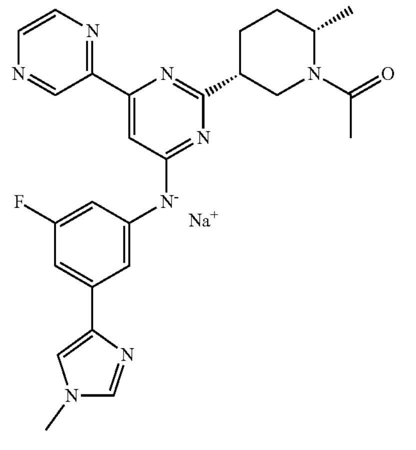 sodium (2-((3R,6S)-1-acetyl-6-methylpiperidin-3-yl)-6-(pyrazin-2-yl)pyrimidin-4-yl)(3-fluoro-5-(1-methyl-1H-imidazol-4-yl)phenyl)amide | $^1$H-NMR (400 MHz, DMSO-d6, mixture of rotamers) δ 9.46 (d, J = 4.5 Hz, 1H), 8.85-8.58 (m, 2H), 7.88-7.71 (m, 1H), 7.64-7.36 (m, 3H), 7.12-6.96 (m, 1H), 4.88-4.77 (m, 0.5H), 4.73-4.66 (m, 0.5H), 4.25-4.16 (m, 0.5), 4.07-3.95 (m, 0.5H), 3.75-3.64 (m, 3H), 3.01-2.86 (m, 0.5H), 2.81-2.56 (m, 1H), 2.10-1.95 (m, 5.5H), 1.89-1.77 (m, 0.5H), 1.77-1.63 (m, 1.5H), 1.33-1.21 (m, 1.5H), 1.19-1.10 (m, 1.5H). |

Example 17: Synthesis of 1-((2S,5R)-5-(4-((3-fluoro-5-(1-methyl-1H-imidazol-4-yl)phenyl)amino)-6-(pyrazin-2-yl)pyrimidin-2-yl)-2-methylpiperidin-1-yl)ethan-1-one hydrochloride (001.HCl)

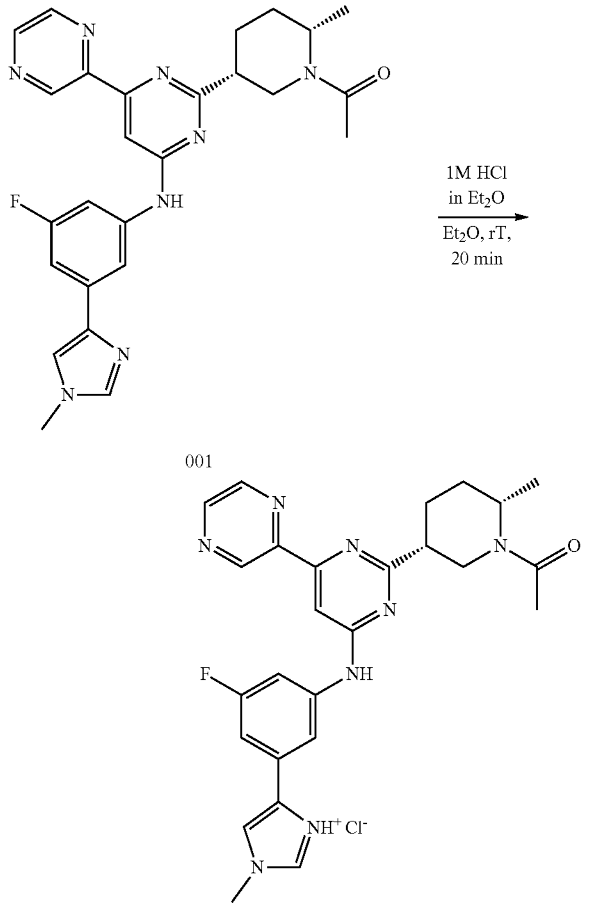

001

001.HCl

To a suspension of 1-((2S,5R)-5-(4-((3-fluoro-5-(1-methyl-1H-imidazol-4-yl)phenyl)amino)-6-(pyrazin-2-yl)pyrimidin-2-yl)-2-methylpiperidin-1-yl)ethan-1-one (001, 51.7 mg, 0.11 mmol) in dry diethyl ether (1 mL) was added 1M hydrochloric acid in diethyl ether (0.27 ml, 5.31 mmol) and the mixture was stirred at room temperature for 20 minutes. The resulting solids were filtered off and washed with diethyl ether to afford a yellow solid. The solid was dried under vacuum for 8 hours (40° C.) to afford 1-((2S,5R)-5-(4-((3-fluoro-5-(1-methyl-1H-imidazol-4-yl)phenyl)amino)-6-(pyrazin-2-yl)pyrimidin-2-yl)-2-methylpiperidin-1-yl)ethan-1-one hydrochloride (001.HCl, 40.7 mg, 71%) as a yellow solid. $^1$H-NMR (400 MHz, DMSO-d6, mixture of rotamers) δ 10.44 (d, J=15.2 Hz, 1H), 9.58 (d, J=10.2 Hz, 1H), 9.20-9.00 (m, 1H), 8.82 (s, 2H), 8.24-7.92 (m, 2H), 7.86-7.64 (m, 2H), 7.40-7.27 (m, 1H), 4.93-4.77 (m, 1H), 4.36-4.18 (m, 0.5H), 4.15-4.03 (m, 0.5H), 3.99-3.85 (m, 3H), 3.03-2.73 (m, 1.5H), 2.20-1.94 (m, 5.5H), 1.94-1.80 (m, 0.5H), 1.78-1.61 (m, 1.5H), 1.30-1.20 (m, 1.5H), 1.17-1.05 (m, 1.5H).

Example 18: Synthesis of sodium (2-((3R,6S)-1-acetyl-6-methylpiperidin-3-yl)-6-(pyrazin-2-yl)pyrimidin-4-yl)(3-(1-methyl-1H-1,2,3-triazol-4-yl)phenyl)amide (024.Na)

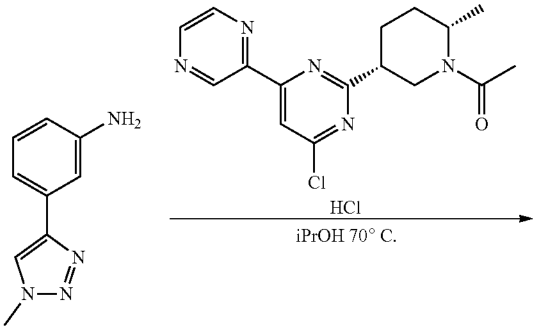

-continued

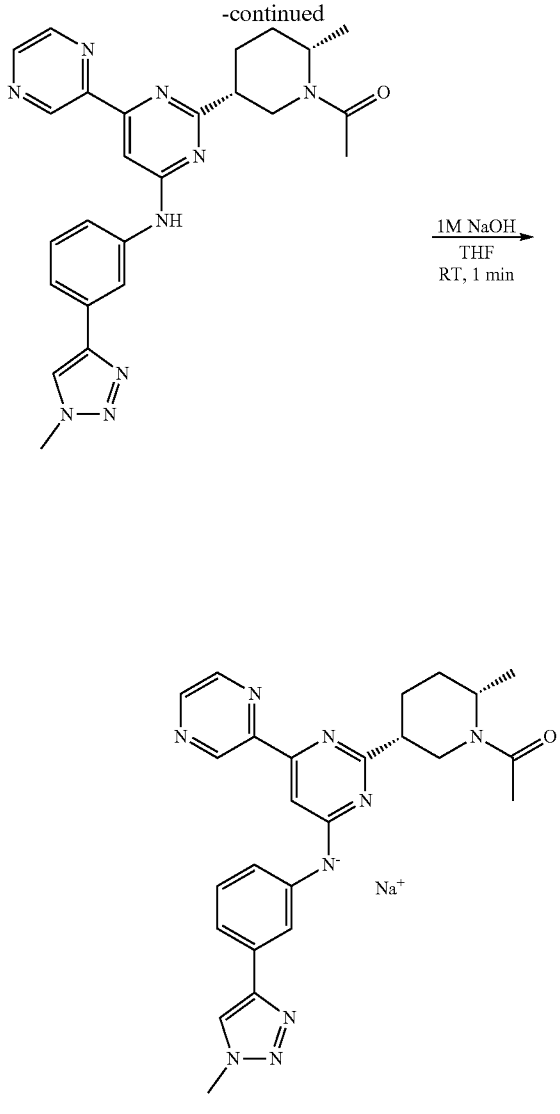

024.Na

To a solution of 1-((2S,5R)-5-(4-chloro-6-(pyrazin-2-yl) pyrimidin-2-yl)-2-methylpiperidin-1-yl)ethan-1-one (Intermediate 1, 120 mg, 0.36 mmol) in 2-propanol (2 mL), was added 3-(1-methyl-1H-1,2,3-triazol-4-yl)aniline (188 mg, 1.08 mmol) and hydrochloric acid (0.08 mL, 1.08 mmol). The mixture was stirred at 70° C. for 16 hours, poured into saturated aqueous sodium bicarbonate solution and extracted with ethyl acetate twice. The combined organic layers were dried over sodium sulfate and concentrated to afford a yellow oil. The oil was purified with reversed phase chromatography (method B) and lyophilized to afford 1-((2S,5R)-2-methyl-5-(4-((3-(1-methyl-1H-1,2,3-triazol-4-yl)phenyl)amino)-6-(pyrazin-2-yl)pyrimidin-2-yl)piperidin-1-yl)ethan-1-one (102 mg, 60%) as a white solid. $^1$H-NMR (400 MHz, DMSO-d6, mixture of rotamers)δ 10.01 (d, J=5.6 Hz, 1H), 9.56 (dd, J=11.0, 1.1 Hz, 1H), 8.80 (d, J=1.5 Hz, 2H), 8.54-8.42 (m, 2H), 7.72-7.54 (m, 2H), 7.53-7.39 (m, 2H), 4.86-4.76 (m, 1H), 4.27-4.16 (m, 0.5H), 4.15-4.03 (m, 3.5H), 3.58-3.42 (m, 0.5H), 3.00-2.86 (m, 1H), 2.86-2.68 (m, 0.5H), 2.17-1.96 (m, 5H), 1.93-1.77 (m, 0.5H), 1.76-1.64 (m, 1.5H), 1.27 (d, J=6.8 Hz, 1.5H), 1.13 (d, J=7.0 Hz, 1.5H); LCMS (Method D): $t_R$ 3.31 min, MS (ESI) 470.2 $(M+H)^+$. To a suspension of 1-((2S,5R)-2-methyl-5-(4-((3-(1-methyl-1H-1,2,3-triazol-4-yl)phenyl)amino)-6-(pyrazin-2-yl)pyrimidin-2-yl)piperidin-1-yl)ethan-1-one (50 mg, 0.11 mmol) in tetrahydrofuran (1 mL) was added a 1M aqueous sodium hydroxide solution (0.11 mL, 0.11 mmol) and the mixture was stirred at room temperature for 1 min to afford a light yellow solution. The solution was concentrated and co-evaporated with toluene (1 mL) twice. The residue was suspended in diethyl ether (2 mL) and stirred for 1 minute. The solid was filtered off and air-dried under nitrogen flow to afford sodium (2-((3R,6S)-1-acetyl-6-methylpiperidin-3-yl)-6-(pyrazin-2-yl)pyrimidin-4-yl)(3-(1-methyl-1H-1,2,3-triazol-4-yl)phenyl)amide (024.Na, 46 mg, 88%) as a yellow solid. $^1$H-NMR (400 MHz, DMSO-d6, mixture of rotamers) δ 9.44 (s, 1H), 8.68 (s, 2H), 8.38 (d, J=15.5 Hz, 1H), 8.00 (s, 1H), 7.49-7.02 (m, 4H), 4.84-4.63 (m, 1H), 4.33-4.14 (m, 0.5H), 4.07 (d, J=7.4 Hz, 3H), 4.04-3.89 (m, 0.5H), 2.98-2.82 (m, 0.5H), 2.73-2.53 (m, 1H), 2.12-1.89 (m, 5.5H), 1.88-1.73 (m, 0.5H), 1.72-1.57 (m, 1.5H), 1.28-1.19 (m, 1.5H), 1.14-1.05 (m, 1.5H).

Assay Data

Assay 1

Multiple Myeloma Cellular Efficacy:

10000 OPM-2 (ACC50; DSMZ) were plated into wells of a 384 well plate (Greiner 781090). Cells were treated for 4 days with a dose range of compound or vehicle. At the end of the experiment cells were stained directly with PrestoBlue (ThermoFisher Scientific; A13262) for 2 hours at 37° C. in a humidified incubator according to manufactor's instruction. To assess the relative cell number the PrestoBlue signal was measured using either a TecanM1000Pro reader or a Tecan Sparks reader following the manufactor's instructions. Background (no cells) values were subtracted and set in relation to the vehicle control. To assess the $EC_{50}$ of each compound the relative fluorescence value was plotted against the compound concentration after log transformation. Data were fitted in a nonlinear manner with a variable slope (four parameters) using graphpad prism software. Cellular efficacy of compounds was evaluated in the multiple myeloma cell line OPM-2 using the cell proliferation/survival assay PrestoBlue. $EC_{50}$ values are classified as indicated below.

Assay 2

CBP Bromodomain Binding Assay (TR-FRET)

Compounds solutions of 10 mM in DMSO were prediluted in DSMO to 25× stock solutions in DMSO. These were then diluted down to 4× in assay buffer. A dilution series in assay buffer was performed keeping the DMSO concentration stable. 5 μl compound in assay buffer was transferred into the assay plate (provided by assay kit) and the TR-FRET assay Cayman chemicals; 600850) was performed using the provider's instructions. After 1 hour incubation at room temperature in the darks, assay plates were read in a Tecan M1000 plate reader or a Tecan Sparks reader using the TR-FRET mode (top read; excitation 340 nM bandwidth 20 nM; emission 620 nM bandwidth 7 nM; gain optimal determined for the first well, number of flashes: 5; flash frequency 100 Hz; integration time: 500 μs, lag time: 100 μs, room temperature). The TR-FRET ratio was calculated by dividing 670 nm emission by 620 nm emission. Values were log transformed and non-linear regression with variable slope (4 parameters) was used to fit values to a dose-response curve to evaluate EC50 values.

| Compound # | Assay 1 (nM) | Assay 2 (nM) |
|---|---|---|
| 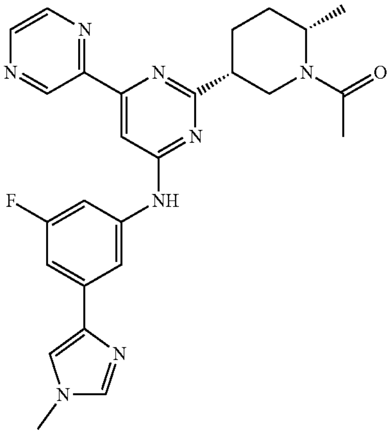 [SMILES: CC(=O)N1C[C@H](c2nc(Nc3cc(F)cc(-c4c[nH]nn4)c3)cc(-c3cnccn3)n2)CC[C@@H]1C] 001 | 1 | 7 |
| 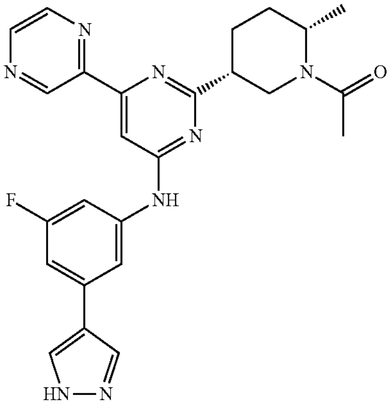 002 | 25 | 23 |
| 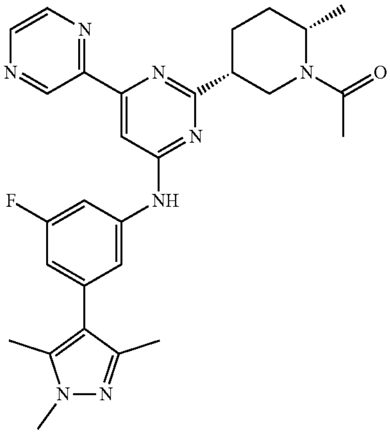 003 | 968 | |
-continued
| Compound # | Assay 1 (nM) | Assay 2 (nM) |
|---|---|---|
| 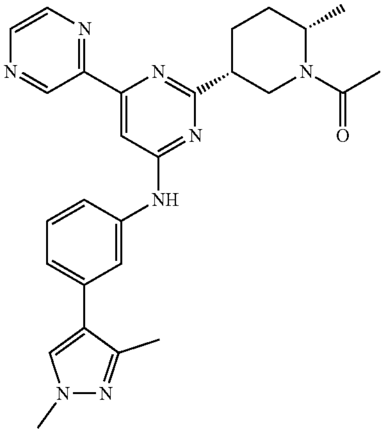 004 | | 128 |
| 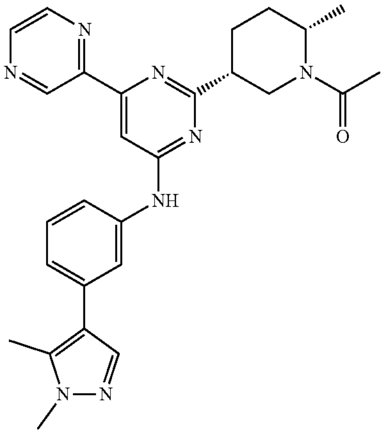 005 | 193 | |
| 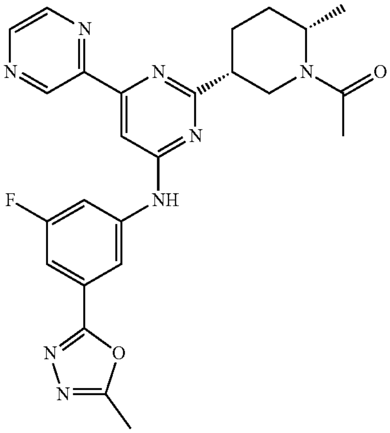 006 | 6 | 3 |

-continued
| Compound # | Assay 1 (nM) | Assay 2 (nM) |
|---|---|---|
| 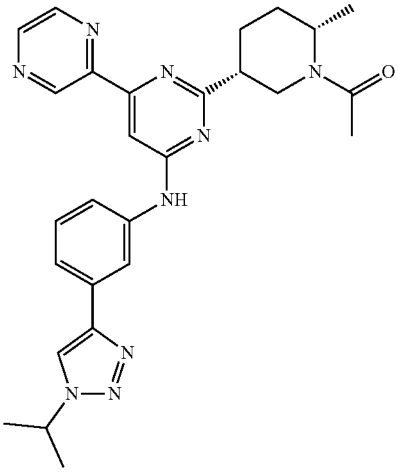 007 | 50 | |
| 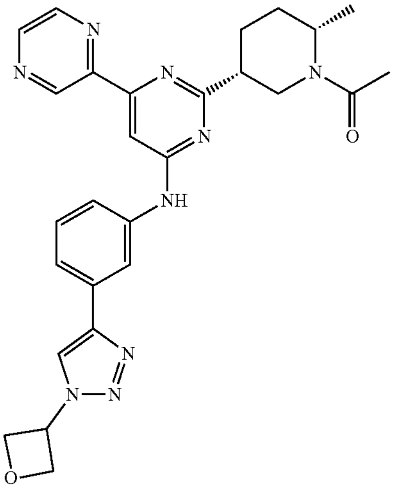 008 | 28 | |
| 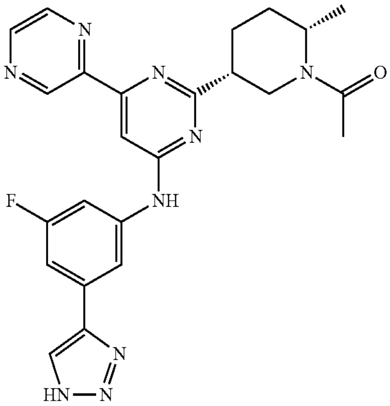 009 | 37 | |
-continued
| Compound # | Assay 1 (nM) | Assay 2 (nM) |
|---|---|---|
| 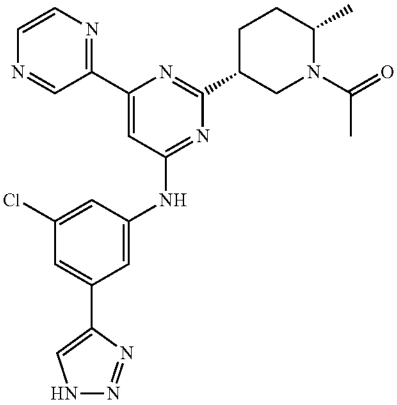 010 | 45 | |
| 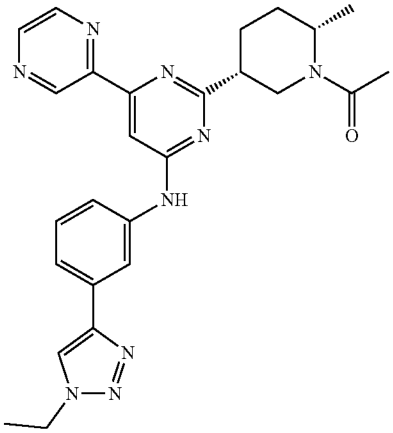 011 | 6 | |
| 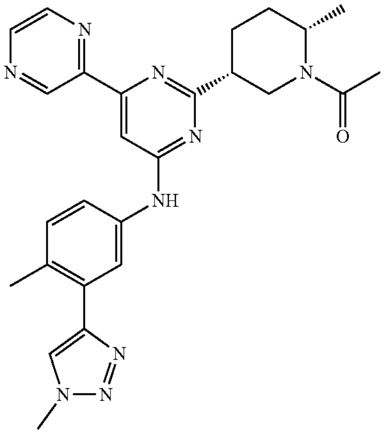 012 | 261 | |

-continued
| Compound # | Assay 1 (nM) | Assay 2 (nM) |
|---|---|---|
| 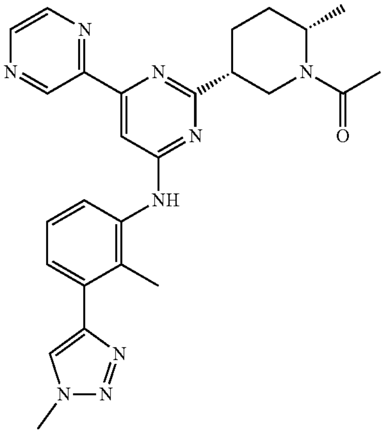 013 | 32 | |
| 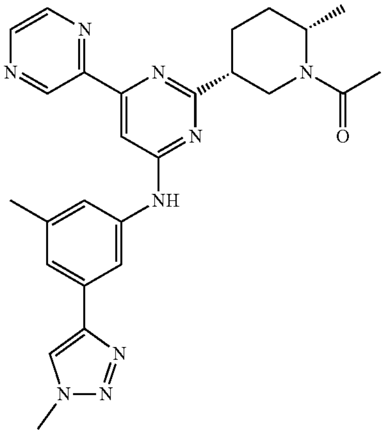 014 | 5 | 7 |
| 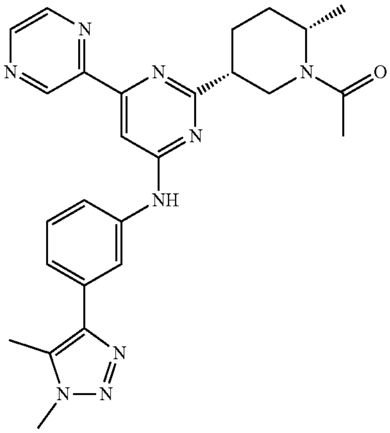 015 | 109 | |
-continued
| Compound # | Assay 1 (nM) | Assay 2 (nM) |
|---|---|---|
| 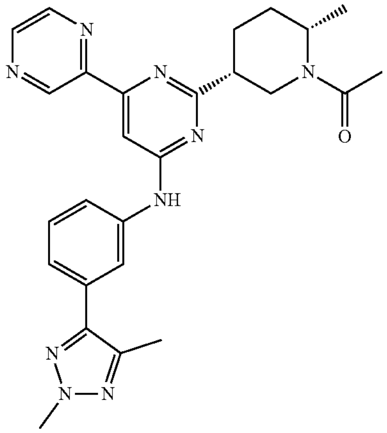 016 | 142 | |
| 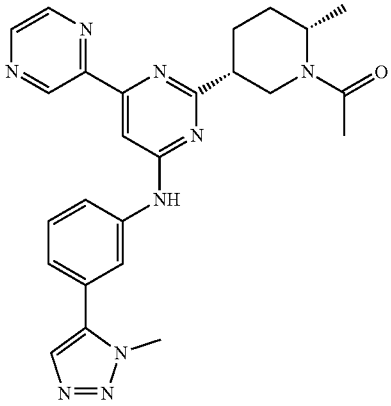 017 | 458 | |
| 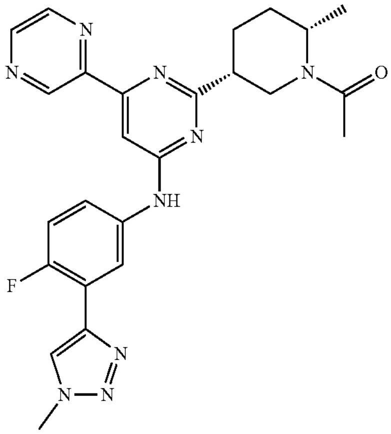 018 | 63 | 22 |

-continued
| Compound # | Assay 1 (nM) | Assay 2 (nM) |
|---|---|---|
| 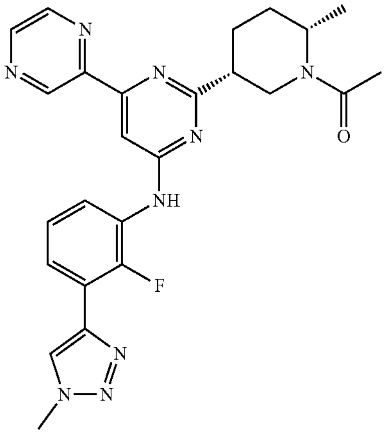 019 | 1 | 6 |
| 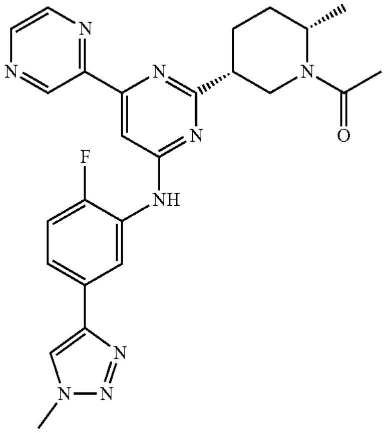 020 | 864 | |
| 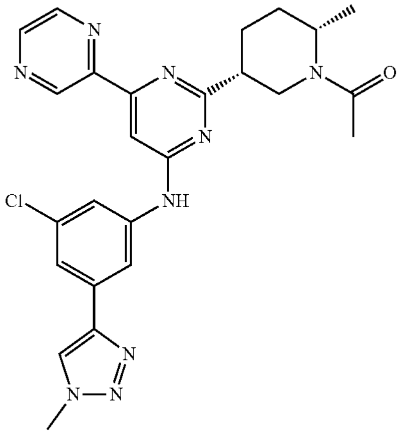 [SMILES: CC(=O)N1C[C@H](c2nc(Nc3cc(Cl)cc(-c4c[nH]nn4)c3)cc(-c3cnccn3)n2)CC[C@@H]1C] 021 | 5 | |
-continued
| Compound # | Assay 1 (nM) | Assay 2 (nM) |
|---|---|---|
| 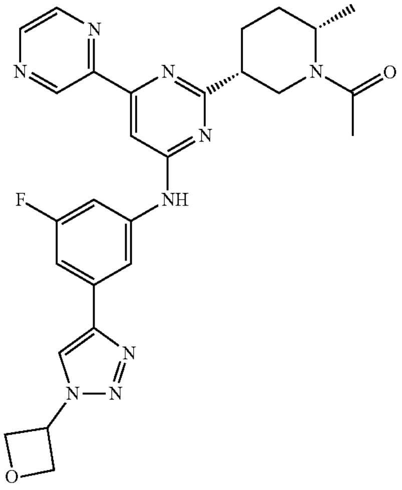 022 | 13 | |
| 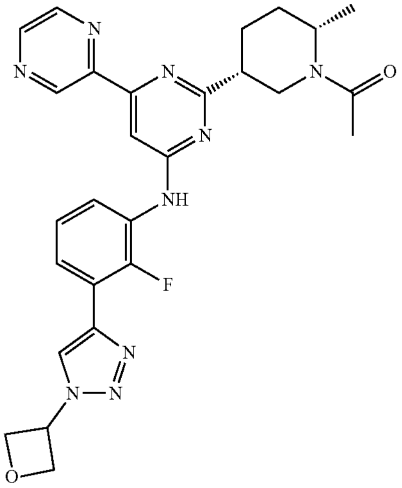 023 | 7 | 65 |

The invention claimed is:

1. A compound having the following formula:

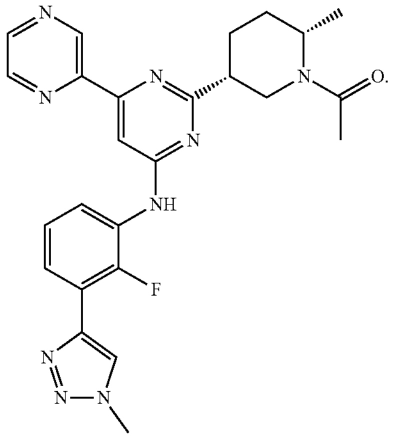 [SMILES: CC(=O)N1C[C@H](c2nc(Nc3cccc(-c4cn(C)nn4)c3F)cc(-c3cnccn3)n2)CC[C@@H]1C]

or a pharmaceutically acceptable salt, solvate, cocrystal tautomer, or a mixture thereof.

2. A pharmaceutical composition comprising a pharmaceutically effective amount of the compound according to claim 1 or a pharmaceutically acceptable salt, solvate, cocrystal, tautomer or a mixture thereof, and a pharmaceutically acceptable carrier, diluent or excipient.

3. A compound having the following formula:

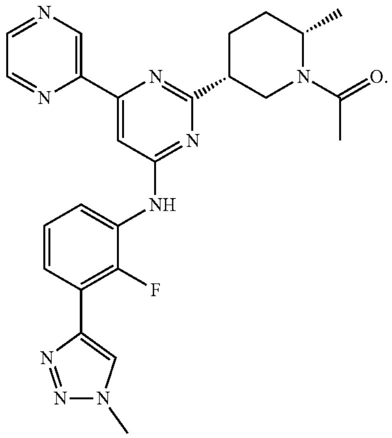 [SMILES: CC(=O)N1C[C@H](c2nc(Nc3cccc(-c4cn(C)nn4)c3F)cc(-c3cnccn3)n2)CC[C@@H]1C]

4. A pharmaceutical composition comprising a pharmaceutically effective amount of the compound according to claim 3 and a pharmaceutically acceptable carrier, diluent or excipient.

* * * * *